US011400177B2

(12) United States Patent
Wald et al.

(10) Patent No.: US 11,400,177 B2
(45) Date of Patent: *Aug. 2, 2022

(54) GERMICIDAL LIGHTING

(71) Applicant: Wangs Alliance Corporation, Port Washington, NY (US)

(72) Inventors: Shelley S. Wald, West Lake Hills, TX (US); Voravit Puvanakijjakorn, Port Washington, NY (US); Rong Feng Yu, Brooklyn, NY (US); David Xin Wang, Great Neck, NY (US); Li Changyong, Dongguan (CN); Zhou Tingting, Dongguan (CN)

(73) Assignee: Wangs Alliance Corporation, Port Washington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/542,702

(22) Filed: Dec. 6, 2021

(65) Prior Publication Data

US 2022/0088252 A1    Mar. 24, 2022

Related U.S. Application Data

(63) Continuation of application No. 17/319,432, filed on May 13, 2021.

(Continued)

(30) Foreign Application Priority Data

Mar. 17, 2021  (CN) .......................... 202120548631.2

(51) Int. Cl.
*A61L 9/20*  (2006.01)
*A61L 9/00*  (2006.01)
*A61L 9/22*  (2006.01)

(52) U.S. Cl.
CPC .................................. *A61L 9/00* (2013.01);
*A61L 9/20* (2013.01); *A61L 9/22* (2013.01);
*A61L 2209/111* (2013.01); *A61L 2209/15* (2013.01)

(58) Field of Classification Search
None
See application file for complete search history.

(56) References Cited

U.S. PATENT DOCUMENTS 3,629,587 A    12/1971   Decupper
4,422,824 A    12/1983   Eisenhardt, Jr.
(Continued)

FOREIGN PATENT DOCUMENTS

CN    201575354 U    9/2010
CN    102225214 B    10/2011
(Continued)

OTHER PUBLICATIONS

"Massive Airflow-Maximum Comfort," Delta T, LLC, Retrieved on Jun. 17, 2020.
(Continued)

*Primary Examiner* — James Choi
(74) *Attorney, Agent, or Firm* — Weiss & Arons LLP

(57) ABSTRACT

Apparatus, methods and instructions for disinfecting air. The apparatus may include, and the methods may involve, a fixture. The fixture may include a germicidal light source. The fixture may include a fan. The fan may circulate air through a volume into which the germicidal light source propagates germicidal light. The light source may be configured to emit, upward from a horizontal plane, a beam that, absent reflection off an environmental object, does not cross the horizontal plane. The apparatus may include a shield that prevents light from the light source from crossing the
(Continued)

horizontal plane. The sensor may face upward from the horizontal plane. The sensor may face downward from the horizontal plane.

30 Claims, 42 Drawing Sheets

Related U.S. Application Data

(60) Provisional application No. 63/027,315, filed on May 19, 2020, provisional application No. 63/026,702, filed on May 18, 2020.

(56) References Cited

U.S. PATENT DOCUMENTS

| | | | |
|---|---|---|---|
| 4,559,467 | A | 12/1985 | Beckmann et al. |
| 5,151,011 | A | 9/1992 | Rezek |
| 2,354,817 | A | 8/1994 | Law |
| 5,795,131 | A | 8/1998 | Crowhurst et al. |
| 5,855,295 | A | 1/1999 | Lee |
| 5,887,785 | A | 3/1999 | Yilmaz |
| 5,891,399 | A | 4/1999 | Owesen |
| 6,120,262 | A | 9/2000 | McDonough et al. |
| 6,160,956 | A | 12/2000 | Pelonis |
| 6,176,736 | B1 | 1/2001 | Hsu |
| 6,244,820 | B1 | 6/2001 | Yilmaz |
| 6,247,894 | B1 | 6/2001 | Moody et al. |
| 6,309,083 | B1 | 10/2001 | Lathrop et al. |
| 6,398,970 | B1 | 6/2002 | Justel et al. |
| 6,461,032 | B2 | 10/2002 | McKinley |
| 6,656,424 | B1 | 12/2003 | Deal |
| 7,160,566 | B2 | 1/2007 | Fink et al. |
| 7,177,133 | B2 | 2/2007 | Riskin |
| 7,407,624 | B2 | 8/2008 | Cumberland |
| 7,449,053 | B2 | 11/2008 | Hallam |
| 7,520,978 | B2 | 4/2009 | Harbers |
| 7,591,962 | B2 | 9/2009 | Justel et al. |
| 7,763,212 | B2 | 7/2010 | McEllen |
| 7,879,299 | B2 | 2/2011 | McEllen |
| 7,969,707 | B2 | 6/2011 | Riskin |
| 7,988,923 | B2 | 8/2011 | Fink et al. |
| 8,080,203 | B2 | 12/2011 | First et al. |
| 8,080,819 | B2 | 12/2011 | Mueller et al. |
| 8,097,092 | B2 | 1/2012 | Derra et al. |
| 8,106,367 | B2 | 1/2012 | Riskin |
| 8,114,342 | B2 | 2/2012 | Jung et al. |
| 8,114,346 | B2 | 2/2012 | Hyde et al. |
| 8,124,012 | B2 | 2/2012 | Leroux et al. |
| 8,143,591 | B2 | 3/2012 | Gefter et al. |
| 8,207,821 | B2 | 6/2012 | Roberge et al. |
| 8,398,264 | B2 | 3/2013 | Anderson et al. |
| 8,575,838 | B2 | 11/2013 | Raas et al. |
| 8,607,616 | B2 | 12/2013 | Marra |
| 8,611,065 | B2 | 12/2013 | Riskin |
| 8,667,707 | B2 | 3/2014 | Date et al. |
| 8,672,649 | B2 | 3/2014 | Smith et al. |
| 8,747,754 | B2 | 6/2014 | Abate |
| 8,795,590 | B1 | 8/2014 | Ellis |
| 8,808,972 | B2 | 8/2014 | Wang et al. |
| 8,834,789 | B2 | 9/2014 | Schiene et al. |
| 8,835,875 | B2 | 9/2014 | She et al. |
| 8,861,167 | B2 | 10/2014 | Waddell et al. |
| 8,877,124 | B2 | 11/2014 | Bergman |
| 8,891,058 | B2 | 11/2014 | Metzmacher et al. |
| D720,446 | S | 12/2014 | Ellis |
| 8,900,519 | B2 | 12/2014 | Krosney et al. |
| 8,907,304 | B2 | 12/2014 | Kreitenberg |
| 8,921,806 | B2 | 12/2014 | Broer et al. |
| 8,922,971 | B2 | 12/2014 | Abate et al. |
| 8,936,944 | B2 | 1/2015 | Peltz et al. |
| 8,957,571 | B2 | 2/2015 | Riskin |
| 8,993,988 | B2 | 3/2015 | Nathan et al. |
| 8,999,238 | B2 | 4/2015 | Kreitenberg |
| 9,039,966 | B2 | 5/2015 | Anderson et al. |
| 9,045,358 | B2 | 6/2015 | Greuel |
| 9,144,618 | B2 | 9/2015 | Kreitenberg |
| 9,149,549 | B2 | 10/2015 | Kreitenberg |
| 9,186,475 | B2 | 11/2015 | Arcilla et al. |
| 9,217,560 | B2 | 12/2015 | Harbers et al. |
| 9,283,295 | B2 | 3/2016 | Fink et al. |
| 9,295,746 | B2 | 3/2016 | Ellis |
| 9,308,289 | B2 | 4/2016 | Graff et al. |
| 9,327,048 | B2 | 5/2016 | Deane et al. |
| 9,365,884 | B2 | 6/2016 | Nishikawa et al. |
| 9,370,599 | B2 | 6/2016 | Deane et al. |
| 9,370,600 | B1 | 6/2016 | DuPuis et al. |
| 9,393,338 | B2 | 7/2016 | Livchak et al. |
| 9,394,191 | B2 | 7/2016 | Darwinkel et al. |
| 9,399,998 | B1 | 7/2016 | Hardie |
| 9,441,634 | B2 | 9/2016 | Spiro |
| 9,551,497 | B2 | 1/2017 | Waddell |
| 9,572,902 | B2 | 2/2017 | Nathan et al. |
| 9,579,424 | B2 | 2/2017 | Marra |
| 9,597,424 | B2 | 3/2017 | Gurman |
| 9,707,310 | B2 | 7/2017 | Watanabe et al. |
| 9,839,706 | B2 | 12/2017 | Anderson et al. |
| 9,839,714 | B2 | 12/2017 | Waddell et al. |
| 9,839,901 | B2 | 12/2017 | Ellis et al. |
| 9,843,169 | B2 | 12/2017 | Riskin et al. |
| 9,847,623 | B2 | 12/2017 | Sunshine |
| 9,849,208 | B2 | 12/2017 | Waddell |
| D811,574 | S | 2/2018 | McRoberts |
| 9,901,039 | B1 | 2/2018 | Dellerson et al. |
| 9,925,567 | B2 | 3/2018 | Waddell |
| 9,931,426 | B2 | 4/2018 | Ronda et al. |
| 9,937,274 | B2 | 4/2018 | Clynne et al. |
| 9,956,306 | B2 | 5/2018 | Brais et al. |
| 9,976,957 | B2 | 5/2018 | Kim et al. |
| 9,981,052 | B2 | 5/2018 | Clynne et al. |
| 9,987,499 | B2 | 6/2018 | Hayashi et al. |
| 10,006,619 | B1 | 6/2018 | Niemiec et al. |
| 10,012,375 | B1 | 7/2018 | Salessi |
| 10,020,180 | B2 | 7/2018 | Waddell |
| 10,046,075 | B2 | 8/2018 | Nathan et al. |
| 10,071,177 | B1 | 9/2018 | Kellogg, Jr. |
| 10,073,055 | B2 | 9/2018 | Waddell |
| 10,092,771 | B2 | 10/2018 | Varghese et al. |
| 10,101,051 | B2 | 10/2018 | Heller |
| 10,125,971 | B2 | 11/2018 | Graziano et al. |
| 10,128,075 | B2 | 11/2018 | Waddell |
| 10,139,060 | B1 | 11/2018 | Erdener et al. |
| 10,159,761 | B2 | 12/2018 | Kreitenberg |
| 10,195,298 | B2 | 2/2019 | Kreitenberg |
| 10,207,019 | B2 | 2/2019 | Takasahara et al. |
| 10,221,080 | B2 | 3/2019 | Boamfa et al. |
| 10,221,857 | B2 | 3/2019 | Niemiec et al. |
| 10,246,817 | B2 | 4/2019 | Wang et al. |
| 10,279,068 | B2 | 5/2019 | Eide et al. |
| 10,363,327 | B2 | 7/2019 | Liao et al. |
| 10,370,695 | B2 | 8/2019 | Kanhye |
| 10,393,399 | B2 | 8/2019 | Hilbig et al. |
| 10,406,253 | B2 | 9/2019 | Kreitenberg |
| 10,416,377 | B2 | 9/2019 | Girotto et al. |
| 10,439,370 | B2 | 10/2019 | Sunshine |
| 10,443,871 | B2 | 10/2019 | Agnaou et al. |
| 10,453,669 | B2 | 10/2019 | Ellis et al. |
| D868,233 | S | 11/2019 | Galbreath et al. |
| 10,463,759 | B2 | 11/2019 | Munn |
| 10,476,276 | B2 | 11/2019 | Amelio et al. |
| 10,498,099 | B2 | 12/2019 | Walker et al. |
| 10,500,296 | B2 | 12/2019 | Kreitenberg |
| 10,501,342 | B2 | 12/2019 | Hayashi et al. |
| 10,502,407 | B1 | 12/2019 | Spiro |
| 10,508,982 | B2 | 12/2019 | Koerber et al. |
| 10,514,139 | B2 | 12/2019 | Athalye |
| D875,046 | S | 2/2020 | Waddell |
| 10,556,025 | B2 | 2/2020 | Ufkes |
| 10,585,218 | B2 | 3/2020 | Ufkes et al. |
| 10,589,224 | B2 | 3/2020 | Verbakel et al. |
| 10,596,291 | B2 | 3/2020 | Van Der Graaf |
| 10,639,394 | B2 | 5/2020 | Munn |
| 10,670,026 | B2 | 6/2020 | Niemiec et al. |
| 10,677,446 | B2 | 6/2020 | Spiro |

(56) References Cited

U.S. PATENT DOCUMENTS

| | | |
|---|---|---|
| 10,705,005 B2 | 7/2020 | Qi et al. |
| 10,738,446 B1 | 8/2020 | Munn |
| 10,753,626 B2 | 8/2020 | Skelton |
| 10,772,980 B2 | 9/2020 | Stibich |
| 10,808,956 B2 | 10/2020 | Soyyigit |
| 10,808,964 B2 | 10/2020 | Polidoro |
| 10,897,806 B1 | 1/2021 | Bucher et al. |
| 10,987,440 B1 | 4/2021 | Sood et al. |
| 11,027,038 B1 | 6/2021 | Rhoades et al. |
| 11,060,712 B2 | 7/2021 | Niemiec et al. |
| 11,135,333 B1 | 10/2021 | Sood et al. |
| 11,160,890 B1 | 11/2021 | Lytle |
| 2003/0230477 A1 | 12/2003 | Fink et al. |
| 2005/0058584 A1 | 3/2005 | Shyu |
| 2005/0155366 A1 | 7/2005 | Kim et al. |
| 2007/0009363 A1 | 1/2007 | King |
| 2007/0111655 A1 | 5/2007 | Song et al. |
| 2008/0213129 A1 | 9/2008 | Van Der Pol et al. |
| 2009/0122572 A1 | 5/2009 | Page et al. |
| 2009/0129974 A1 | 5/2009 | McEllen |
| 2009/0169438 A1 | 7/2009 | Bruggink |
| 2009/0294342 A1 | 12/2009 | Bruggink et al. |
| 2010/0003164 A1 | 1/2010 | Bourne et al. |
| 2010/0181910 A1 | 7/2010 | Kessels |
| 2010/0284168 A1 | 11/2010 | Walter et al. |
| 2011/0104397 A1 | 5/2011 | Liao et al. |
| 2011/0286204 A1 | 11/2011 | Lord |
| 2012/0126134 A1 | 5/2012 | Deal et al. |
| 2012/0199005 A1 | 8/2012 | Koji et al. |
| 2012/0313014 A1 | 12/2012 | Stibich et al. |
| 2013/0119266 A1 | 5/2013 | Mondt et al. |
| 2013/0239803 A1 | 9/2013 | Palmer |
| 2013/0272879 A1 | 10/2013 | Chen |
| 2013/0291735 A1 | 11/2013 | Livchak et al. |
| 2013/0343052 A1 | 12/2013 | Yen |
| 2014/0198426 A1 | 7/2014 | Abate |
| 2015/0009666 A1 | 1/2015 | Keng et al. |
| 2015/0075371 A1 | 3/2015 | Abate |
| 2015/0110625 A1 | 4/2015 | De Siqueira Indio Da Costa et al. |
| 2015/0174426 A1 | 6/2015 | St. Germain et al. |
| 2016/0088868 A1 | 3/2016 | Dobrinsky et al. |
| 2016/0376170 A1 | 12/2016 | Ivan et al. |
| 2017/0080373 A1 | 3/2017 | Engelhard |
| 2017/0232132 A1 | 8/2017 | Deane et al. |
| 2017/0248148 A1 | 8/2017 | Kohen |
| 2017/0260681 A1 | 9/2017 | Gao et al. |
| 2017/0296686 A1 | 10/2017 | Cole |
| 2018/0055959 A1 | 3/2018 | Lin et al. |
| 2018/0065126 A1 | 3/2018 | Abate et al. |
| 2018/0072593 A1 | 3/2018 | Verschueren |
| 2018/0169279 A1 | 6/2018 | Randers-Pehrson et al. |
| 2018/0185530 A1 | 7/2018 | Ronda et al. |
| 2018/0236114 A1 | 8/2018 | Davis |
| 2018/0250428 A1 | 9/2018 | Canfield |
| 2018/0280558 A1 | 10/2018 | Mount |
| 2018/0339073 A1 | 11/2018 | Clynne et al. |
| 2019/0047877 A1 | 2/2019 | Geboers et al. |
| 2019/0091700 A1 | 3/2019 | Hilbig et al. |
| 2019/0104605 A1 | 4/2019 | Van Abeelen et al. |
| 2019/0125919 A1 | 5/2019 | Ellis et al. |
| 2019/0247862 A1 | 8/2019 | Galbreath et al. |
| 2019/0247893 A1 | 8/2019 | Waddell |
| 2019/0264702 A1 | 8/2019 | Huggins et al. |
| 2019/0275189 A1 | 9/2019 | Skelton |
| 2019/0280465 A1 | 9/2019 | Sunshine |
| 2019/0345946 A1 | 11/2019 | Register et al. |
| 2019/0353359 A1 | 11/2019 | Seibold |
| 2020/0009279 A1 | 1/2020 | Janssen |
| 2020/0016288 A1 | 1/2020 | Lalicki et al. |
| 2020/0038542 A1 | 2/2020 | Franklin et al. |
| 2020/0062622 A1 | 2/2020 | Linley et al. |
| 2020/0166235 A1 | 5/2020 | Marra et al. |
| 2020/0173646 A1 | 6/2020 | Marinus et al. |
| 2020/0179544 A1 | 6/2020 | Ufkes |
| 2020/0188544 A1 | 6/2020 | Ellis et al. |
| 2020/0197550 A1 | 6/2020 | Barron et al. |
| 2020/0254125 A1 | 8/2020 | Lloyd |
| 2020/0289686 A1 | 9/2020 | Janik et al. |
| 2020/0289698 A1 | 9/2020 | Polidoro |
| 2020/0332969 A1 | 10/2020 | Soler et al. |
| 2020/0340487 A1 | 10/2020 | Register et al. |
| 2020/0348038 A1 | 11/2020 | Risbeck et al. |
| 2020/0366125 A1 | 11/2020 | Chen |
| 2020/0393159 A1 | 12/2020 | Takayanagi |
| 2020/0408434 A1 | 12/2020 | Arentsen |
| 2021/0003317 A1 | 1/2021 | Polidoro |
| 2021/0016216 A1 | 1/2021 | Popa-Simil et al. |
| 2021/0219393 A1 | 7/2021 | Kerr et al. |
| 2021/0299318 A1 | 9/2021 | Mullen et al. |
| 2021/0388841 A1 | 12/2021 | Rhoades et al. |
| 2021/0388842 A1 | 12/2021 | Rhoades et al. |
| 2021/0388843 A1 | 12/2021 | Rhoades et al. |
| 2021/0388844 A1 | 12/2021 | Rhoades et al. |

FOREIGN PATENT DOCUMENTS

| | | |
|---|---|---|
| CN | 202266462 U | 6/2012 |
| CN | 103197659 A | 7/2013 |
| CN | 104154622 A | 11/2014 |
| CN | 104807111 A | 7/2015 |
| CN | 104949317 A | 9/2015 |
| CN | 105107631 A | 12/2015 |
| CN | 205090506 U | 3/2016 |
| CN | 205374368 U | 7/2016 |
| CN | 205446124 U | 8/2016 |
| CN | 106090836 A | 11/2016 |
| CN | 106152279 A | 11/2016 |
| CN | 106438420 A | 2/2017 |
| CN | 106610058 A | 5/2017 |
| CN | 106917765 A | 7/2017 |
| CN | 107181169 A | 9/2017 |
| CN | 107191398 A | 9/2017 |
| CN | 107196192 A | 9/2017 |
| CN | 206582820 U | 10/2017 |
| CN | 107388129 A | 11/2017 |
| CN | 107449073 A | 12/2017 |
| CN | 206947733 U | 1/2018 |
| CN | 107796094 A | 3/2018 |
| CN | 207094939 U | 3/2018 |
| CN | 207098267 U | 3/2018 |
| CN | 207218007 U | 4/2018 |
| CN | 108131616 A | 6/2018 |
| CN | 207962855 U | 10/2018 |
| CN | 208170554 U | 11/2018 |
| CN | 208170584 U | 11/2018 |
| CN | 208174004 U | 11/2018 |
| CN | 108980999 A | 12/2018 |
| CN | 208205238 U | 12/2018 |
| CN | 1090580136 A | 12/2018 |
| CN | 109137463 A | 1/2019 |
| CN | 208553675 U | 3/2019 |
| CN | 208674593 U | 3/2019 |
| CN | 109589441 A | 4/2019 |
| CN | 208885567 U | 5/2019 |
| CN | 110379514 A | 10/2019 |
| CN | 209926487 U | 1/2020 |
| CN | 209959513 U | 1/2020 |
| CN | 110748373 A | 2/2020 |
| CN | 111346247 A | 6/2020 |
| CN | 111388715 A | 7/2020 |
| CN | 111554409 A | 8/2020 |
| CN | 111561751 A | 8/2020 |
| CN | 211217848 A | 8/2020 |
| CN | 111637078 A | 9/2020 |
| CN | 111765530 A | 10/2020 |
| CN | 111811067 A | 10/2020 |
| CN | 111912044 A | 11/2020 |
| CN | 112161338 A | 1/2021 |
| DE | 2622749 A1 | 12/1977 |
| EP | 0409337 A1 | 1/1991 |
| EP | 1752715 A1 | 2/2007 |
| EP | 1870114 A1 | 12/2007 |
| EP | 2399614 A1 | 12/2011 |

(56) References Cited

FOREIGN PATENT DOCUMENTS

| | | |
|---|---|---|
| EP | 2646740 A2 | 10/2013 |
| EP | 2772272 | 9/2014 |
| EP | 2788680 A2 | 10/2014 |
| EP | 2881126 A1 | 6/2015 |
| EP | 2914858 A1 | 9/2015 |
| EP | 3043431 A1 | 7/2016 |
| EP | 3237857 A1 | 11/2017 |
| EP | 3331652 A1 | 6/2018 |
| EP | 3578886 A1 | 12/2019 |
| ES | 1249340 U | 7/2020 |
| FR | 2880950 A1 | 7/2006 |
| FR | 3048520 A1 | 9/2017 |
| GB | 546005 A | 6/1942 |
| GB | 2515842 A | 1/2015 |
| GB | 5254009 A | 9/2015 |
| GB | 5254116 A | 9/2015 |
| JP | 09314137 | 6/1942 |
| JP | 2005221217 A | 8/2005 |
| JP | 2007232323 A | 9/2007 |
| JP | 2007301117 A | 11/2007 |
| JP | 2014-162474 | 9/2014 |
| KR | 20010087720 A | 9/2001 |
| KR | 20030021396 A | 3/2003 |
| KR | 20040041266 A | 5/2004 |
| KR | 20070063968 A | 6/2007 |
| KR | 100838319 B1 | 6/2008 |
| KR | 20120079887 A | 7/2012 |
| KR | 20130125004 A | 11/2013 |
| KR | 101343401 B1 | 12/2013 |
| KR | 101526261 B1 | 6/2015 |
| KR | 101578044 B1 | 12/2015 |
| KR | 20160015084 A | 2/2016 |
| KR | 20190021656 A | 3/2019 |
| KR | 101962823 B1 | 7/2019 |
| KR | 20200004967 A | 1/2020 |
| KR | 102103022 B1 | 4/2020 |
| KR | 102192053 B1 | 12/2020 |
| TW | M596286 U | 6/2020 |
| WO | 19913922 A1 | 3/1999 |
| WO | 200212127 A2 | 2/2002 |
| WO | 2005031881 A2 | 4/2005 |
| WO | 2008117224 A1 | 10/2008 |
| WO | 2008139491 A2 | 11/2008 |
| WO | 2009104119 A2 | 8/2009 |
| WO | 2010131398 A1 | 11/2010 |
| WO | 2011013083 A1 | 2/2011 |
| WO | 2012069963 A1 | 5/2012 |
| WO | 2012071598 A2 | 6/2012 |
| WO | 2012120391 A1 | 9/2012 |
| WO | 2013036414 A1 | 3/2013 |
| WO | 2015110367 A1 | 7/2015 |
| WO | 2015132367 A1 | 9/2015 |
| WO | 2015132368 A1 | 9/2015 |
| WO | 2016077403 A1 | 5/2016 |
| WO | 2016105347 A1 | 6/2016 |
| WO | 2016200047 A1 | 12/2016 |
| WO | 2017021504 A1 | 2/2017 |
| WO | 2017055093 A1 | 4/2017 |
| WO | 2017144323 A1 | 8/2017 |
| WO | 2017152694 A1 | 9/2017 |
| WO | 2017162453 A1 | 9/2017 |
| WO | 2017211773 A1 | 12/2017 |
| WO | 2017216056 A1 | 12/2017 |
| WO | 2018060047 A1 | 4/2018 |
| WO | 2018065467 A1 | 4/2018 |
| WO | 2019045212 A1 | 3/2019 |
| WO | 2019081651 A1 | 5/2019 |
| WO | 2019091987 A1 | 5/2019 |
| WO | 2020050864 A1 | 3/2020 |
| WO | 2020113149 A1 | 6/2020 |
| WO | WO2020/203754 | 10/2020 |
| WO | 2021232000 A1 | 11/2021 |
| WO | WO2021/232000 | 11/2021 |
| WO | WO2021/257658 | 12/2021 |

OTHER PUBLICATIONS

"Advantages of Upper-Room GUV Germicidal UV Fixtures (E.G., Louvered)," Illuminating Engineering Society (IES) Webinar, Sep. 19, 2019.

"How Effective Is Upper Room UGVI," Illuminating Engineering Society (IES) Webinar, Sep. 19, 2019.

Edward N. Nardell et al., "Safety of Upper-Room Ultraviolet Germicidal Air Disinfection for Room Occupants," Tuberculosis Ultraviolet Shelter Study, Public Health Reports, Jan.-Feb. 2008, vol. 123, p. 52-60.

"A Fixed UV Disinfection Light, Helo is Perfect for Wherever People Gather," Puro Lighting, www.purolighting.com Retrieved Dec. 2020.

"Fail-Safe GUV Disinfecting Solutions: Germicidal UV (GUV) Technology," Cooper Lighting Solutions, LLC www.gecurrent.com Jan. 15, 2021.

"365 DisInFx Technology: Disinfection Lighting for Occupied Spaces: Air and Surface UV LED Solutions," Current Lighting Solutions, LLC, www.gecurrent.com Retrieved Dec. 2020.

"365 DisInFx LBU Series UVA Technology," Current Lighting Solutions, LLC, Retrieved Dec. 2020.

Livingston et al., "Efficacy of an Ultraviolet-A Lighting System for Continuous Decontamination of Health Care-Associated Pathogens on Surfaces," American Journal of Infection Control 48, pp. 337-339, Retrieved Dec. 2020.

"Signify," Signify Holding, www.signify.com Retrieved Dec. 2020. Philips UV-C Desk Lamp 8719514286108, Signify Holding, Retrieved Dec. 2020.

"UV Light Disinfection Technology," Acuity Lighting Brands, Inc., Retrieved Dec. 2020.

"Data Driven Disinfection: Safe. Simple. Validated.," SteriLumen, Greenwood Village, Colorado, Retrieved Dec. 2020.

"59s Global Leader UVC Disinfection," Shenzhen UVLED Optical Technology Co., Ltd., www.59s.com Retrieved Dec. 2020.

"Deep UV LED-275nm 3030 Series (CUD7QF1A) Product Brief," www.seoulviosys.com, Rev1.3, Nov. 25, 2020.

"The World's Favorite Ceiling Fan Safely Kills 99.9% of Airborne Pathogens," Delta T LLC, Jul. 10, 2020.

"Disinfect Your Home from Germs in an Effective and Easy Way," https://www.lighting.philips.com.sg/consumer/uv-c-lighting Signify Holding, Retrieved Dec. 2020.

Beatrice Casini et al., "Evaluation of an Ultraviolet C (UVC) Light-Emitting Device for Disinfection of High Touch Surfaces in Hospital Critical Areas," www.mdpi.com International Journal of Environmental Research and Public Health, Sep. 24, 2019.

M. Buonanno et al., "Far-UVC Light (222nm) Efficiently and Safely Inactivates Airborne Human Coronaviruses," Scientific Reports, vol. 10:10285, 2020.

"IALD Webinar on Lighting Design and GUV Technology," https://www.iald.org/Events/Global-Event-Calendar/Webinars/Lighting-Design-and-GUV-Technology, Aug. 2020.

M.E.R. Darnell et al., Inactivation of the Coronavirus that Induces Severe Acute Respiratory Syndrome, SARS-CoV, www.sciencedirect.com, Journal of Virological Methods 121 pp. 85-91, Jun. 2004.

"UV-C Aerosol," Innovative Bioanalysis Testing Report Product UVF7IN-120V-R1-MOD/UVF7IN-120V-R1, Innovative Bioanalysis LLC, 2020.

"UV-C Baseline," Innovative Bioanalysis Testing Report Product UVF7IN-120V-R1 With UF UVF7IN-120V-RI-MOD, Innovative Bioanalysis LLC, 2020.

T.P. Coohill et al., "Overview of the Inactivation by 254 nm Ultraviolet Radiation of Bacteria with Particular Relevance to Biodefense," Photochemistry' and Photobiology 84:1084-1090, 2008.

C.S. Heilingloh et al., "Susceptibility of SARS-CoV-2 to UV Irradiation," www.sciencedirect.com American Journal of Infection Control 48: 1273-1275, 2020.

T. Cutler et al., "Ultraviolet Irradiation and the Mechanisms Underlying its Inactivation of Infectious Agents," Animal Health Research Reviews 12(1) pp. 15-23, Jun. 2011.

(56) References Cited

OTHER PUBLICATIONS

D.K. Kim et al., "UVC LED Irradiation Effectively Inactivates Aerosolized Viruses, Bacteria, and Fungi in a Chamber-Type Air Disinfection System," Applied and Environmental Microbiology, vol. 84 Issue 17, Sep. 2018.
"UV Wall System Aerosol," Innovative Bioanalysis Testing Report Product WL345W UV Wall Mount, Innovative Bioanalysis LLC, 2020.
"UV Exposure Has Increased Over the Last 30 Years, but Stabilized Since Mid-1990's," www.nasa.gov Mar. 17, 2010.
"UV-C Photocarcinogenesis Risks From Germicidal Lamps," Oracle Lighting A.I.R. Industries LLC, Metaire, Louisiana, May 17, 2020.
"UV Lights and Lamps: Ultraviolet-C Radiation, Disinfection, and Coronavirus," www.fda.com, Feb. 1, 2021.
"365DisInFx: Disinfection Lighting for Occupied Spaces," Current Lighting Solutions, LLC, www.gecurrent.com, Apr. 2021.
"Delivering Peace of Mind that your Items are 100% Disinfected Against COVID," LiteSheet Solutions LLC, Nov. 5, 2020.
"Testing Shows 365DisInFx UVC Technology from GE Current, a Daintree Company, Helps Inactivate Airborne Viruses with LEDs," www.gecurrent.com Current Lighting Solutions, LLC, Dec. 14, 2020.
"DSX111 A-1029176 Spec Sheet: 365DisInFx LED Luminaries LDU Downlight with 365DisInFx UVA Technology—LDU Series," Current Lighting Solutions, LLC, www.gecurrent.com, Apr. 21, 2021.
"DSX101 A-1029014 Spec Sheet: 365DisInFx LED Luminaries LPU Series—365DisInFx Puck UVC," Current Lighting Solutions, LLC, www.gecurrent.com, Feb. 22, 2021.
"Klaran WD Series UVC LEDs: Data Sheet," www.klaran.com, Crystal IS, Inc., 2020.
"Haiku UV-C Fan Instruction," Delta T LLC, 2020.
"IES Committee Report: Germicidal Ultraviolet (GUV)-Frequently Asked Questions," Illuminating Engineering Society, May 5, 2020.
Ko et al., "The Characterization of Upper-Room Ultraviolet Germicidal Irradiation in Inactivating Airborne Microorganisms," Environmental Health Perspectives, vol. 110 No. 1, Jan. 2002.
Nicholas G. Reed, "The History of Ultraviolet Germicidal Irradiation for Air Disinfection," Public Health Reports, vol. 125, Jan.-Feb. 2010.
Nardell et al., "Airborne Spread of SARS-CoV-2 and a Potential Role for Air Disinfection," https://jamanetwork.com/journals/jama/fullarticle/2766821, Jun. 1, 2020.
Bergman et al., "Germicidal Ultraviolet Disinfection in the Days of COVID-19," Committee Reports—Illuminating Engineering Society (ies.org), Illuminating Engineering Society, May 7, 2020. (Linked document not downloadable by applicant.).
Sliney et al. "Introduction to Ultraviolet and Visible Radiation Disinfection," Committee Reports—Illuminating Engineering Society (ies.org), Illumination Engineering Society, Sep. 19, 2019. (Linked document not downloadable by applicant.).
App No. PCT/US2021/32200 International Search Report and Written Opinion of the International Searching Authority, dated Sep. 24, 2021.
Dhakal et al., "Seismic Fragility of Suspended Ceiling Systems Used in NZ Based on Component Tests," Bulletin of the New Zealand Society for Earthquake Engineering, vol. 49, No. 1, Mar. 2016.
"Torch Ceiling Fan," Fanimation, 2018.
U.S. Appl. No. 63/025,501, dated May 15, 2020, Lesser.
U.S. Appl. No. 63/039,788, filed Jun. 16, 2020, Rhoades et al.
U.S. Appl. No. 63/040,274, filed Jun. 17, 2020, Rhoades et al.
U.S. Appl. No. 63/054,871, filed Jul. 22, 2020, Rhoades et al.
U.S. Appl. No. 63/123,595, filed Dec. 10, 2020, Rhoades et al.
LEDs Magazine, Mark Halper, "UV-C LEDs fan out in air circulation offerings", USA, Dec. 4, 2020, available at https://www.ledsmagazine.com/lighting-healthwellbeing/article/14188485/uvc-leds-fan-ut-in-air-circulation-offerings.
Crystal IS, Inc., "Big Ass Fans Case Study", Green Island, NY, Jan. 12, 2021, available at https://klaran.com/big-ass-fans-case-study.
Cnet.com (video stills), "UV light and the coronavirus: Big Ass Fans might have a solution", Aug. 6, 2020, available at https://www.cnet.com/home/smart-home/uv-light-and-the-coronavirus-bigass-fans-might-have-a-solution-haiku-uvc-covid-19/
Digitized House, Tom Kolnowski, "Big Ass Fans to Launch Haiku UV-C Fan With Germicidal Feature", Jun. 23, 2020, aviable at https://digitized.house/big-ass-fans-to-launch-haiku-uv-c-fan-withgermicidal-feature/.
CNBC, (stills from video), "Company claims these fans can kill Covid in the air through UV light and ion technology", Nov. 16, 2020, available at https://www.cnbc.com/video/2020/11/16/company-claims-these-fans-cankill-covid-in-the-air-through-uv-light-and-ion-technology.html.
Delta T LLC, "Air-disinfection", (screenshot), USA Sep. 20, 2020, available at https://web.archive.org/web/20200920152749/https://www.bigassfans.com/air-disinfection/.
Delta T LLC, "Haiku With UV-C Technology: Technical Specifications", Jun. 3, 2021.
Delta T LLC, "Essence With UV-C Technology: Technical Specifications", Sep. 30, 2021.
Delta T LLC, "Quick Installation Guide: Essence with UV-C Technology", Jul. 27, 2021.
Delta T LLC, "UV-C LED Board Replacement: Essence with UV-C Technology", Apr. 30, 2021.
Delta LLC, "Haiku with UV-C Technology: UV-C with LED Board Replacement:" Aug. 19, 2020.
Delta T LLC, "Products with UV-C Technology: Commercial/Residential Applications," (screenshot created Jan. 4, 2022).

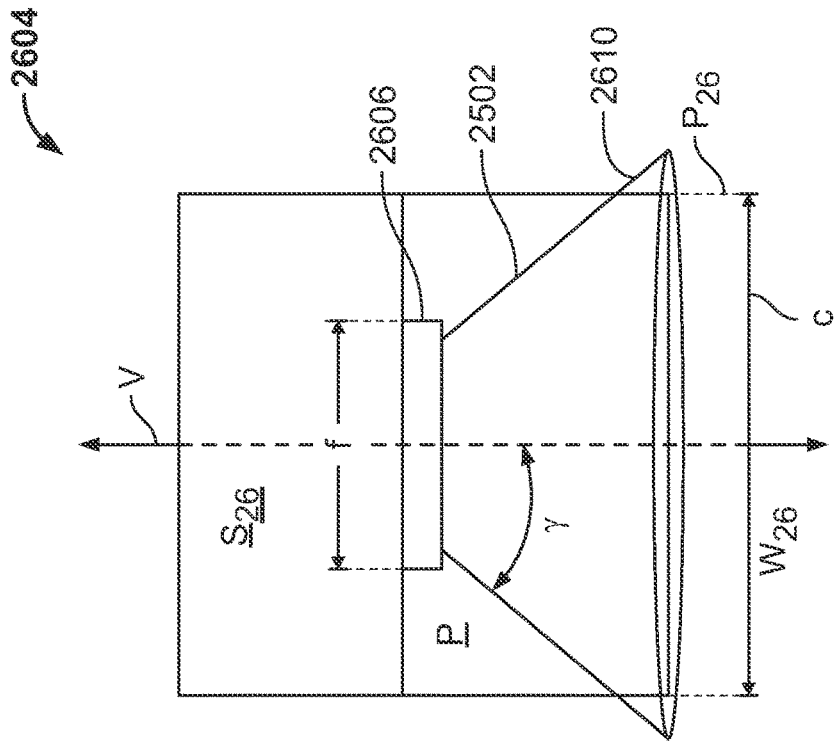
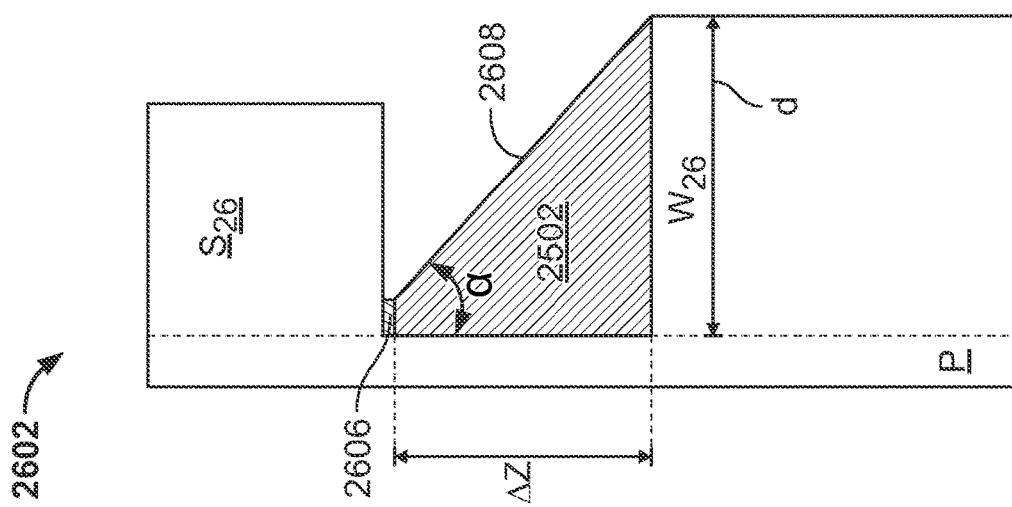
FIG. 26

GERMICIDAL LIGHTING

CROSS-REFERENCE TO RELATED APPLICATIONS

This is a continuation of co-pending U.S. patent application Ser. No. 17/319,432, filed on May 13, 2021, which is a nonprovisional of U.S. Provisional Applications Nos. 63/026,702, filed May 18, 2020, and 63/027,315, filed May 19, 2020, all of which are hereby incorporated by reference in their entireties. This application claims the benefit of priority under 35 U.S.C. 119(a) of commonly owned P.R.C. Application No. 202120548631.2, filed Mar. 17, 2021, which is hereby incorporated by reference herein in its entirety.

BACKGROUND

Typically, fixtures that include lights are fitted with lights that illuminate space that is occupied by living beings or sensitive items. Pathogen reduction or elimination in such a space has become desirable. Emission from fixtures of pathogen-killing light or other energy may be desired. However, pathogen-killing light may be incompatible with the use of the space by the living beings or for the sensitive items.

It would therefore be desirable to provide apparatus and methods for providing the light or other energy from a fixture in a manner that provides safety for the living beings or the sensitive items.

BRIEF DESCRIPTIONS OF THE DRAWINGS

The objects and advantages of the invention will be apparent upon consideration of the following detailed description, taken in conjunction with the accompanying drawings, in which like reference characters refer to like parts throughout, and in which:

FIG. 26 shows schematically illustrative apparatus in accordance with principles of the invention.

Figure 1:
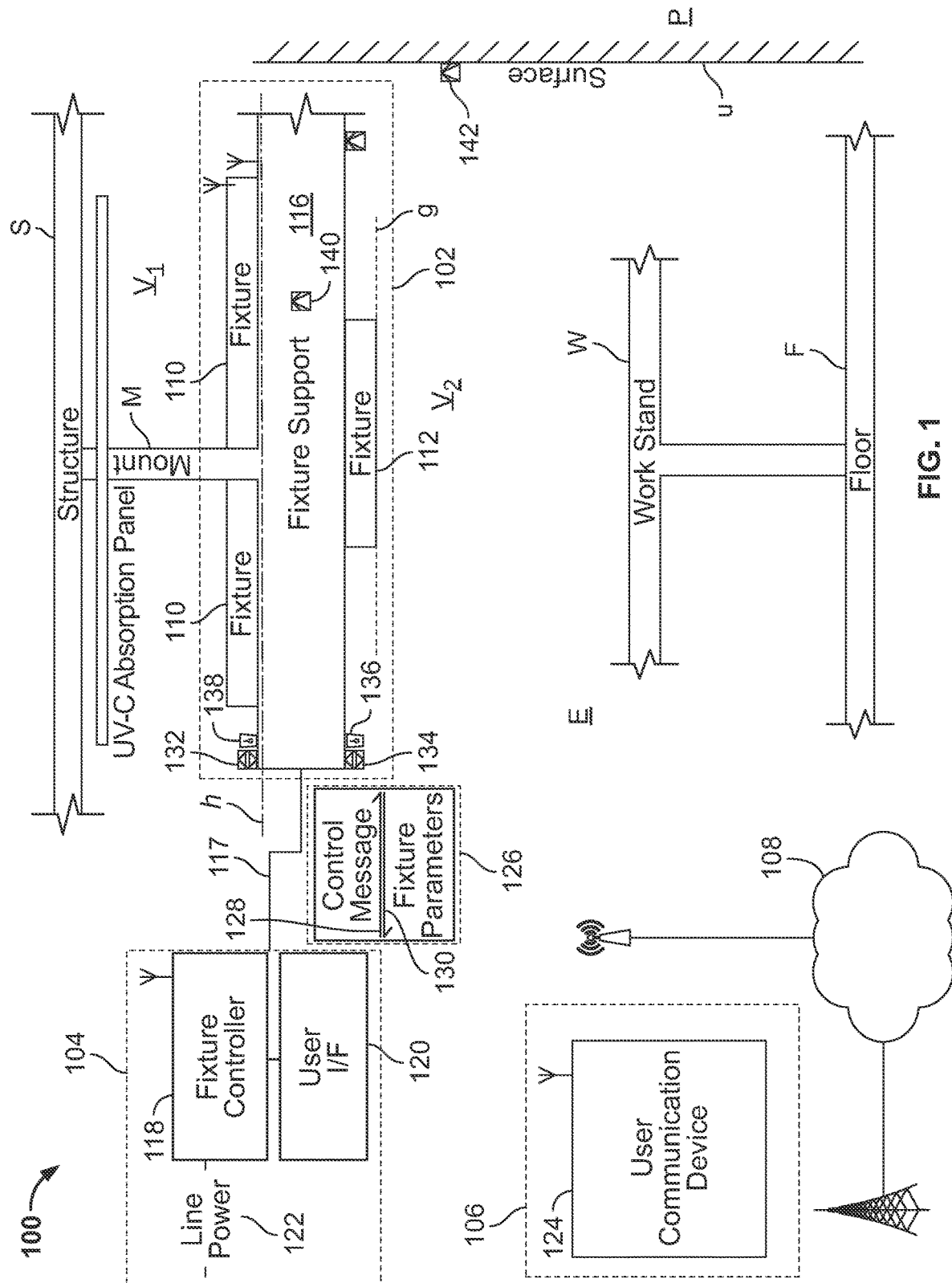
FIG. 1 shows illustrative apparatus in accordance with principles of the invention.

The leftmost digit (e.g., "L") of a three-digit reference numeral (e.g., "LRR"), and the two leftmost digits (e.g., "LL") of a four-digit reference numeral (e.g., "LLRR"), generally identify the first figure in which a part is called-out.

DETAILED DESCRIPTION

Apparatus, methods and algorithms for disinfecting air and surfaces are provided. The methods may involve the apparatus. The methods may involve the algorithms. The algorithms may include instructions.

The apparatus may include a support. The support may be configured to be suspended from a structure. The structure may be a ceiling, a drop ceiling frame, a wall, a joist, a beam, a stud, a frame or any other suitable structure.

The apparatus may include a germicidal energy source. The energy source may include an emitter. The emitter may include an ionizing energy source. The emitter may include a light-emitting diode ("LED").

The energy source may include a light source. The light source may include the emitter.

The light source may be supported by the support. The light source may be configured to emit, upward from a horizontal plane, a beam that, absent reflection off an environmental object, does not cross the horizontal plane.

The apparatus may include a shield that prevents light from the light source from crossing the horizontal plane.

The light source may be configured to neutralize a virion. The light source may be configured to neutralize a bacterium. The light source may be configured to neutralize a fungus.

The light source may be disposed in a fixture that may be configured to direct the beam. Table 1 lists illustrative fixtures.

TABLE 1

Illustrative fixtures

Light
Fan
Audio speaker
Audio/Video projector
Camera
Sensor
Other suitable fixtures The fixture may include one or more devices. Table 2 lists illustrative devices.

TABLE 2

Illustrative devices

LED
Switch
Electro-acoustic transducer
Video display
Microphone
Motor
Linear actuator
Antenna
RF transmitter
RF receiver
Transponder
Motion sensor
Ionizing electrodes
Light sensor
Other suitable devices The fixture may intersect the horizontal plane.

The light source may include an array of light emitting diodes. The array may intersect the horizontal plane.

A diode may face upward. A diode may face horizontally. A diode may be canted at an angle between the upward direction and the vertical direction. A diode may face downward.

The light source may include a light tape. The array may define the horizontal plane.

The light source may be embedded in a chip. The horizontal plane may be coincident with a surface of the chip.

The light source may include an emitter that emits light having a wavelength that may be no longer than that of ultraviolet light.

The wavelength may be in the UV-A spectrum. The wavelength may be in the UV-B spectrum. The wavelength may be in the UV-C spectrum. The wavelength may be bactericidal. The wavelength may be virucidal. The wavelength may be fungicidal. The wavelength may be 275 nm. Table 3 lists illustrative ranges that may include a germicidal wavelength.

TABLE 3

Illustrative ranges that may include a germicidal wavelength

| Range | |
| --- | --- |
| Lower | Upper |
| <250 | 255 |
| 255 | 260 |
| 260 | 265 |
| 265 | 270 |
| 270 | 275 |
| 275 | 280 |
| 280 | 285 |
| 285 | 290 |
| 290 | 295 |
| 295 | 300 |
| 300 | 305 |
| 305 | >310 |

Other suitable ranges that may include a germicidal wavelength

The germicidal wavelength may be produced by an emitter such as a 3030 series (CUD7QF1A) UV-C emitter, available from Seoul Viosys (www.seoulviosys.com).

The light source may be configured to disinfect air above the horizontal plane. The air may be flowing relative to the light source. The air may be in circulation about a room.

The light source may include an array of light-emitting diodes. The array may be circular, polyhedral, or may have any other suitable shape.

The shield may surround the array.

The apparatus may include a controller. The controller may be configured to control the light source.

The controller may be configured to deliver to the air a selected amount of energy.

The selected amount of energy may be based on a volume of the air. The selected amount of energy may be based on a flow rate of the air.

The apparatus may include one or more sensors. A sensor may be configured to sense or detect a characteristic or condition in an environment. The sensor may be mounted on a swivel-based. The user may select the orientation of the sensor by moving the sensor relative to the swivel base.

The sensor may face radially away from a plumb direction that runs through the fixture in which the light source is disposed.

The apparatus may include a range sensor configured to estimate a distance between the horizontal plane and a structure below which the support may be suspended. The structure may be a ceiling. The apparatus may include a "workspace" light. The workspace light may include a housing of extruded aluminum.

The emitter may have a beam spread. The beam spread and the distance may define a beam volume. The controller may be configured to estimate the beam volume. The beam volume may be defined by: an inner beam angle; an outer beam angle; and a distance to the support. A captive volume may be defined by a product of: a horizontal dimension of a fan and the distance to the support. The captive volume may be a "target zone." The horizontal dimension may be an area swept out by a fan blade in a revolution about the support. The horizontal dimension may be any other suitable horizontal dimension of the fixture. The beam volume may include space occupied by the fixture itself, such as mount M. The beam volume may exclude space occupied by the fixture itself, such as mount M. The captive volume may include space occupied by the fixture itself, such as mount M. The captive volume may exclude space occupied by the fixture itself, such as mount M. A treatment volume ratio may be defined as the ratio of the beam volume to the captive volume.

The blade may induce vertical circulation in environment E. The vertical circulation may bring air from different levels in environment E into the captive volume. The blade may induce horizontal circulation through the captive volume. The blade may induce vertical circulation through the captive volume. The blade may induce mixed vertical and horizontal circulation through the captive volume. The blade may induce mixing in the captive volume.

Table 4 lists illustrative values of treatment volume ratios.

TABLE 4

Illustrative treatment strengths ($V_{beam}:V_{captive}$)

| Lower | Upper |
|---|---|
| 0.50 | 0.55 |
| 0.55 | 0.60 |
| 0.60 | 0.65 |
| 0.65 | 0.70 |
| 0.70 | 0.75 |
| 0.75 | 0.80 |
| 0.80 | 0.85 |
| 0.85 | 0.90 |
| 0.90 | 0.95 |
| 0.95 | 1.00 |
| 1.00 | 1.05 |
| 1.05 | 1.10 |
| 1.10 | 1.15 |
| 1.15 | 1.2 |
| 1.2 | >1.2 |
| Other suitable lower limits | Other suitable upper limits |

The apparatus may include a velocity-measuring instrument. The velocity-measuring instrument may be used to estimate an exchange rate of the air in the captive volume. The amount of energy may be based on the captive volume and the exchange rate.

The apparatus may include an LED driver circuit. The LED driver circuit may be configured to adjust a duration ("ON-time") of the energy.

The LED driver circuit may be configured to adjust a frequency of the energy.

The LED driver circuit may be configured to adjust an intensity of the energy.

A beam intensity may be selected to deliver a predetermined energy to the beam volume. A beam intensity may be selected to deliver a predetermined energy to the captive volume. A beam intensity may be selected to cause a predetermined areal energy density at the distance.

The apparatus may include a sensor that is configured to detect a presence of a living body. The sensor may be a motion sensor. The controller may be configured to change a beam characteristic of the light source in response to detection of the living body by the sensor. The beam characteristic may be a fixture parameter. The fixture may power OFF the beam in response to the motion.

The living body may be a person.

The apparatus may include a fan blade. The fan blade may be configured to revolve about the support. The apparatus may include a microprocessor. The motion sensor may be configured to detect a first electromagnetic signal. The microprocessor may be configured to subtract from the first electromagnetic signal a second electromagnetic signal caused by the fan blade.

The microprocessor may be programmable.

The apparatus may include a microcontroller. The microcontroller may be programmable.

The motion sensor may face upward from the horizontal plane.

The motion sensor may face downward from the horizontal plane.

The apparatus may include a motion sensor. The motion sensor may be configured to detect a reflection of light from the light source from a structure.

The structure may be a ceiling.

The structure may be a wall.

The structure may be a structure that extends vertically at a horizontal distance from the light source.

The controller may be configured to change a beam characteristic of the light source in response to the reflection.

The characteristic may be energy emission.

The characteristic may be energy intensity.

The light source may be disposed in the fixture; and the fixture may support a louver that may be configured to direct the beam.

The fixture may include a motor that is configured to adjust an attitude (angle) of the louver. The fixture may include a motor-control. The motor control may be configured to control the motor. The motor control may be configured to receive from the controller an instruction to adjust the attitude.

The fixture may include a motor that is configured to adjust a vertical position of the louver. The fixture may include a motor-control. The motor control may be configured to control the motor. The motor control may be configured to receive from the controller an instruction to adjust the vertical position.

The louver may have opaque walls. The louver may have an opaque top. The louver may block laterally-directed radiation propagating from the array. The louver may block vertically-directed radiation propagating from the array.

The apparatus may include a stray-light sensing circuit. The stray-light sensing circuit may be configured to sense, outside the captive volume, light from the light source. The stray-light sensing circuit may be configured to responsively transmit a signal to the controller to prompt the instruction.

The support may support the circuit.

The light source may be disposed in a fixture; and the fixture may support a reflector that may be configured to direct the beam.

The fixture may include a motor. The motor may be configured to adjust an attitude of the reflector. The fixture may include a motor control. The motor-control may be configured to control the motor. The motor-control may be configured to receive from the controller an instruction to adjust the attitude.

The apparatus may include a stray-light sensing circuit. The stray-light sensing circuit may be configured to sense, outside the captive volume, light from the light source. The stray-light sensing circuit may be configured to responsively transmit a signal to the controller to prompt the instruction.

The support may support the circuit.

The apparatus may include a range sensor. The range sensor may be configured to estimate a distance below the horizontal plane and above a floor above which the support may be suspended. The controller may be configured to change the beam characteristic of the light source in response to the distance.

The apparatus may include lensing disposed over the light source.

The lensing may have UV-C transmissivity in a range. Table 5 lists illustrative ranges of transmissivity.

TABLE 5

Illustrative ranges of transmissivity

| Lower | Upper |
|---|---|
| 0.50 | 0.55 |
| 0.55 | 0.60 |
| 0.60 | 0.65 |
| 0.65 | 0.70 |
| 0.70 | 0.75 |
| 0.75 | 0.80 |
| 0.80 | 0.85 |
| 0.85 | 0.90 |
| 0.90 | 0.95 |
| 0.95 | >0.95 |
| Other suitable lower limits | Other suitable upper limits |

The apparatus may include a housing. The apparatus may include a liquid-tight seal. The light source may be disposed in the housing. The seal may seal between the lensing and the housing.

The apparatus may include a coating. The coating may be disposed on a surface of the lensing.

The apparatus may include a motor. The motor may be configured to adjust a distance between the light source and the lensing to change a beam angle of the beam.

The apparatus may include a control interface in electronic communication with the controller. The control interface may be configured to receive an instruction conforming to a lighting control protocol.

Table 6 lists illustrative protocols.

TABLE 6

Illustrative control protocols

DMX
DALI
Triac
0-10 Volt variable voltage
Custom-user defined
Default-provided in memory
Other suitable third party control protocol The control interface may be configured to override the instruction when the instruction is configured to reduce an amount of energy emitted from the light source.

The apparatus may include a circuit that may be configured to provide to the light source a predetermined amount of power when the instruction is configured to reduce an amount of energy emitted from the light source.

The apparatus may include, when the circuit is a first circuit, a second circuit that may be configured to provide power to the light circuit subject to the instruction.

The first circuit may be parallel the second circuit.

The first circuit may be in serial connection with the second circuit.

The light source may be powered by a line voltage. The first circuit may have a first source of power drawn from the line voltage. The second circuit may have a second source of power drawn from the line voltage. The first source of power may be distinct from the second source of power.

The apparatus may include a fan supported by the support. The fan may be operative to flow room air through the beam. The fan may be operable in an updraft mode. In the updraft mode, the fan may draw room air up from a lower region of a room. The fan may be operable in a downdraft mode. In the downdraft mode, the fan may force room air down from an upper region of a room. The microprocessor may be configured to adjust the light source to provide a level of disinfecting energy that is correlated with a setting of the fan. The setting may be a speed setting. The setting may be a direction setting.

The apparatus may include, and the methods and instructions may involve, the germicidal light source. The germicidal light source may be configured to be supported by a support suspended below a ceiling. The germicidal light source may be configured to emit, upward from a horizontal plane, a beam that, absent reflection off an environmental object, does not cross the horizontal plane.

The germicidal energy source may be supported by the support. The germicidal energy source may be configured to emit into the air germicidal energy. A fan blade may cause relative motion of the air with respect to the energy source.

The germicidal energy source may include a cathode. The germicidal energy source may include an anode. The germicidal energy may be transmitted in an electrical field established between the cathode and the anode.

The apparatus may include a rotatable electrical power contact. The contact may be configured to rotate about the axis. The contact may include a brush. The contact may be configured to receive electrical power from a conductor rotationally fixed to the support. The contact may be configured to provide the electrical power to the emitter. The emitter may be fixed to the blade. The emitter may be fixed to a top of the blade. The emitter may be fixed to a bottom of the blade.

The energy may have an intensity that is sufficient to ionize a gas molecule. The gas molecule may include oxygen. The gas molecule may include nitrogen.

The apparatus may include the support configured to be suspended from a structure; a germicidal light source and the fixture. The support may support the fixture. The support may support the light source. The fixture may direct a beam from the light source to a zone below the support.

The apparatus may include a light absorption panel. The panel may be disposed to prevent light from illuminating a structure. The panel may be disposed to prevent light from illuminating a surface. The panel may be disposed to prevent light from reaching a structure from which the light might reflect to a location outside the captive volume. The panel may be disposed to prevent light from reaching a surface from which the light might reflect to a location outside the captive volume.

The germicidal light source may be configured to neutralize a virion. The germicidal light source may be configured to neutralize a bacterium. The light source may be disposed in a fixture that may be configured to direct the beam.

The light source may include an emitter that emits light having a wavelength that is no longer than ultraviolet. The wavelength may be in the UV-A spectrum. The wavelength may be in the UV-B spectrum. The wavelength may be in the UV-C spectrum.

The light source may be configured to disinfect a surface of an object in the zone.

The light source may include a circular array of light-emitting diodes.

The apparatus may include a controller that may be configured to control the beam. The controller may be configured to control the light source. The controller may be configured to control the fixture in which the light source is disposed. The controller may be configured to cause the light source to emit to the captive volume or the beam volume a selected amount of energy.

The selected amount of energy may be selectable by a user.

The controller may be configured to adjust a duration of emission of the energy. The controller may be configured to adjust a frequency of the energy. The controller may be configured to adjust an intensity of the energy.

The controller may be configured to change a beam characteristic of the light source in response to a detection by the motion sensor. The motion sensor may be mounted in a user-selected location.

The sensor may be a photosensor. The photosensor may be configured to detect a reflection of light from the light source from a structure. The structure may be a ceiling. The structure may be a wall. The structure may be a structure that extends vertically at a horizontal distance from the light source.

The controller may be configured to change a beam characteristic of the light source in response to the reflection. The characteristic may be energy emission. The characteristic may be energy intensity.

The light source may be disposed in the fixture; and the fixture may support a louver that may be configured to direct the beam.

The fixture may include a motor that is configured to adjust an attitude of the louver. The fixture may include a motor-control. The motor control may be configured to control the motor. The motor control may be configured to receive from the controller an instruction to adjust the attitude.

The apparatus may include a stray-light sensing circuit. The stray-light sensing circuit may be configured to sense, outside the captive volume, light from the light source. The stray-light sensing circuit may be configured to responsively transmit a signal to the controller to prompt the instruction.

The support may support the circuit.

The light source may be disposed in a fixture; and the fixture may support a reflector that may be configured to direct the beam.

The fixture may include a motor. The motor may be configured to adjust an attitude of the reflector. The fixture may include a motor control. The motor-control may be configured to control the motor. The motor-control may be configured to receive from the controller an instruction to adjust the attitude.

The apparatus may include a stray-light sensing circuit. The stray-light sensing circuit may be configured to sense, outside the zone, light from the light source. The stray-light sensing circuit may be configured to responsively transmit a signal to the controller to prompt the instruction.

The apparatus may include lensing disposed over the light source.

The lensing may have UV-C transmissivity.

The apparatus may include a housing. The apparatus may include a liquid-tight seal. The light source may be disposed in the housing. The seal may seal between the lensing and the housing.

The apparatus may include a coating disposed on a surface of the lensing.

The apparatus may include a motor configured to adjust a distance between the light source and the lensing to change a beam angle of the beam.

The apparatus may include a control interface in electronic communication with the controller. The control interface may be configured to receive an instruction conforming to a lighting control protocol. The control interface may be configured to override the instruction when the instruction is configured to reduce an amount of energy emitted from the light source.

The apparatus may include a circuit that may be configured to provide to the light source a predetermined amount of power when the instruction is configured to reduce an amount of energy emitted from the light source.

The circuit may be a first circuit. The apparatus may include a second circuit that may be configured to provide power to the light source subject to the instruction. The first circuit may be parallel the second circuit. The first circuit may be in serial connection with the second circuit.

The light source may be powered by a line voltage. The first circuit may have a first source of power drawn from the line voltage. The second circuit may have a second source of power drawn from the line voltage. The first source of power may be distinct from the second source of power.

The fixture may include a visible light emitter. The visible light emitter may emit one or more colored lights to signal to signal to the user a status of the fixture. For example, Yellow: "A germicidal feature of the fixture is about to turn on (after delay time)." Red: one or both of (1) "A germicidal feature of the fixture will turn on in X seconds," where X=a predetermined number of seconds between 0.1 and 60, or any other suitable number; and (2) "A germicidal feature of the fixture is currently on." Green: "A disinfection cycle has been completed." X may be user-selected. X may be shorter than the delay time.

The light source may include a user-cuttable light tape.

Illustrative embodiments of apparatus and methods in accordance with the principles of the invention will now be described with reference to the accompanying drawings, which forma part hereof. It is to be understood that other embodiments may be utilized and that structural, functional and procedural modifications or omissions may be made without departing from the scope and spirit of the present invention.

FIG. 1 shows illustrative architecture 100 for providing germicidal light. Architecture 100 may include fixture arrangement 102. Architecture 100 may include fixture control module 104. Architecture 100 may include inputs 106. Architecture 100 may include wide area network 108. Architecture 100 may include one or more fixtures such as fixtures 110 and 112.

Communication between fixture arrangement 102 and fixture control module 104 may be wired. Communication between fixture arrangement 102 and fixture control module 104 may be wireless. Communication between fixture control module 104 and inputs 106 may be wired. Communication between fixture control module 104 and inputs 106 may be wireless.

Fixture arrangement 102 may be disposed in or near environment E. Environment E may be an indoor environment. Environment E may be an outdoor environment. Environment E may include one or more elements, such as work stand W, floor F, partition P, surface U of partition P, and structure S, or other suitable elements. Table 7 lists illustrative work stands.

TABLE 7

Illustrative work stands

Counter top
Table top
Storage shelves
Work bench
Work stand
Work space surface
Kitchen countertop
Work bench
Sink
Closet shelf
Closet garment rack
Other suitable work stands Environment E may include captive volume $V_1$, above horizontal plane h. Environment E may include captive volume $V_2$, above horizontal plane h, and captive volume $V_2$, below horizontal plane g.

Control module 104 may be disposed apart from fixture arrangement 102. Fixture control module 104 may disposed in or on fixture arrangement 102. Fixture control module 104 may be disposed in or on a fixture of fixture arrangement 102.

Fixture arrangement 102 may include fixture support 116. Fixture arrangement 102 may be supported by mount M. Mount M may fix fixture support 116 to structure S. Structure S may include a ceiling, a wall, a beam, cabinet, a free-standing object or any other suitable structure. h shows a level of a horizontal plane. Fixture support 116 may support one or more fixtures such as fixtures 110 and 112. One or more of the fixtures may be disposed on top of fixture support 116. One or more of the fixtures may be disposed on bottom of fixture support 116. One or more of the fixtures may be disposed on a side of fixture support 116. One or more of the fixtures may be disposed on an end of fixture support 116.

Architecture 100 may include one or more sensors. The sensors may include a range sensor such as 132 and 134. The range sensor may sense a distance to a surface. The sensors may include a temperature sensor such as 136 and 138. The temperature sensor may sense an ambient temperature. The temperature sensor may sense a temperature or a differential temperature of a surface at a distance from the sensor. The sensors may include a motion sensors such as 140 and 142. The sensors may include one or more light sensors (not shown). The light sensor may sense visible light. The light sensor may sense UV light. Architecture 100 may include one or more sources of ionizing energy.

Fixture control module 104 may include fixture controller 118. Fixture control module 104 may include user interface 120. Fixture controller 118 may be in electrical communication with line power 122. Line power 122 may provide two-phase or three-phase power at 110 V or 220 V, DC voltage at any suitable level, or any other suitable voltage. Fixture controller 118 may include a battery (not shown).

Input 106 may include user communication device 124. Table 8 lists illustrative user communication devices.

TABLE 8

Illustrative user communication devices

Mobile phone
Tablet
PC
Remote control
Dimmer switch
Power switch
Other suitable user communication devices Fixture controller 118 may be in wired electrical communication with fixtures of fixture arrangement 102. The wired electrical communication may be provided by cable 117. The wired electrical communication may provide power to with fixtures of fixture arrangement 102. The wired electrical communication may provide for exchange of information 126 with fixtures of fixture arrangement 102. Fixture controller 118 may provide the power and the information over different conductors. Fixture controller 118 may provide the power and the information simultaneously over a conductor, as is done in power line control methods.

Information 126 may include control messages 128.

Table 9 lists illustrative control messages.

TABLE 9

Illustrative control messages

Change beam spread angle
Change beam edge angle (inner radius of annular array)
Change beam edge angle (outer radius of annular array)
Change beam tilt relative to vertical axis
Power ON-germicidal and marker light
Power ON Delay-germicidal and marker light
Power ON Duration-germicidal and marker light
Power OFF-visible light
Power ON- visible light
Set Power ON Delay- visible light
Set Power ON Duration- visible light
Power OFF- visible light
Other suitable control messages Information 126 may include fixture parameters 130.

Table 10 lists illustrative fixture parameters.

TABLE 10

Illustrative fixture parameters

Beam spread angle
Beam edge angle (inner radius of annular array)
Beam edge angle (outer radius of annular array)
Beam longitude relative to vertical axis
Power ON-germicidal and marker light
Power ON Delay-germicidal and marker light
Power ON Duration-germicidal and marker light
Power OFF-visible light
Power ON- visible light
Power ON Delay- visible light
Power ON Duration- visible light TABLE 10-continued Illustrative fixture parameters Power OFF- visible light
Combination of any of the above
Other suitable fixture parameters Fixture control module 104 may be in communication with input 106.

A user may input a user command to user interface 120. Table 11 lists illustrative user commands.

TABLE 11

Illustrative user commands

Power ON
Power OFF
Set fan speed
Set visible light intensity
Power ON-germicidal and marker light
Power ON Delay-germicidal and marker light
Power ON Duration-germicidal and marker light
Power OFF-visible light
Power ON- visible light
Set Power ON Delay- visible light
Set Power ON Duration- visible light
Power OFF- visible light
Reset a fixture parameter
Other suitable user commands User interface 120 may include a data input device. The data input device may include one or more of a touch screen, a key pad and any other suitable device.

The user may input the user command from user communication device 124.

Figure 2:
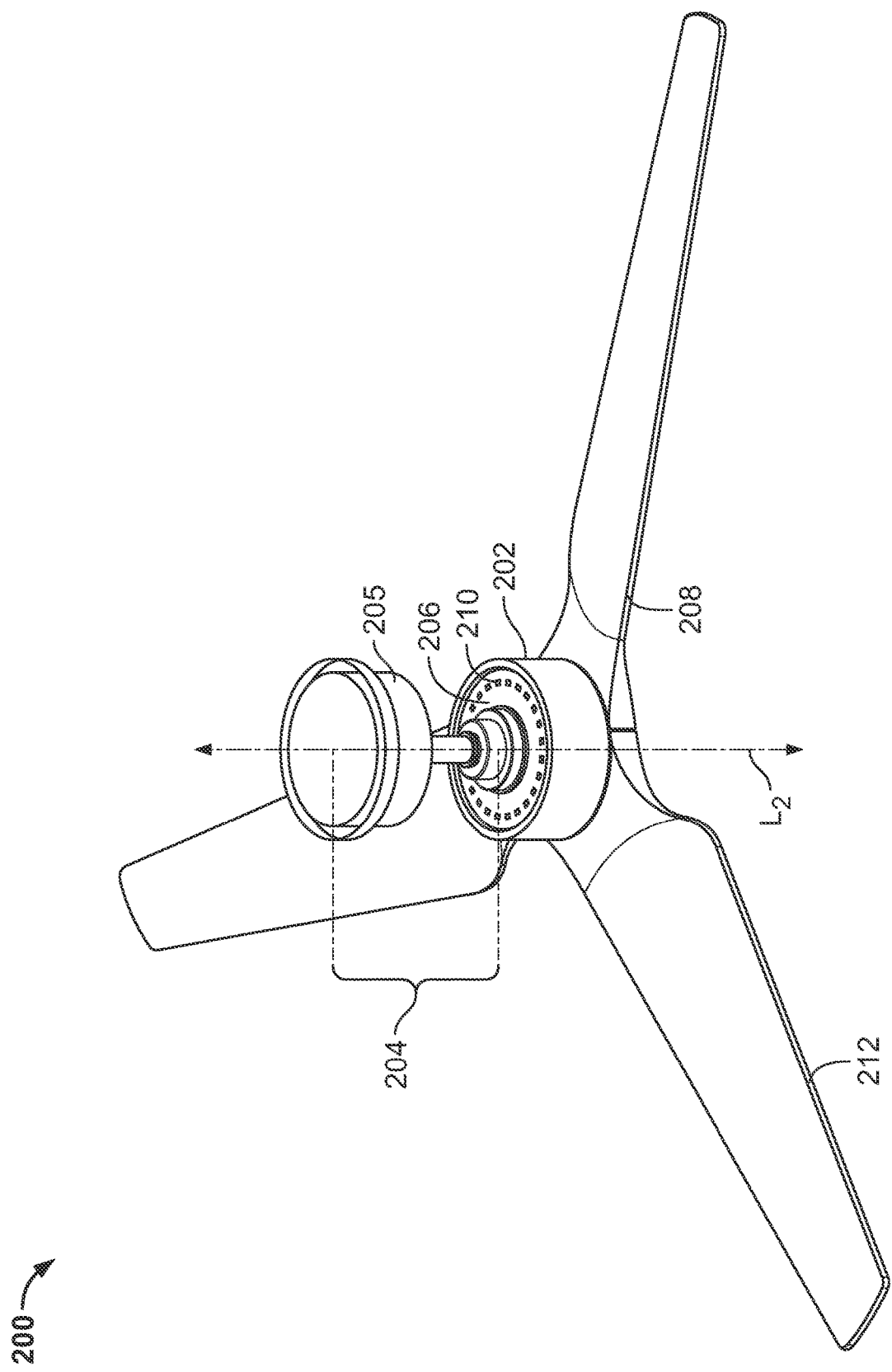
FIG. 2 shows an illustrative schema in accordance with principles of the invention.

FIG. 2 shows illustrative arrangement 200. Arrangement 200 may be included in fixture 112. Arrangement 200 may include housing 202. Housing 202 may have one or more features in common with fixture support 116. Arrangement 200 may include mount 204. Mount 204 may have one or more features in common with mount M. Mount 204 may include canopy 205. Arrangement 200 may include fixture 206. Fixture 206 may include a light. Arrangement 200 may include fixture 208. Fixture 208 may include a fan. Fixture 206 may include array 210. Array 210 may include germicidal emitters. Array 210 may include any suitable number of germicidal emitters. Table 12 lists illustrative ranges that may include a number of germicidal emitters in array 210.

TABLE 12

| Illustrative ranges that may include a number of germicidal emitters in array 210 | |
|---|---|
| Range | |
| Lower | Upper |
| 1 | 5 |
| 5 | 9 |
| 9 | 13 |
| 13 | 17 |
| 17 | 21 |
| 21 | 25 |
| 25 | 29 |
| 29 | 33 |
| 33 | 37 |
| 37 | 41 |
| 41 | 45 |
| 45 | 49 |
| 49 | 53 |
| 53 | 57 |
| 57 | 61 |

TABLE 12-continued

| Illustrative ranges that may include a number of germicidal emitters in array 210 | |
|---|---|
| Range | |
| Lower | Upper |
| 61 | 65 |
| 65 | 69 |
| 69 | 73 |
| 73 | 77 |
| 77 | 81 |
| 81 | 85 |
| 85 | 89 |
| 89 | 93 |
| 93 | 97 |
| 97 | 101 |
| 101 | >101 |
| Other suitable ranges that may include a number of emitters in array 210 | |

Array 210 may include one or more visible light emitters.

Fixture 208 may include blades 212. A motor inside housing 202 may cause blades 212 to rotate about axis L1. In motion, blades 212 may circulate air from environment E into captive volume $V_1$. Array 210 may treat the air when it moves through captive volume $V_1$.

Figure 3:
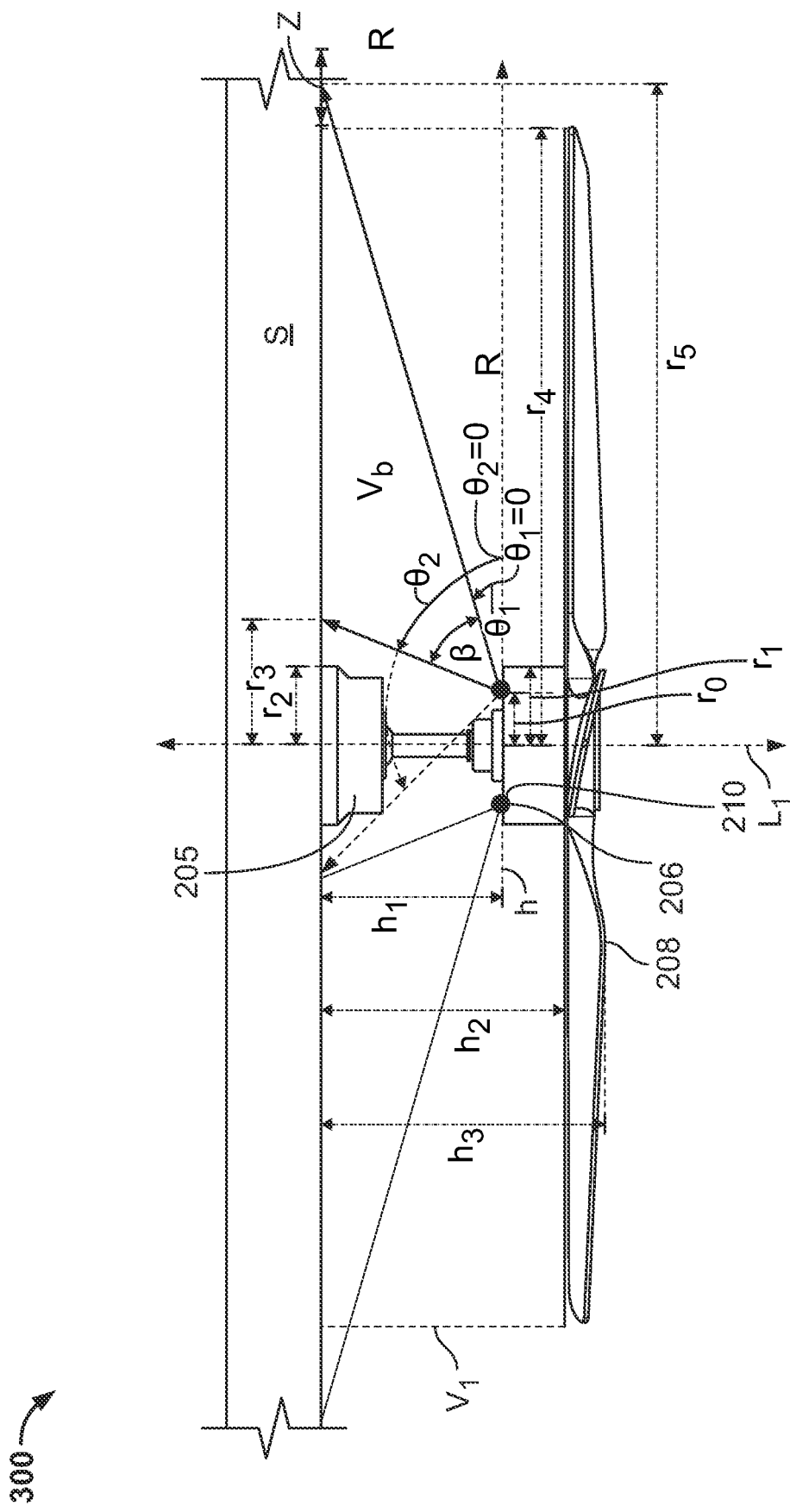
FIG. 3 shows illustrative information in accordance with principles of the invention.

FIG. 3 shows schema 300. Schema 300 defines treatment factors for arrangement 200. Table 13 lists illustrative factors and definitions.

TABLE 13

| Illustrative fixture factors | Illustrative definition |
|---|---|
| $V_{1,2}$ | Captive volumes |
| $h_1$ | Vertical height from lowest edge of blades 212 to structure S |
| $h_2$ | Vertical height from highest edge of blades 212 to structure S |
| $h_3$ | Vertical height from emitters in array 210 to structure S |
| $r_0$ | Radial (direction R) distance from $L_1$ to emitters in array 210 |
| $r_1$ | Radial distance from $L_1$ to outer edge of housing 202 |
| $r_2$ | Radial distance to outer extent of canopy 205 |
| $r_3$ | Radial distance to inner edge of beam incident on structure S |
| $r_4$ | Radial distance to tip of blades 212 |
| $r_5$ | Radial distance to outer edge of beam incident on structure S |
| β | Beam spread angle from array 210 |
| $θ_1$ | Angle (in direction θ) from horizontal plan h through emitters of array 210 to outer edge of beam |
| $θ_2$ | Angle (in direction θ) from horizontal plan h through emitters of array 210 to inner edge of beam |
| Dz | Height, above work stand, of bottom of fixture |
| α | Angle of beam edge relative to vertical, along d |
| c | Length of work stand |
| d | Depth of work stand |
| γ | Angle of beam edge relative to vertical, along c |
| Other suitable fixture factors | Other suitable definitions |

A beam edge may be defined by a decrease of 50% intensity relative to a maximum intensity of the beam. Beam edges may be identified by optical goniometry.

$θ_2$ may exceed 90°. $θ_1$ may be an angle that is not less than zero.

β may be adjusted by one or more LCD electric-field-focused lenses. $r_5$ may exceed $r_4$.

Table 14 lists illustrative ranges that may include light: blade ratio $r_5$:$r_4$.

TABLE 14

Illustrative ranges that may include light:blade ratio $r_5$:$r_4$

| Range | |
|---|---|
| Lower | Upper |
| 0.1 | 0.15 |
| 0.15 | 0.2 |
| 0.2 | 0.25 |
| 0.25 | 0.3 |
| 0.3 | 0.35 |
| 0.35 | 0.4 |
| 0.4 | 0.45 |
| 0.45 | 0.5 |
| 0.5 | 0.55 |
| 0.55 | 0.6 |
| 0.6 | 0.65 |
| 0.65 | 0.7 |
| 0.7 | 0.75 |
| 0.75 | 0.8 |
| 0.8 | 0.85 |
| 0.85 | 0.9 |
| 0.9 | 0.95 |
| 0.95 | 1 |
| 1 | 1.05 |
| 1.05 | 1.1 |
| 1.1 | 1.15 |
| 1.15 | 1.2 |
| 1.2 | 1.25 |
| 1.25 | 1.3 |
| 1.3 | 1.35 |
| 1.35 | 1.4 |
| 1.4 | 1.45 |
| 1.45 | 1.5 |
| 1.5 | 1.55 |
| 1.55 | 1.6 |
| 1.6 | 1.65 |
| 1.65 | 1.7 |
| 1.7 | 1.75 |
| 1.75 | 1.8 |
| 1.8 | 1.85 |
| 1.85 | 1.9 |
| 1.9 | 1.95 |
| 1.95 | 2 |
| 2 | 2.05 |
| 2.05 | 2.1 |
| 2.1 | 2.15 |
| 2.15 | 2.2 |
| 2.2 | 2.25 |
| 2.25 | 2.3 |
| 2.3 | 2.35 |
| 2.35 | 2.4 |
| 2.4 | 2.45 |
| 2.45 | 2.5 |
| 2.5 | >2.5 |

Other suitable ranges that may include light:blade ratio $r_5$:$r_4$

Table 15 lists illustrative ranges that may include an illumination intensity of each UV-C emitter in array 210.

TABLE 15

Illustrative ranges that may include an illumination intensity of each UV-C emitter in array 210 (radiant flux, mW)

| Range | |
|---|---|
| Lower | Upper |
| <3.5 | 3.50 |
| 3.50 | 3.55 |
| 3.55 | 3.60 |
| 3.60 | 3.65 |
| 3.65 | 3.70 |
| 3.70 | 3.75 |
| 3.75 | 3.80 |
| 3.80 | 3.85 |
| 3.85 | 3.90 |
| 3.90 | 3.95 |
| 3.95 | 4.00 |
| 4.00 | 4.05 |
| 4.05 | >4.05 |

Other suitable ranges that may include illumination intensity of array 210

Figure 4:
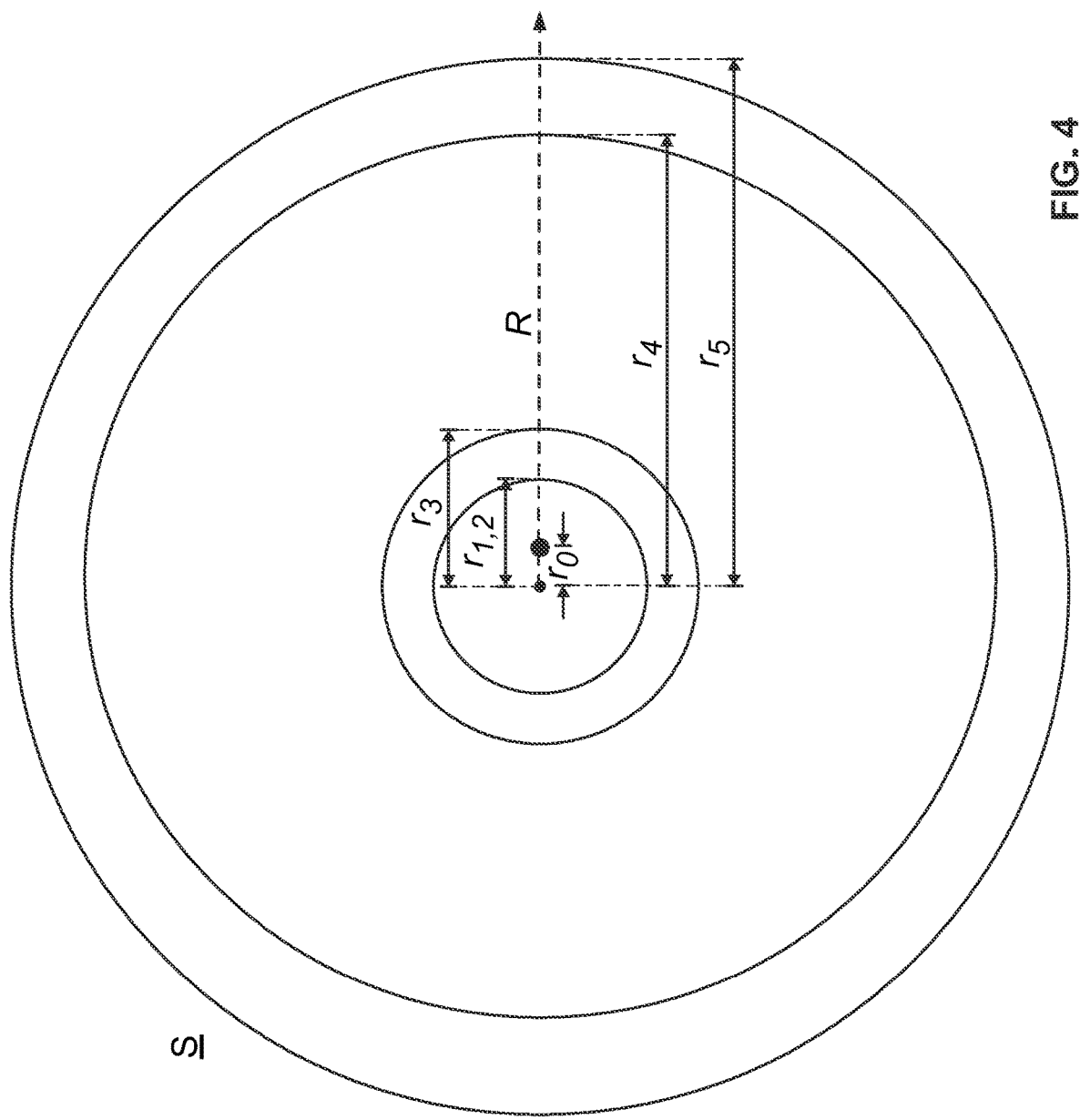
FIG. 4 shows illustrative information in accordance with principles of the invention.

FIG. 4 shows fixture factors projected along $L_1$ onto structure S, when structure S is a flat horizontal surface.

Figure 5:
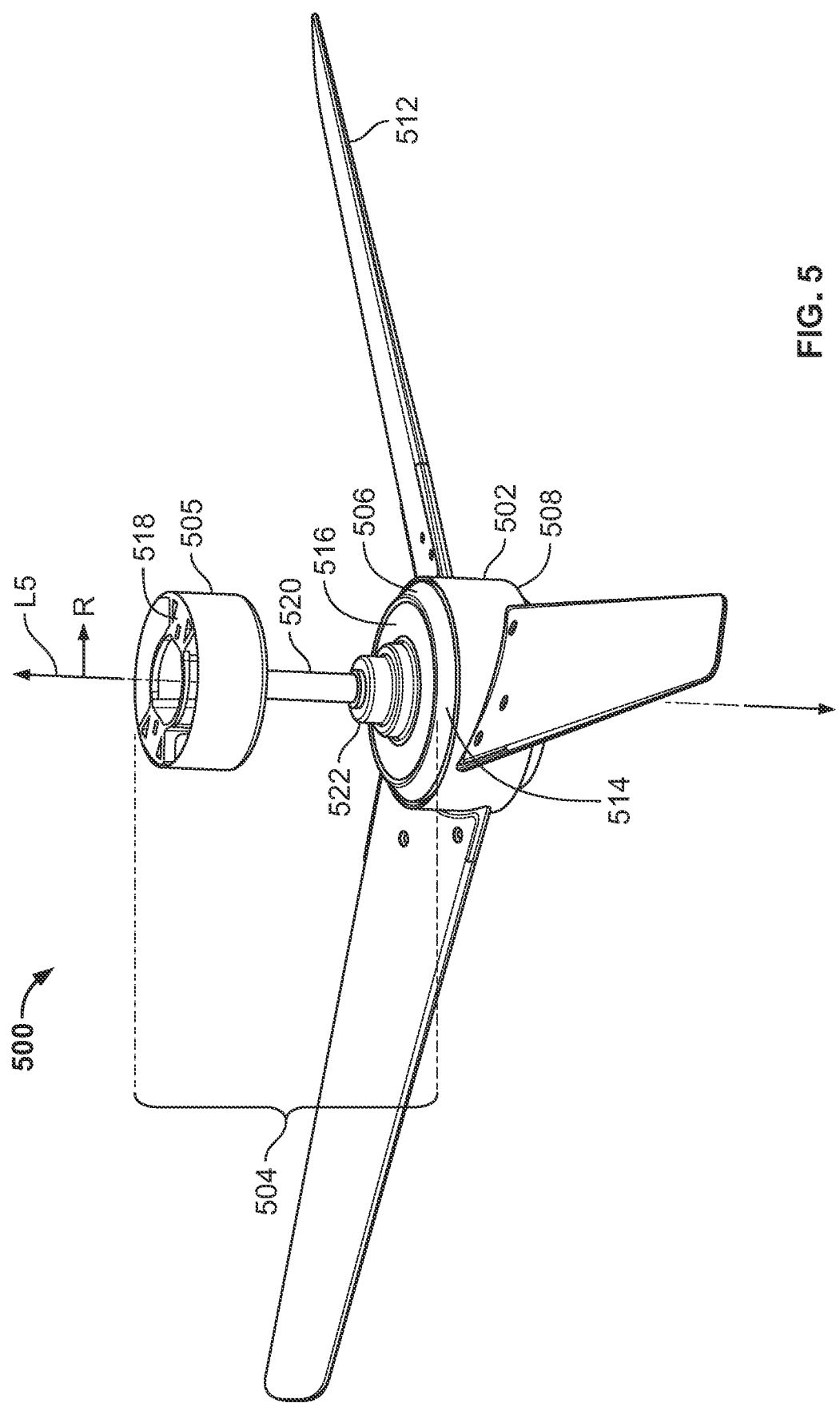
FIG. 5 shows illustrative apparatus in accordance with principles of the invention.

FIG. 5 shows illustrative arrangement 500. Arrangement 500 may have one or more features in common with arrangement 200. Arrangement 500 may be included in fixture 112. Arrangement 500 may include housing 502. Housing 502 may have one or more features in common with fixture support 116. Arrangement 500 may include mount 504. Mount 504 may have one or more features in common with mount M. Mount 504 may include canopy 505. Arrangement 500 may include fixture 506. Fixture 506 may include a light. Arrangement 500 may include fixture 508. Fixture 508 may include a fan. Fixture 506 may include an array (not shown) of germicidal emitters. Fixture 508 may include blades 512. A motor inside housing 502 may cause blades 512 to rotate about axis $L_5$. In motion, blades 512 may circulate air from environment E into captive volume $V_1$. The array may treat the air when it moves through captive volume $V_1$ Fixture 506 may include platform 514. Platform 514 may support the array. Fixture 506 may include shield 516. Platform 514 may support shield 516. Shield 516 may include quartz glass. The quartz glass may have a transmissivity of UVC light. Shield 516 may prevent dust from environment E from settling on the array. Shield 516 may be displaceable from platform 514. This may provide access by a user to the array. Shield 516 may be removable from fixture 506.

Mount 504 may include bracket 518. Bracket 518 may include holes for fasteners (not shown). The fasteners may attach fixture 506 to structure S. Mount 504 may include hanger 520. Hanger 520 may engage bracket 518 at an upper joint (not shown). Hanger 520 may engage fixtures 506 at a lower joint (not shown). Hanger 520 may engage fixture 508 at the lower joint or another lower joint (not shown). Mount 504 may include cover 522. Cover 522 may cover the lower joint or the other lower joint.

Figure 6:
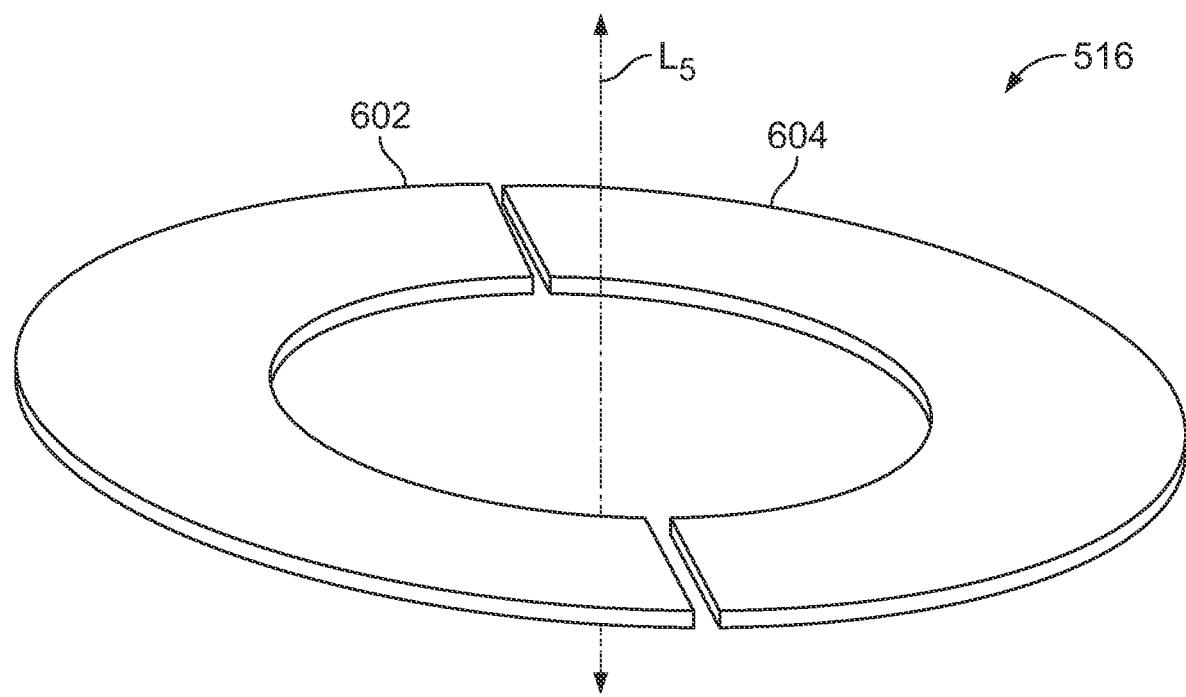
FIG. 6 shows illustrative apparatus in accordance with principles of the invention.

FIG. 6 shows shield 516. Shield 516 may include panel 602. Shield 516 may include panel 604. Panels 602 and 604 are shown offset from each other for the sake of illustration. One or both of panels 602 and 604 may span an arc of less than 360°. The difference between 360° and the arc may define a gap. The gap may provide clearance relative to mount 504 for the panel to be removed from the fixture. This may provide access to array 210, which may be removable for service or repair.

Figure 7:
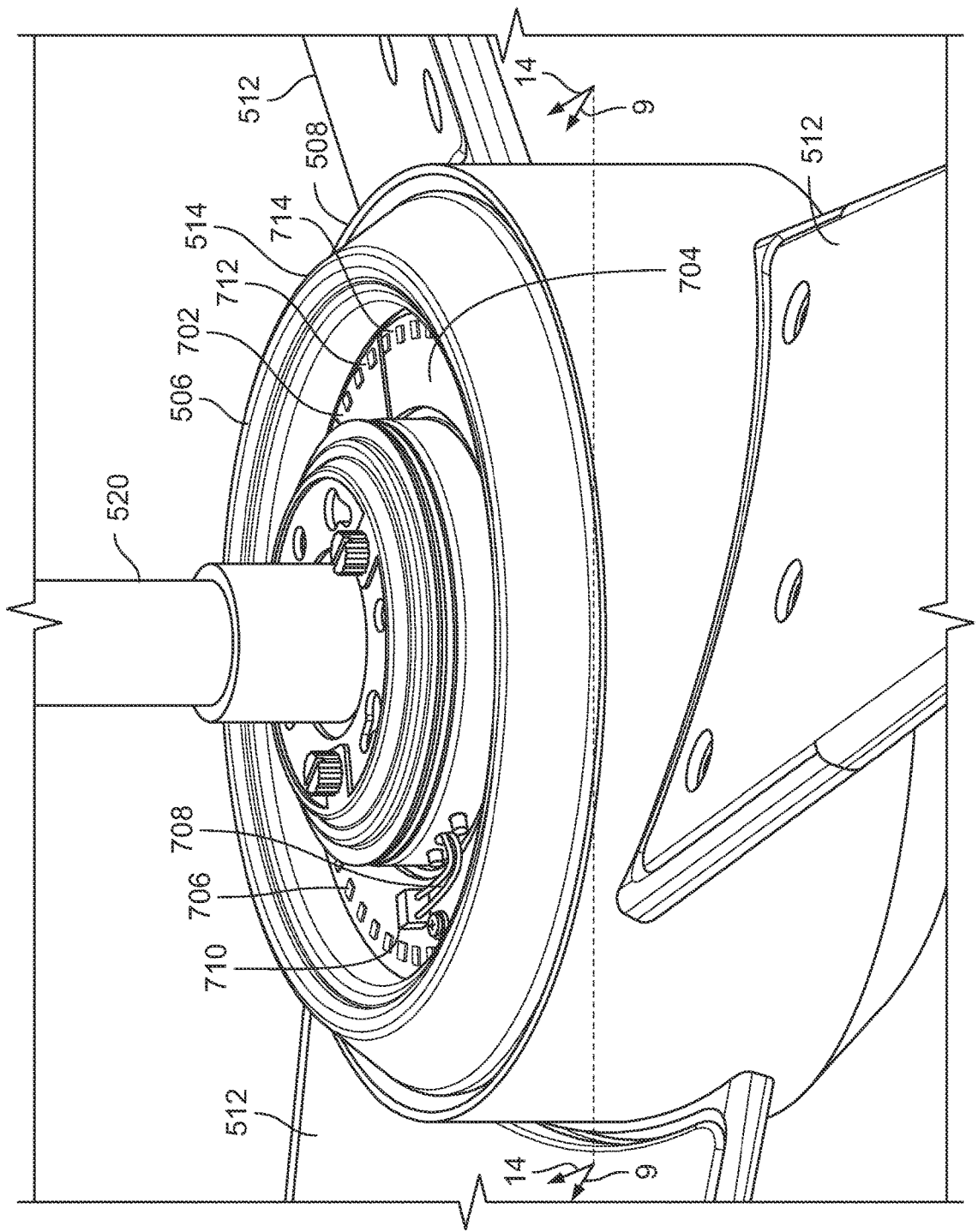
FIG. 7 shows illustrative apparatus in accordance with principles of the invention.

FIG. 7 shows in part arrangement 500 with shield 516 removed. Array 702 is disposed on platform 514. Array 702 may include substrate 704. Array 702 may include emitters 706. Wires 708 may deliver power to an LED driver circuit (not shown) via connector 710. Wires 708 may be led through hanger 520 to line power in structure S. Array 702 may include segment 712. Array 702 may include segment 714. All or some of emitters 706 and all or some components of the driver circuit may be disposed on segment 712. All or some of emitters 706 and all or some components of the driver circuit may be disposed on segment 714.

Figure 8:
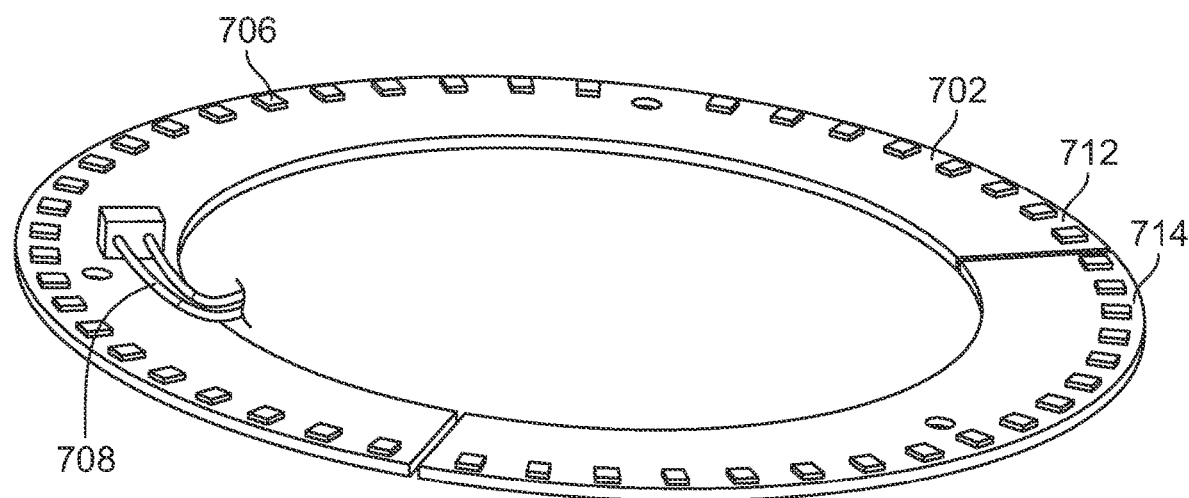
FIG. 8 shows illustrative apparatus in accordance with principles of the invention.

FIG. 8 shows array 702. One or both of segments 712 and 714 may span an arc of less than 360°. Segments 712 and 714 are shown offset from each other for the sake of illustration. The difference between 360° and the arc may define a gap. The gap may provide clearance relative to mount 504 for the array to be removed from the fixture.

Figure 9:
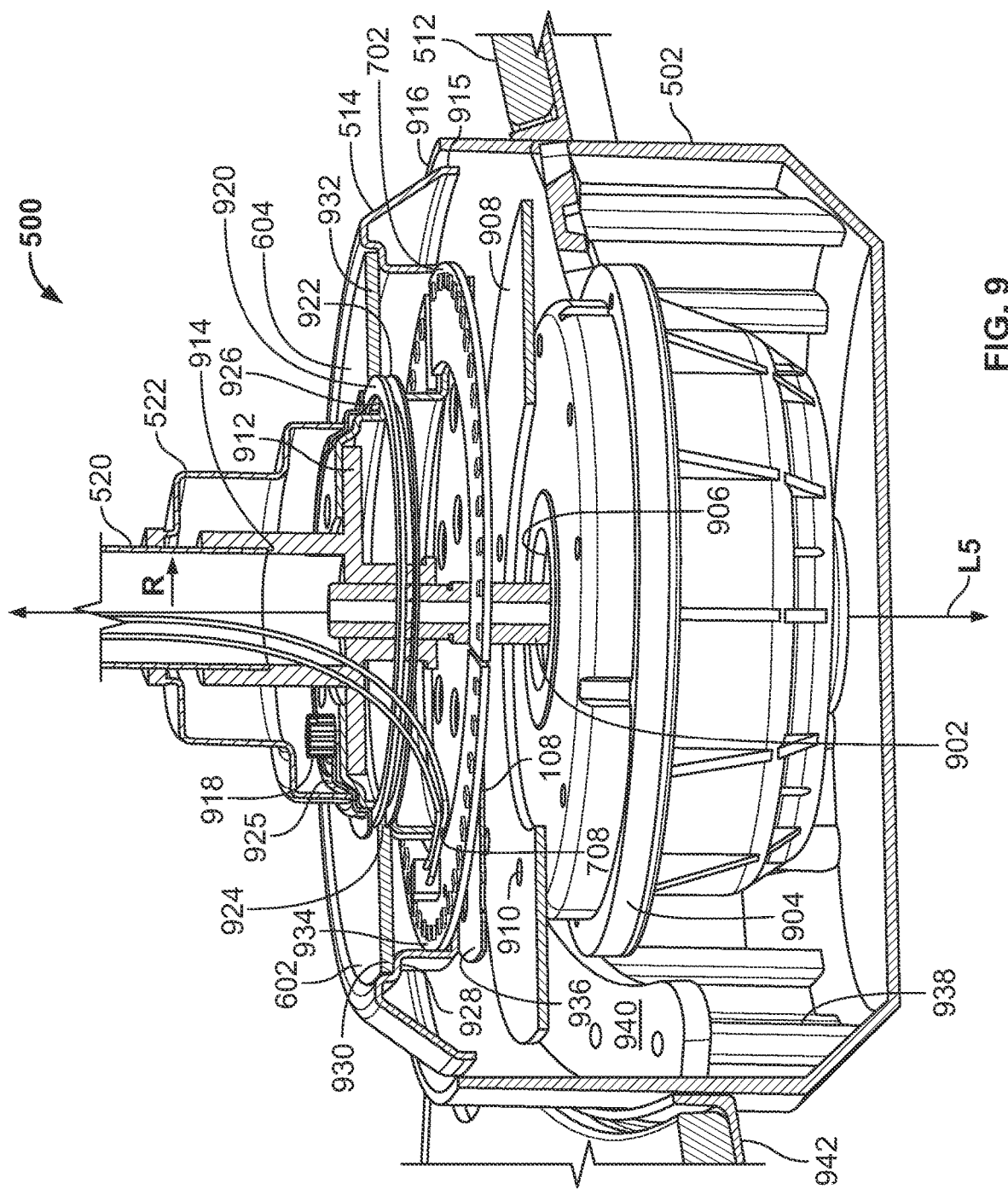
FIG. 9 is a partial cross-section of part of a view taken along view lines 9-9 of FIG. 7.

FIG. 9 is a partial cross-section of arrangement 500, along the view lines shown in FIG. 9. Drive shaft 902 may be bracketed to hanger 520. Drive shaft 902 may be rotationally (about axis $L_5$) fixed with respect to hanger 520. Drive shaft 902 may be longitudinally (along axis $L_5$) fixed with respect to hanger 520. Electric motor 904 may include windings (not shown) and magnets (not shown) that cause motor 904 to rotate about axis $L_5$ relative to drive shaft 902. Motor 904 may apply torque to drive shaft 902 via one or more collars such as collar 906.

Arrangement 500 may include disc 908. Disc 908 may be attached to motor 904. Disc 908 may rotationally (about axis $L_5$) fixed relative to motor 904. Disc 908 may include mounting holes such as 910 for attaching disc 908 to motor 904 via fasteners.

Housing 502 may be rotationally (about axis $L_5$) fixed relative to motor 904. disc 908 may fix housing 502 to motor 904.

Arrangement 500 may include flange 912. Flange 912 may be rotationally (about axis $L_5$) fixed relative to hanger 520. Flange 912 may be longitudinally (along axis $L_5$) fixed relative to hanger 520. Flange 912 may be rotationally (about axis $L_5$) fixed relative to drive shaft 902. Flange 912 may be longitudinally (along axis $L_5$) fixed relative to drive shaft 902.

Flange 912 may include ledge 914. Ledge 914 may limit the insertion of hanger 520 into flange 912.

Flange 912 may support platform 514. Platform 514 may include outer edge 915. Outer edge 915 may be inside rim 916 of housing 502. Outer edge 915 may be (although not shown) outside rim 916 of housing 502. Outer edge 915 may be below rim 916 of housing 502. Outer edge 915 may be (although not shown) above rim 916 of housing 502.

A fastener such as knurled bolt 918 may fasten platform 514 to flange 912.

Arrangement 500 may include ring 920. Arrangement 500 may include ring 922. Rings 920 and 922 may secure inner radial edges 924 and 926, of panels 602 and 604, respectively. Ring 920 may be disposed above edges 924 and 926. Ring 922 may be disposed below edges 924 and 926. Bolt 918 may apply compression to skirt 925 and platform 514. The compression may compress rings 920 and 922 against edges 924 and 926. This may secure panels 602 and 604 against displacement. Such displacement may be a consequence of vibrations or rocking from motor 904. Shelf 928 of platform 514 may support outer radial edges 930 and 932 of panels 602 and 604, respectively. Shelf 934 may support array 702.

Arrangement 500 may include guard plate 936. Guard plate 936 may prevent wires 708 from contacting motor 094.

Guard plate 936 may be longitudinally fixed relative to drive shaft 902.

To replace a segment of array 702, a user may slide cover 522 upward, release panels 602 and 604 by backing of bolts such as 918, disconnect connector 710 from array 702, and remove one or both of segments 712 and 714 from platform 514. New segments may be placed in platform 514 and connected to connector 710. Panels 602 and 604 may be re-installed and re-secured. Cover 522 may be restored to its operational position.

Housing 502 may include buttresses such 938. Tabs such as 940 of blade supports 942 may be secured inside housing 502. Tab 940 may be secured to buttress 938 by a fastener (not shown).

Figure 10:
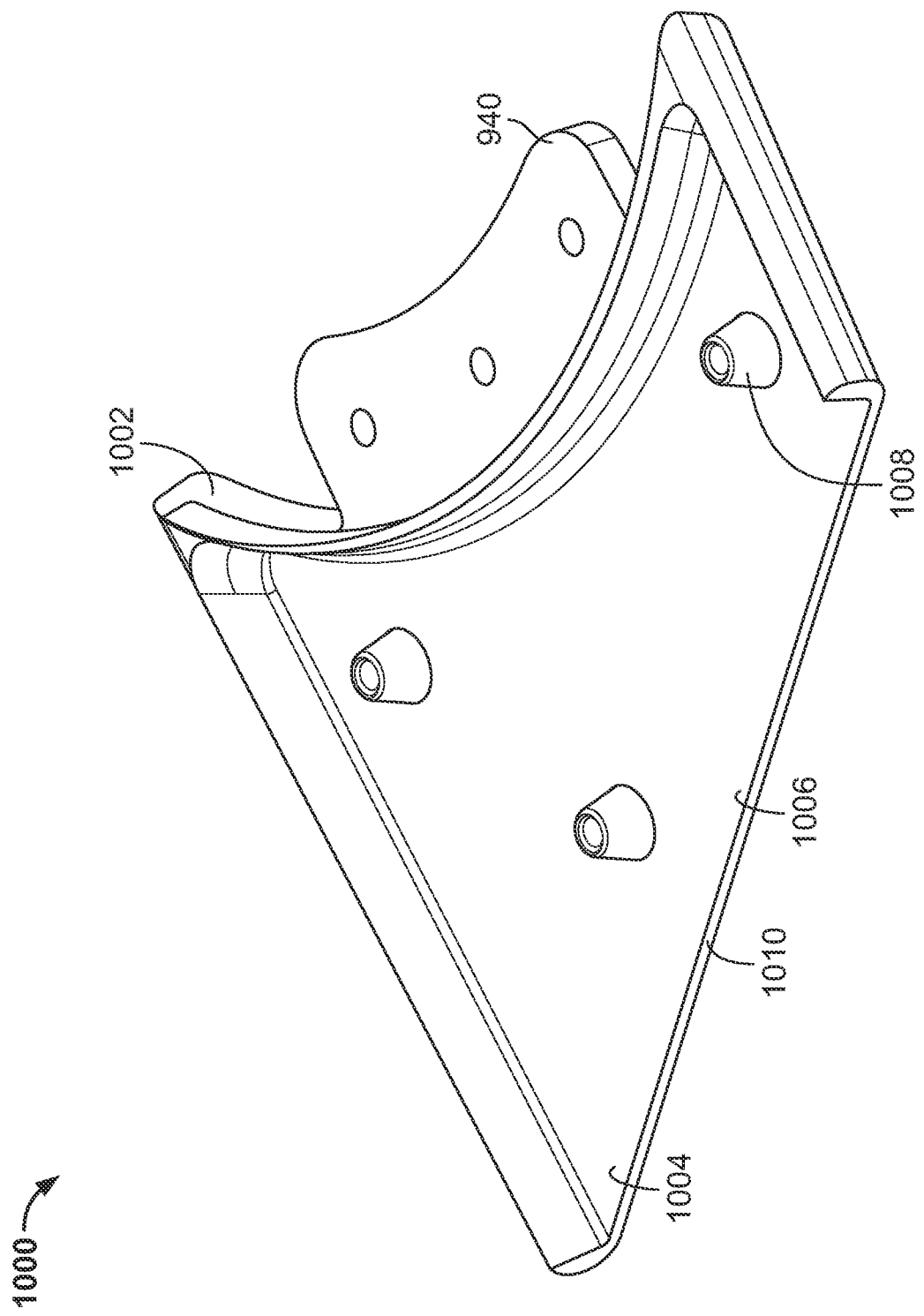
FIG. 10 shows illustrative apparatus in accordance with principles of the invention.

FIG. 10 shows illustrative blade bracket 1000. Bracket 1000 may include tab 940. Bracket 1000 may include surface 1002. Surface 1002 may be disposed flush against housing 502 when tab 940 is attached to buttresses such as 938. Bracket 1000 may include recess 1006. Bracket 1000 may include top side 1004. Top side 1004 may include recess 1006. Recess 1006 may receive a blade such as 512. Bracket 1000 may include bosses such as 1008. Boss 1008 may fix positions corresponding holes in the blades. Boss 1008 may receive a fastener (not shown) that fastens the blade to bracket 1000. Edge 1010 may abut a corresponding surface on blade 512.

Figure 11:
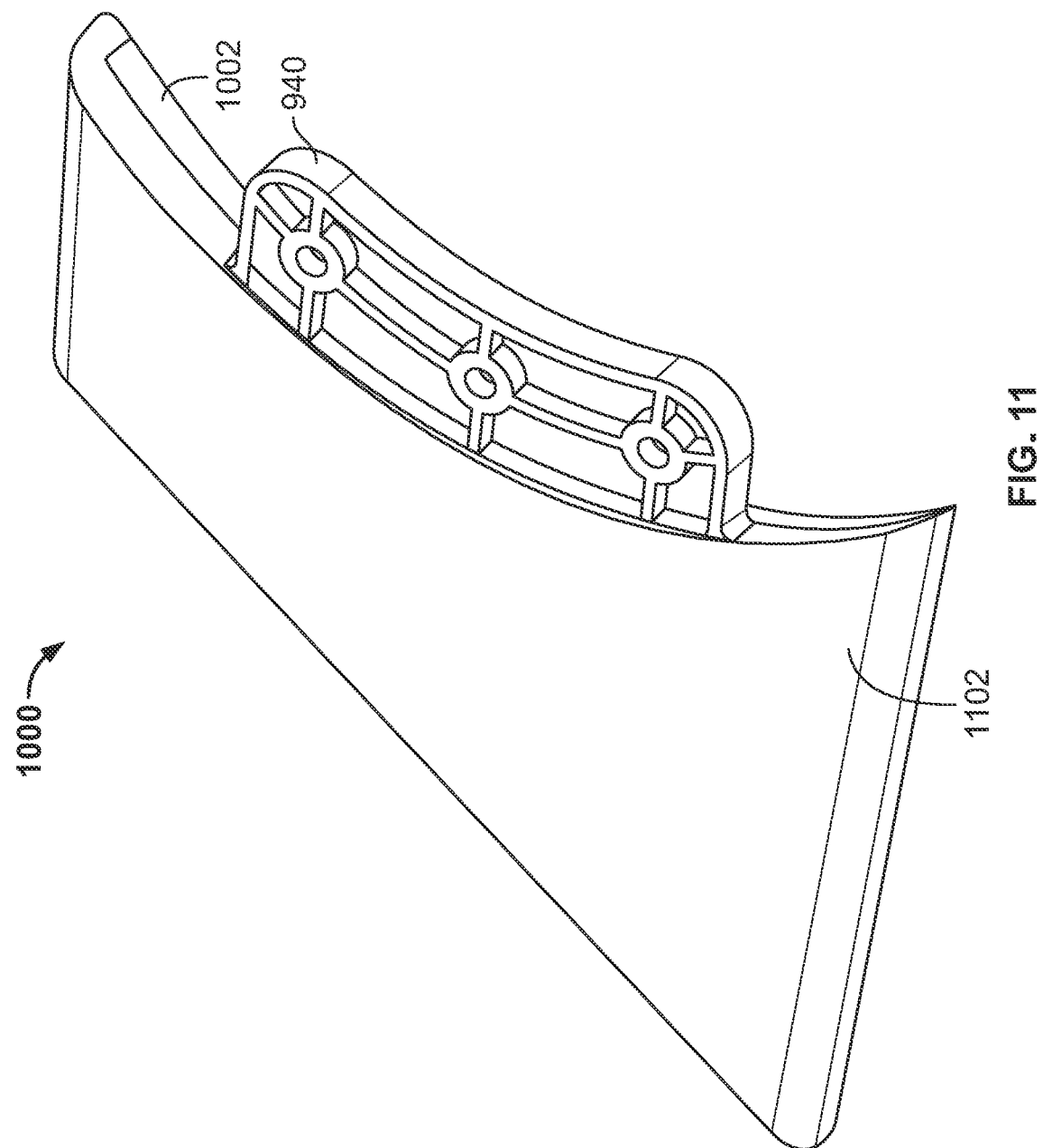
FIG. 11 shows illustrative apparatus in accordance with principles of the invention.

FIG. 11 shows that bracket 1000 may include bottom side 1102.

Figure 12:
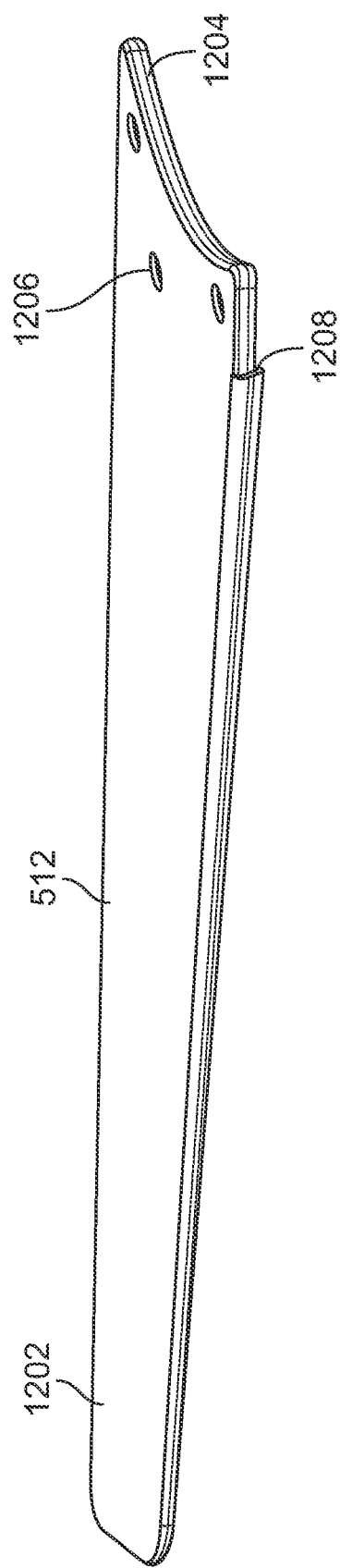
FIG. 12 shows illustrative apparatus in accordance with principles of the invention.

FIG. 12 shows blade 512. Blade 512 may include top side 1202. Blade 512 may include mounting end 1204. Mounting end 1204 may conform to recess 1006. Mounting end 1204 may include mounting holes such as 1206. Mounting holes 1206 may align with bosses such as 1008. Edge 1208 may abut edge 1010 of bracket 1000.

Figure 13:
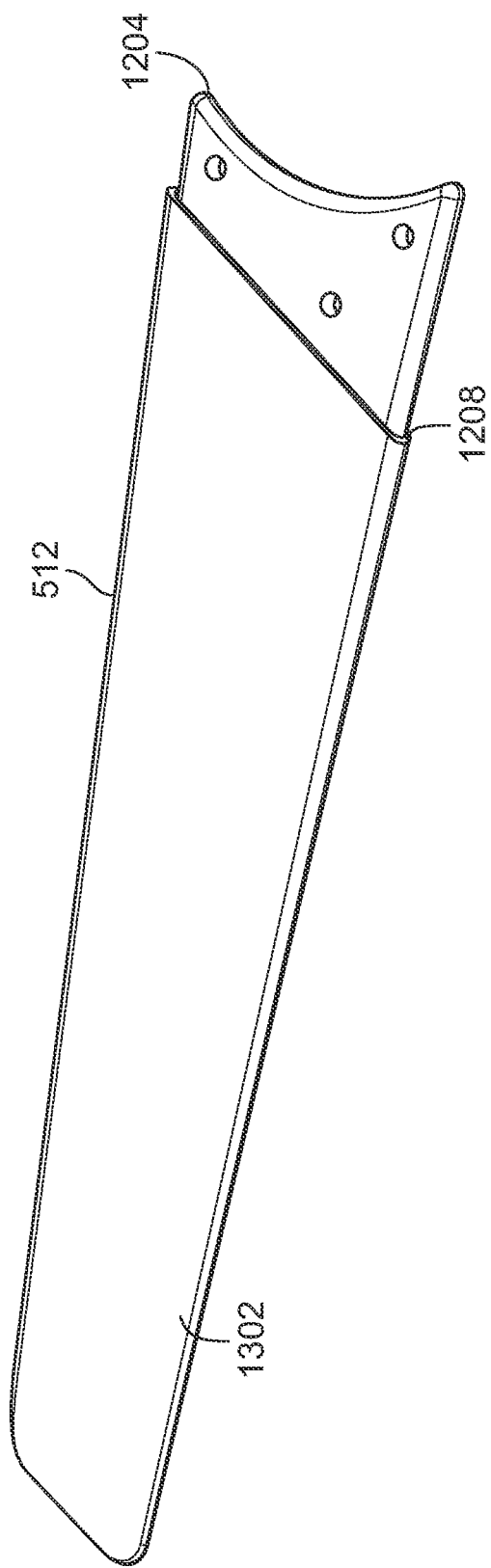
FIG. 13 shows illustrative apparatus in accordance with principles of the invention.

FIG. 13 shows blade 512 from a perspective that is different from that shown in FIG. 12. Blade 512 may include bottom side 1302.

Figure 14:
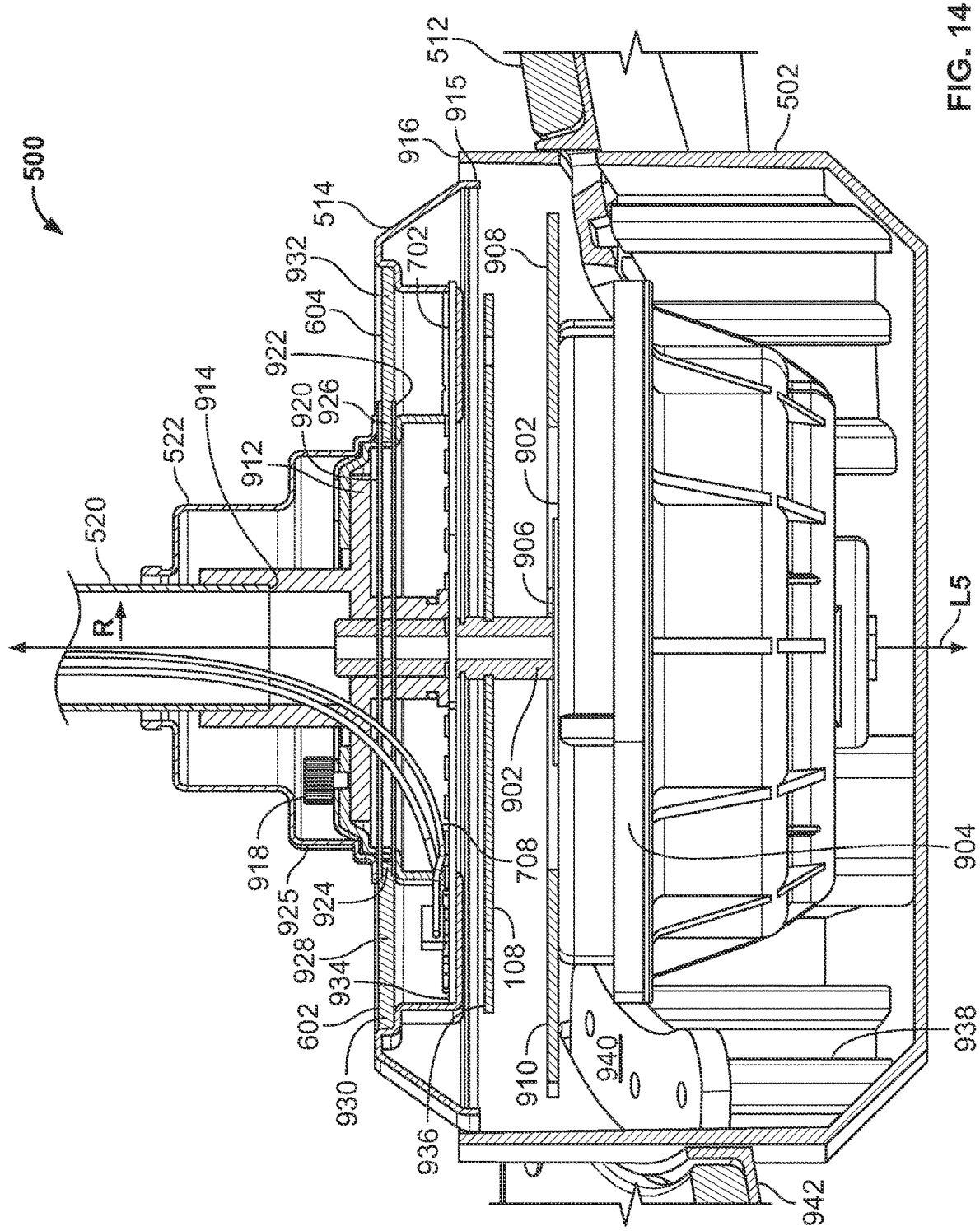
FIG. 14 is a partial cross-section of part of a view taken along view lines 14-14 of FIG. 7.

FIG. 14 shows arrangement 500 from a perspective that is different from that shown in FIG. 9.

Figure 15:
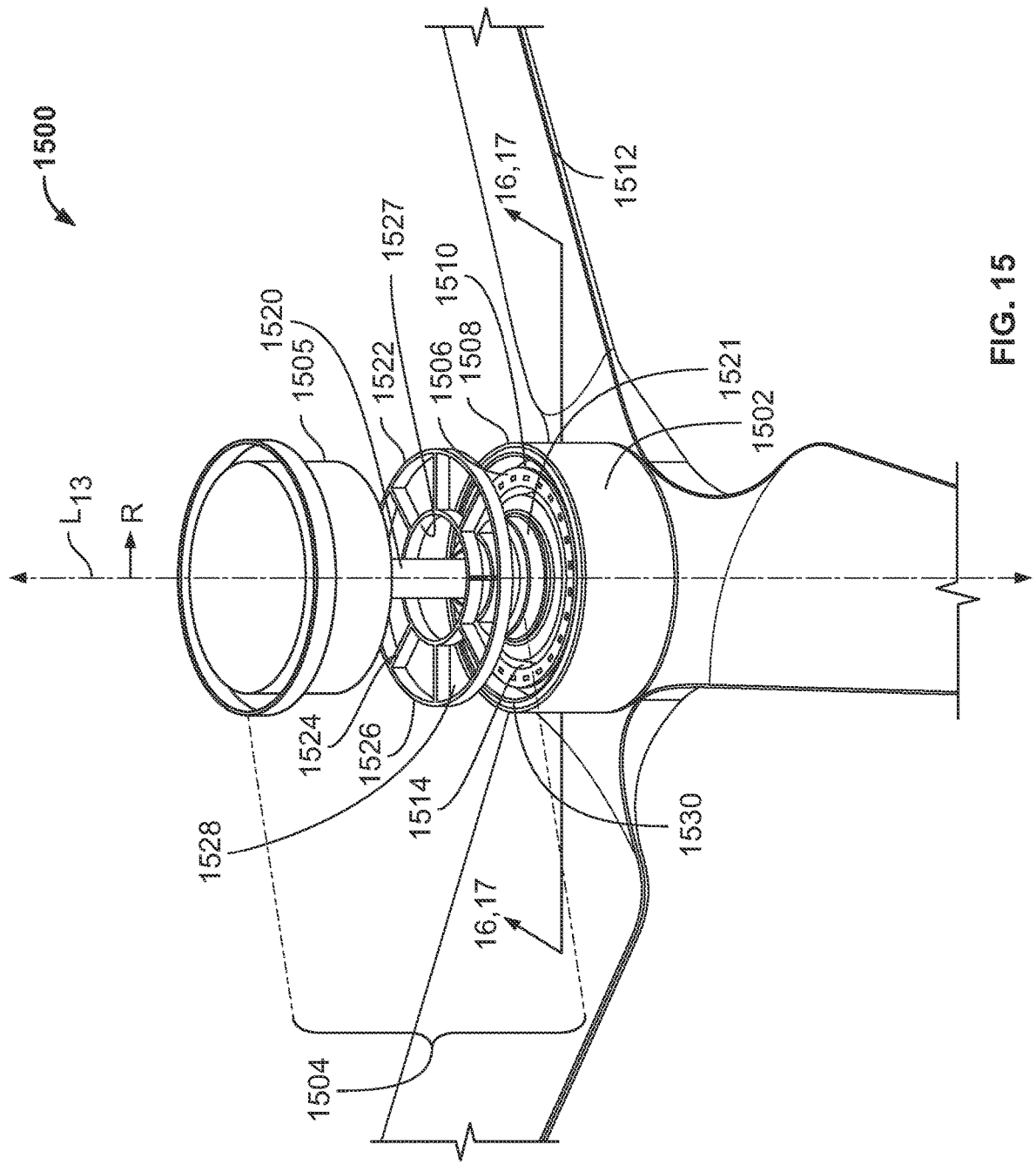
FIG. 15 shows illustrative apparatus in accordance with principles of the invention.

FIG. 15 shows illustrative arrangement 1500. Arrangement 1500 may have one or more features in common with arrangement 200. Arrangement 1500 may be included in fixture 112. Arrangement 1500 may include housing 1502. Housing 1502 may have one or more features in common with fixture support 116. Arrangement 1500 may include mount 1504. Mount 1504 may have one or more features in common with mount M. Mount 1504 may include canopy 1505. Arrangement 1500 may include fixture 1506. Fixture 1506 may include a light. Arrangement 1500 may include fixture 1508. Fixture 1508 may include a fan. Fixture 1506 may include array 1510 of germicidal emitters. Fixture 1508 may include blades 1512. A motor (not shown) inside housing 1502 may cause blades 1512 to rotate about axis $L_{13}$. In motion, blades 1512 may circulate air from environment E into captive volume $V_1$. The array may treat the air when it moves through captive volume $V_1$.

Fixture 1506 may include platform 1514. Platform 1514 may support the array. Fixture 1506 may include a shield (not shown) for array 1510. Platform 1514 may support shield the shield. The shield may include quartz glass. The quartz glass may have a transmissivity of UVC light. The shield may prevent dust from environment E from settling on the array. The shield may be displaceable from platform 1514. This may provide access by a user to the array. The shield may be removable from fixture 1506.

Mount 1504 may include hanger 1520. Hanger 1520 may engage a bracket (not shown) at an upper joint (not shown). Hanger 1520 may engage fixture 1506 at a lower joint (not shown). Hanger 1520 may engage fixture 1508 at the lower joint or another lower joint (not shown). Cover 1521 may cover the lower joint the other lower joint.

Arrangement 1500 may include louver 1522. Louver 1522 may include vertical blinds such as radial blinds 1524. Louver 1522 may include vertical blind such as circumferential blind 1526. Louver 1522 may include vertical blind such as circumferential blind 1527. The blinds may define open windows such as 1528. Louver 1522 may be deployed on housing 1502. Louver 1522 may reduce radiation from array 1510 that propagates in a non-vertical direction. This may reduce the propagation of light to areas in environment E that are desired to be protected from the light. Housing 1502 may include groove 1530. Louver 1522 may be placed such that circumferential blind 1526 extends into groove 1530. Louver 1522 may be placed such that circumferential blind 1527 circumscribes cover 1521. An outer surface of cover 1521 may center louver 1522 relative to axis $L_{13}$ as louver is lowered toward groove 1530.

Louver 1522 may be deployed manually. Louver 1522 may be deployed by releasing louver 1522 from canopy 1505. Guides (not shown) may guide louver 1522 from canopy 1505 to the deployed state. Arrangement 1500 may include a sensor (not shown) that detects the presence of an object or person in environment E. The sensor may trigger the release of louver 1522. Louver 1522 may provide glare control].

Figure 16:
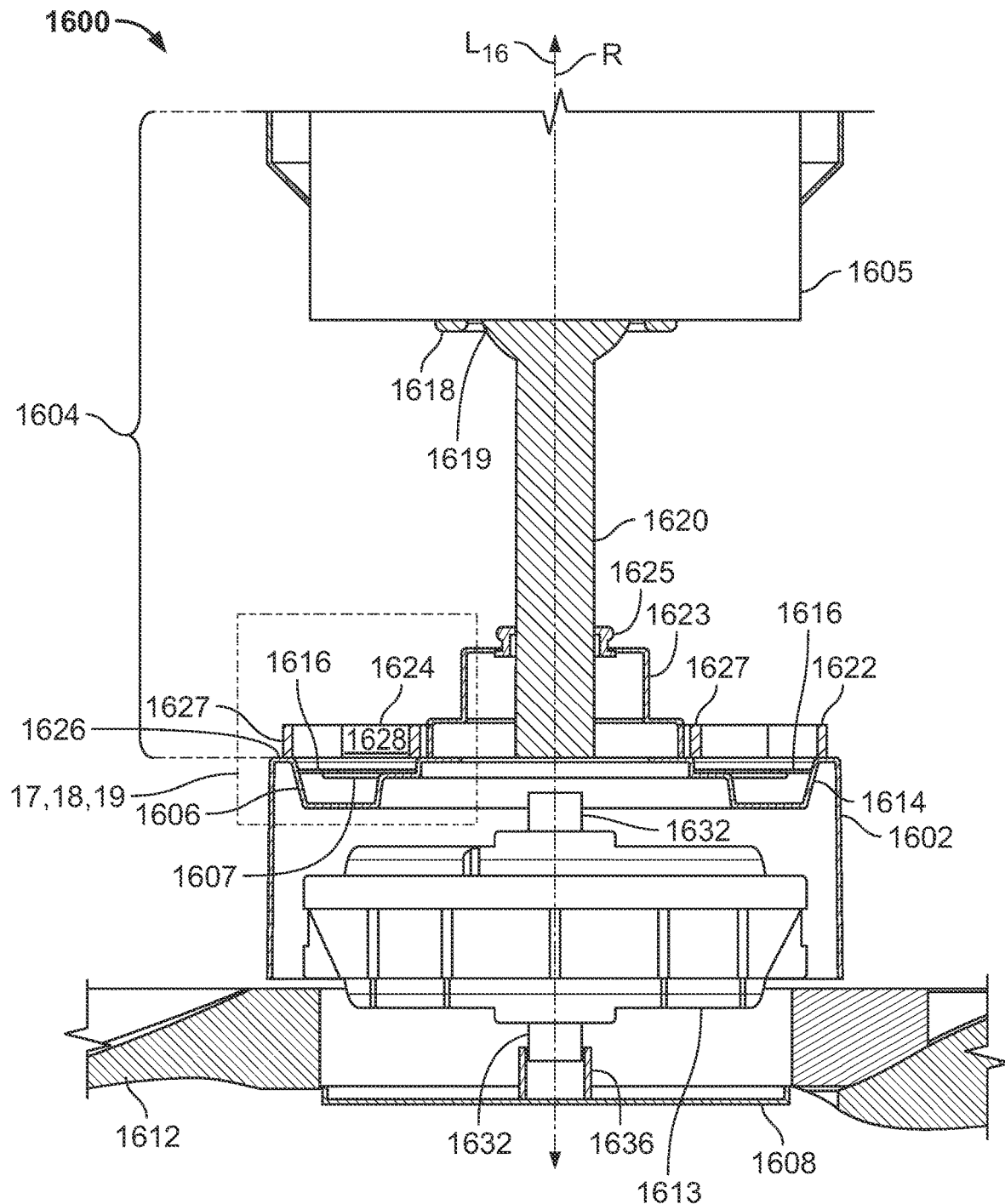
FIG. 16 is a partial cross-section of part of a view taken along view lines 16-16 of FIG. 7.

FIG. 16 shows illustrative arrangement 1600. Arrangement 1600 may have one or more features in common with arrangement 200. Arrangement 1600 is shown from a perspective defined by view lines 16-16 in FIG. 15. Arrangement 1600 may be included in fixture 112. Arrangement 1600 may include housing 1602. Housing 1602 may have one or more features in common with fixture support 116. Arrangement 1600 may include mount 1604. Mount 1604 may have one or more features in common with mount M. Mount 1604 may include canopy 1605. Arrangement 1600 may include fixture 1606. Fixture 1606 may include a light. Arrangement 1600 may include fixture 1608. Fixture 1608 may include a fan. Fixture 1606 may include an array 1607 of germicidal emitters. Fixture 1608 may include blades 1612. Motor 1613 inside housing 1602 may cause blades 1612 to rotate about axis $L_{16}$. In motion, blades 1612 may circulate air from environment E into captive volume $V_1$. The array may treat the air when it moves through captive volume $V_1$.

Fixture 1606 may include platform 1614. Platform 1614 may support the array. Fixture 1606 may include shield 1616. Platform 1614 may support shield 1616. Shield 1616 may include quartz glass. The quartz glass may have a transmissivity of UV-C light. Shield 1616 may prevent dust from environment E from settling on the array. Shield 1616 may be displaceable from platform 1614. This may provide access by a user to the array. Shield 1616 may be removable from fixture 1606.

Mount 1604 may include bracket 1618. Bracket 1618 may include holes for fasteners (not shown). The fasteners may attach fixture 1606 to structure S. Mount 1604 may include hanger 1620. Hanger 1620 may engage bracket 1618 at upper joint 1619. Hanger 1620 may engage fixtures 1606 at a lower joint (not shown). Hanger 1620 may engage fixture 1608 at the lower joint or another lower joint (not shown). Mount 1604 may include cover 1623. Mount 1604 may include collar 1625. Cover 1623 may cover the lower joint or the other lower joint.

Arrangement 1600 may include louver 1622. Louver 1622 may include vertical blinds such as radial blinds 1624. Louver 1622 may include vertical blind such as circumferential blind 1627. Louver 1622 may include vertical blind such as circumferential blind 1627. The blinds may define open windows such as 1628. Louver 1622 may be deployed on housing 1602. Louver 1622 may be deployed on platform 1614. Louver 1622 may be deployed on flat shoulder 1626 of platform 1614. Louver 1622 may reduce illumination from array 1607 that propagates in a non-vertical direction. This may reduce the propagation of light to areas in environment E that are desired to be protected from the light. Louver 1622 may be placed such that circumferential blind 1627 circumscribes cover 1623. An outer surface of cover 1623 may center louver 1622 relative to axis $L_{13}$ as louver is lowered toward flat shoulder 1626.

Louver 1622 may be deployed manually. Louver 1622 may be deployed by releasing louver 1622 from canopy 1605. Guides (not shown) may guide louver 1622 from canopy 1605 to the deployed state. Arrangement 1600 may include a sensor (not shown) that detects the presence of an object or person in environment E. The sensor may trigger the release of louver 1622.

Shaft 1632 may be fixed to hanger 1620. Shaft 1632 may be rotationally (about axis $L_{17}$) fixed with respect to hanger 1620. Shaft 1632 may be longitudinally (along axis $L_5$) fixed with respect to hanger 1620. Electric motor 1613 may include windings (not shown) and magnets (not shown) that drive shaft 1632 to rotate about axis $L_{17}$ relative to shaft 1632. Drive shaft 1632 may be rotationally (about axis $L_{17}$) fixed with respect to flange 1636. Drive shaft 1632 may rotate flange 1636. Flange 1636 may be fixed to and rotate blades such as 1612.

Housing 1602 may be rotationally (about axis $L_{17}$) fixed with respect to hanger 1620.

Figure 17:
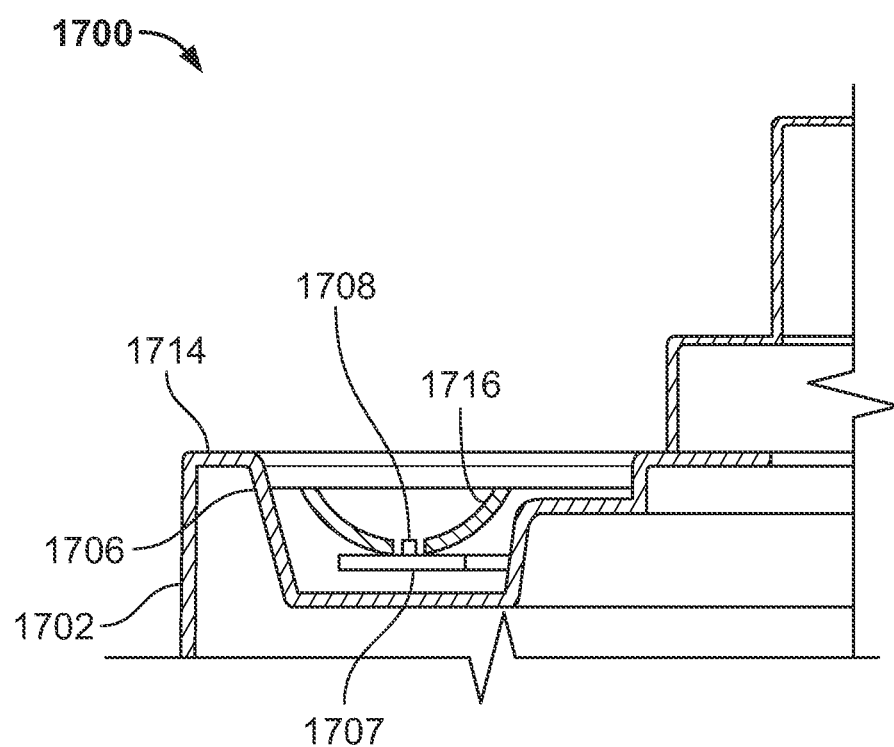
FIG. 17 shows illustrative apparatus in accordance with the principles of the invention, in a view analogous to that shown in box 17 of FIG. 16.

FIG. 17 shows in part illustrative arrangement 1700. Arrangement 1700 may have one or more features in common with arrangement 200. Arrangement 1700 is shown from a perspective defined by view lines 17-17 in FIG. 15. The view of FIG. 17 corresponds to view box 17 of FIG. 16. Arrangement 1700 may be included in fixture 112. Arrangement 1700 may include housing 1702. Housing 1702 may have one or more features in common with fixture support 116. Arrangement 1700 may include fixture 1706. Fixture 1706 may include array 1707. Array 1707 may include light-emitting diodes such as 1708.

Fixture 1706 may include platform 1714. Platform 1714 may support array 1707. Fixture 1706 may include reflector 1716. Platform 1714 may support reflector 1716. Reflector 1716 may have a parabolic cross-section. Reflector 1716 may focus light from emitter 1708 toward the upward direction.

Figure 18:
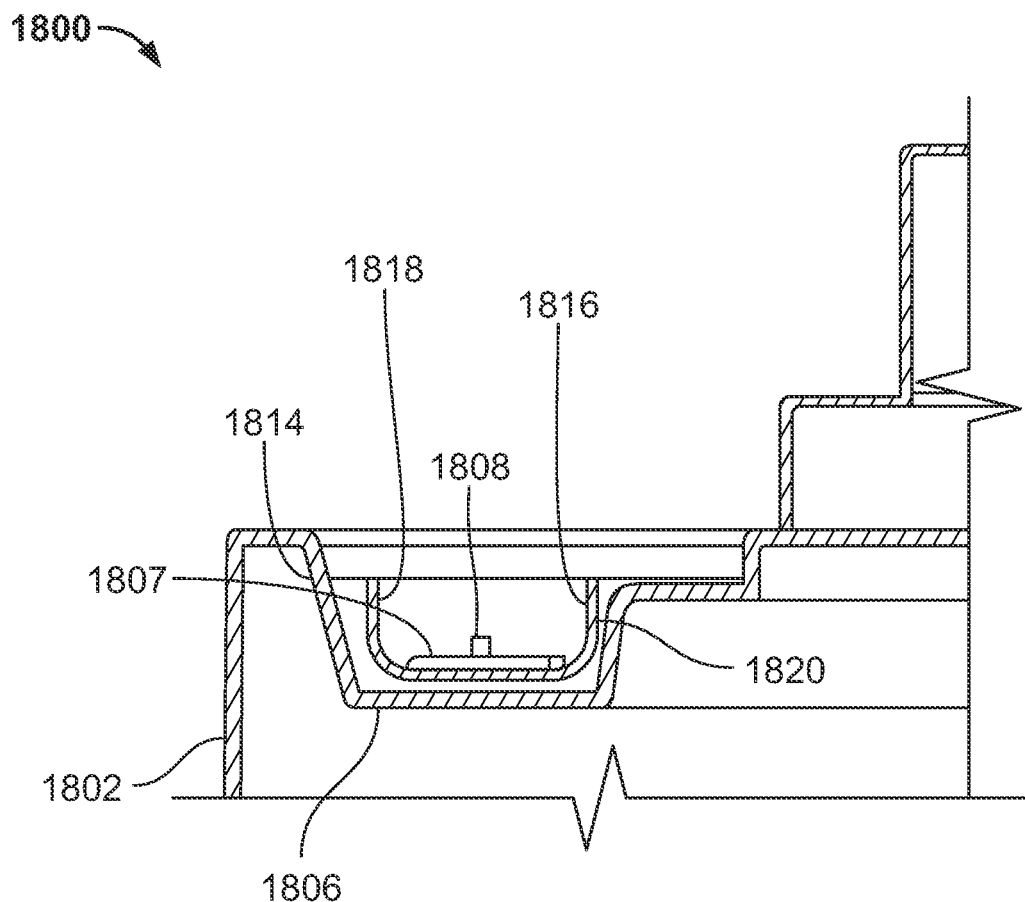
FIG. 18 shows illustrative apparatus in accordance with the principles of the invention, in a view analogous to that shown in box 18 of FIG. 16.

FIG. 18 shows in part illustrative arrangement 1800. Arrangement 1800 may have one or more features in common with arrangement 200. Arrangement 1800 is shown from a perspective defined by view lines 18-18 in FIG. 15. The view of FIG. 18 corresponds to view box 18 of FIG. 16. Arrangement 1800 may be included in fixture 112. Arrangement 1800 may include housing 1802. Housing 1802 may have one or more features in common with fixture support 116. Arrangement 1800 may include fixture 1806. Fixture 1806 may include array 1807. Array 1807 may include light-emitting diodes such as 1808.

Fixture 1806 may include platform 1814. Platform 1814 may support array 1807. Fixture 1806 may include reflector 1816. Platform 1814 may support reflector 1816. Reflector 1816 may have a "U"-shaped cross-section. The cross-section may include vertical walls 1818 and 1820. Reflector 1816 may focus light from emitter 1808 toward the upward direction.

Figure 19:
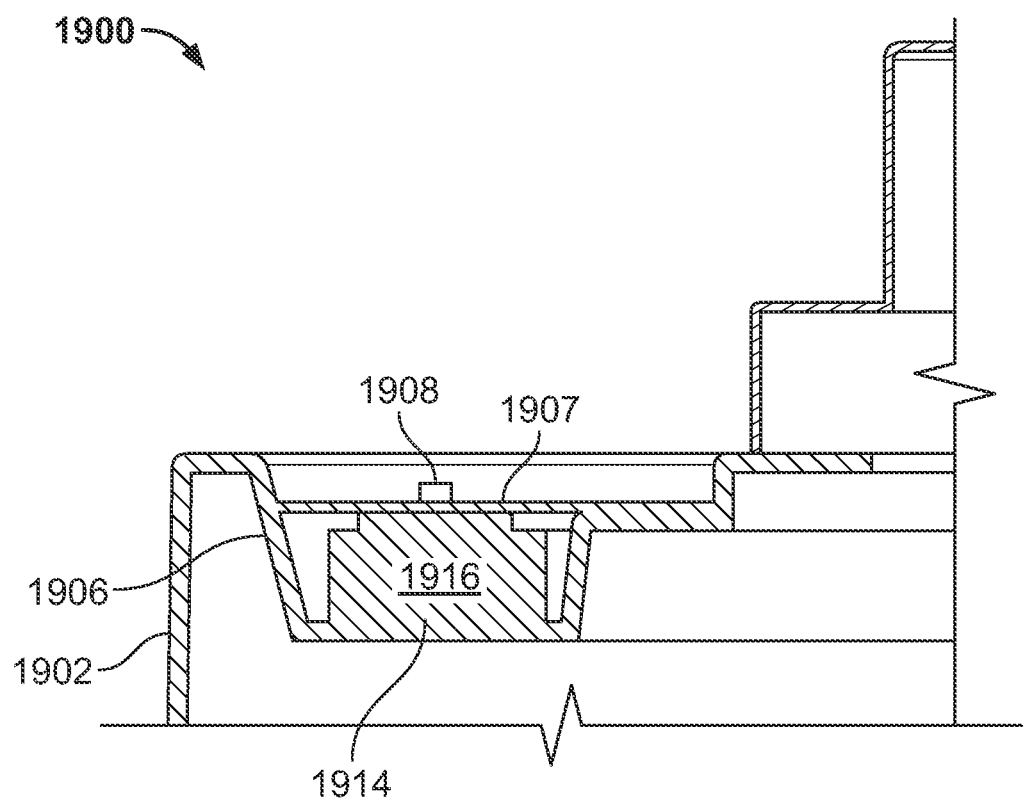
FIG. 19 shows illustrative apparatus in accordance with the principles of the invention, in a view analogous to that shown in box 19 of FIG. 16.

FIG. 19 shows in part illustrative arrangement 1900. Arrangement 1900 may have one or more features in common with arrangement 200. Arrangement 1900 is shown from a perspective defined by view lines 19-19 in FIG. 15. The view of FIG. 19 corresponds to view box 19 of FIG. 16.

Arrangement 1900 may be included in fixture 112. Arrangement 1900 may include housing 1902. Housing 1902 may have one or more features in common with fixture support 116. Arrangement 1900 may include fixture 1906. Fixture 1906 may include array 1907. Array 1907 may include light-emitting diodes such as 1908.

Fixture 1906 may include platform 1914. Platform 1914 may support array 1907. Platform 1914 may include heat sink 1916.

Figure 20:
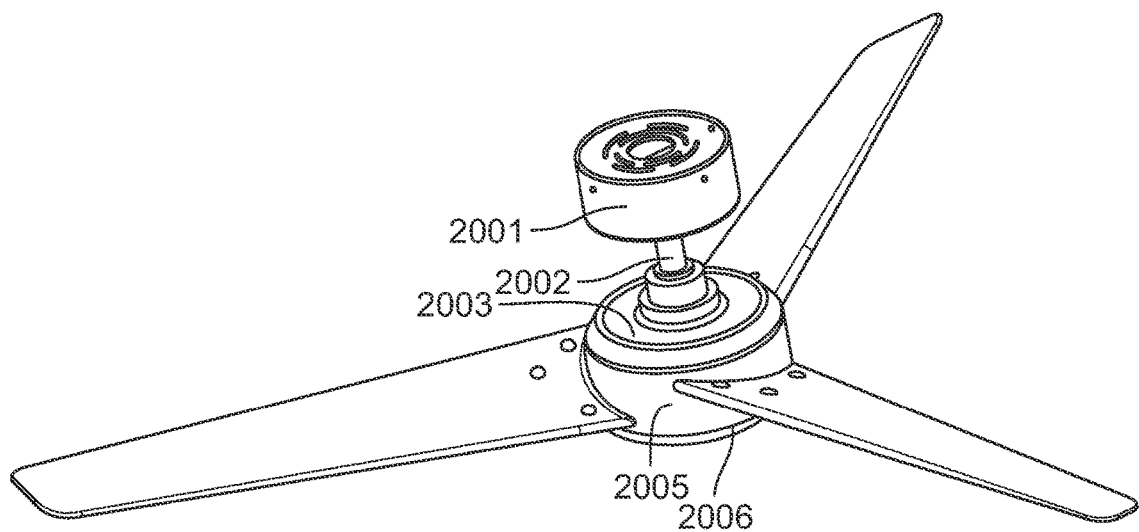
FIG. 20 shows illustrative apparatus in accordance with principles of the invention.
Figure 21:
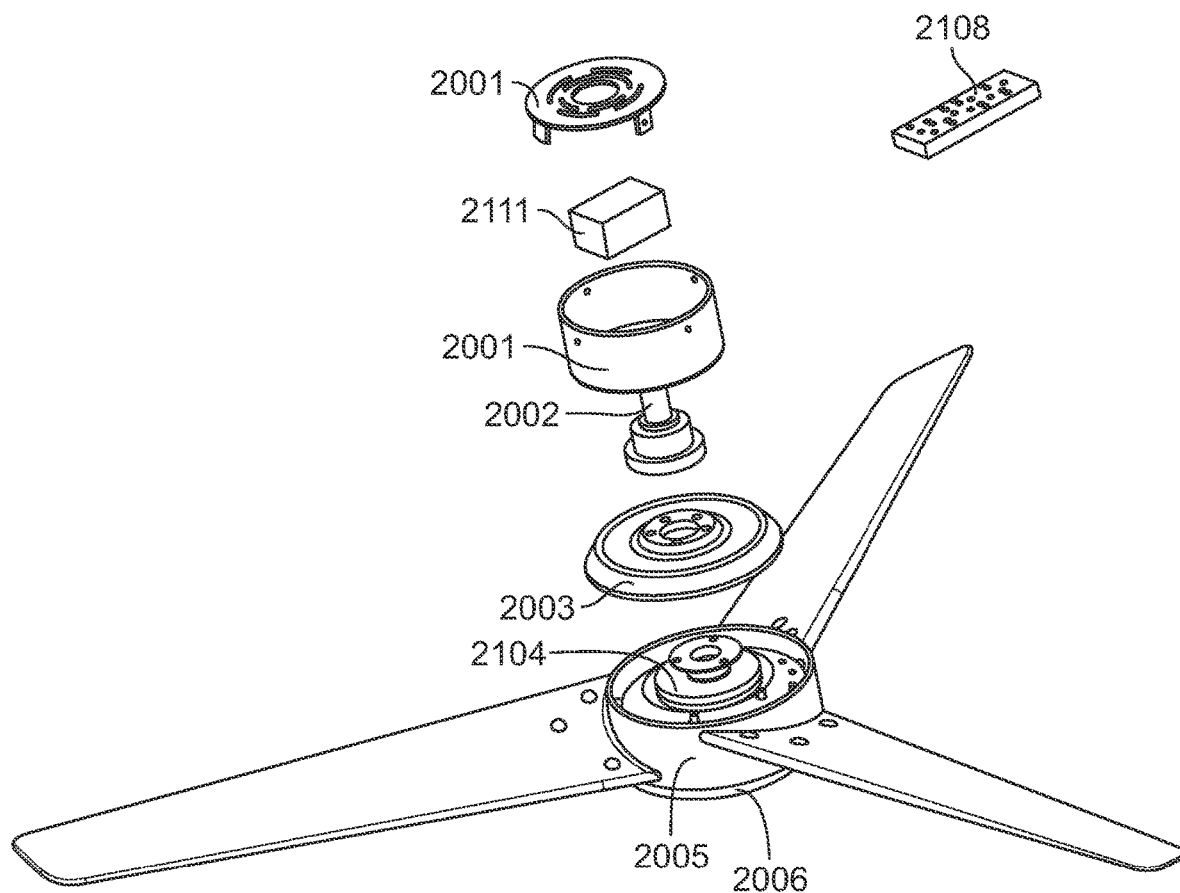
FIG. 21 shows illustrative apparatus in accordance with principles of the invention.
Figure 22:
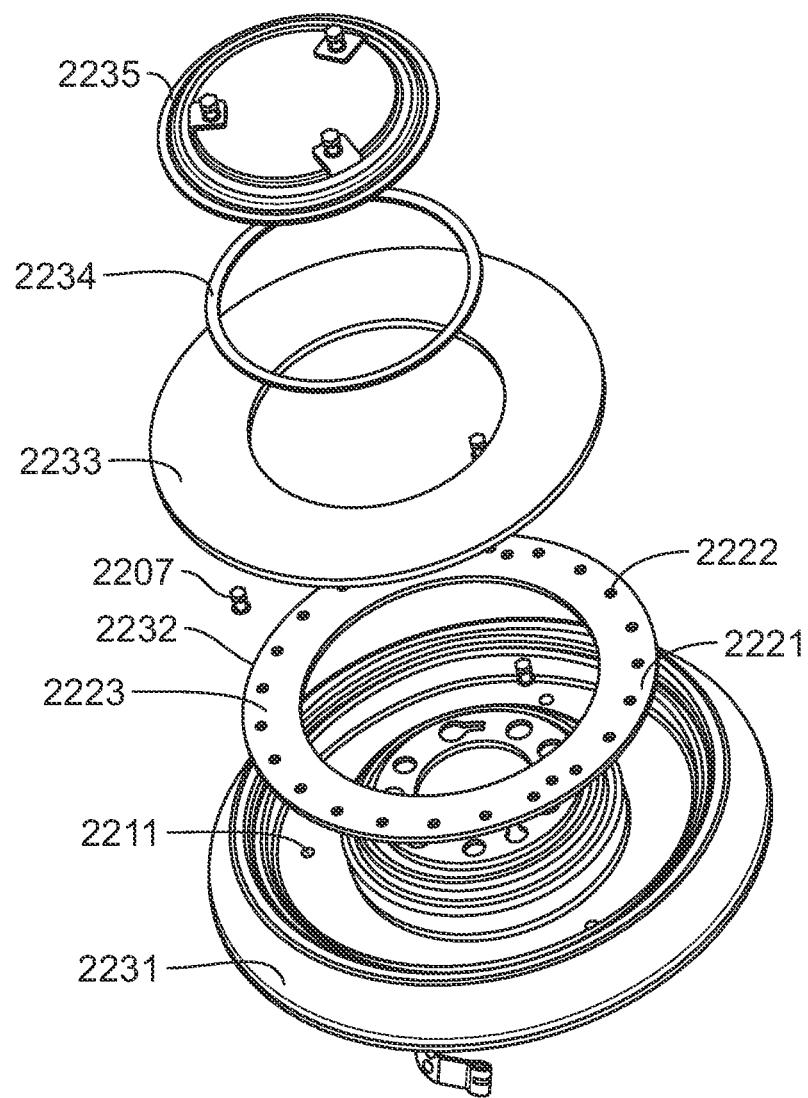
FIG. 22 shows illustrative apparatus in accordance with principles of the invention.

FIG. 20-22 show an illustrative germicidal fan lamp. The germicidal fan lamp may have one or more features in common with arrangement 200. The lamp may include a ceiling plate. The lamp may include a spindle. The lamp may include a UVC germicidal lamp assembly. The lamp may include a rotating motor. The lamp may include a rotating bladed disk (a "blisk"). An upper end of the spindle may be fixedly connected to a lower end of the ceiling plate, a lower end of the spindle may be fixedly connected to a stator end of the rotating motor. The rotating blisk may be installed on a rotor end of the rotating motor. The UVC germicidal lamp assembly may be provided over the spindle and arranged above the rotating motor.

The UVC germicidal lamp may emit light upwards.

Blisk 2005 may cycle through forward and reverse rotations to pass air through light from the UVC germicidal lamp for sterilization of the air. After sterilization, the UVC germicidal lamp assembly may be turned off, but rotating blisk 2005 may remain powered to circulate air in environment E.

The UVC germicidal lamp assembly may include chassis 2231. The UVC germicidal lamp assembly may include UVC LED module 2232. The UVC germicidal lamp assembly may include quartz glass 2233. The UVC germicidal lamp assembly may include cushion 2234. The UVC germicidal lamp assembly may include fixing plate 2235. Chassis 2231, UVC LED module 2232, quartz glass 2233, cushion 2234 and fixing plate 2235 may be arranged from bottom to top. UVC LED module 2232 may be installed at an upper end of chassis 2231. Quartz glass 2233 may cover an upper surface of UVC LED module 2232. Upper and lower ends of cushion 2234 may be pressed against fixing plate 2235 and the quartz glass 2233, respectively. One or more of chassis 2231, UVC LED module 2232, quartz glass 2233, cushion 2234, and fixing plate 2235 may include a through hole. A mounting component may be arranged on an inner side of fixing plate 2235 and fixedly connected to chassis 2231. Chassis 2231 may be fixedly connected to the stator end of rotating motor 2104.

Quartz glass 2233 may have high UVC transmittance (above 90% transmittance). Quartz glass 2233 may be arranged to protect UVC LED module 2232. Since glue may fail under ultraviolet radiation, UVC germicidal lamp assembly 2003 may include mechanical fixation of quartz glass 2233. Quartz glass 2233 may be pressed tightly on UVC LED module 2232 through fixing plate 2235. This may effect the fixation. Cushion 2234 may be arranged between fixing plate 2235 and quartz glass 2233. This may prevent quartz glass 2233 from fracture due to excessive pressure. One or more of chassis 2231, UVC LED module 2232, quartz glass 2233, cushion 2234, and fixing plate 2235 may include a through hole for spindle 2002 to pass through.

UVC LED module 2232 may include substrate 2221. UVC LED module 2232 may include a plurality of LED lamp slices 2222. Lamp slices 2222 may be arranged on substrate 2221. Light emitted by LED lamp slice 2222 may have a wavelength in the range 200 to 280 nm. Light radiation in this range of wavelengths may act on microorganisms (bacteria, viruses, spores, and other pathogens), breaks molecular structures of DNA and RNA in cells of the microorganisms, cause breakage of DNA chains and cross-linking damage of nucleic acid and protein, and may cause death of growth cells and regenerative cells, thereby effecting disinfection and sterilization.

Substrate 2221 may include a plurality of first mounting holes 2223. Chassis 2231 include a plurality of second mounting holes 2211 at positions corresponding to the first mounting holes 2223. Fasteners 2207 may be inserted into first mounting holes 2223 and second mounting holes 2211. First mounting holes 2223 and second mounting holes 2211 may be aligned with each other. Fixed connection between substrate 2221 and chassis 2231 through fasteners 2207 may stabilize the position of the UVC LED module 2232, reduce vibration, and reduce or avoid damage to UVC LED module 2232 from vibration.

The fasteners 2207 may be screws.

Signal receiver 2111 may be arranged in ceiling plate 2001. One or both of UVC germicidal lamp assembly 2003 and rotating motor 2104 may be electrically connected to signal receiver 2111. Signal receiver 2111 may be configured to receive a control signal from controller 2108 to control turning on of UVC germicidal lamp assembly 2003, turning on rotating motor 2104, a rotating direction of rotating motor 2104, and the like.

LED lighting module 2006 may be installed at a lower end of blisk 2005, and may provide a lighting function. LED lighting module 2006 may be electrically connected to signal receiver 2111. LED lighting module 2006 may be independently controlled by the controller 2108.

Figure 23:
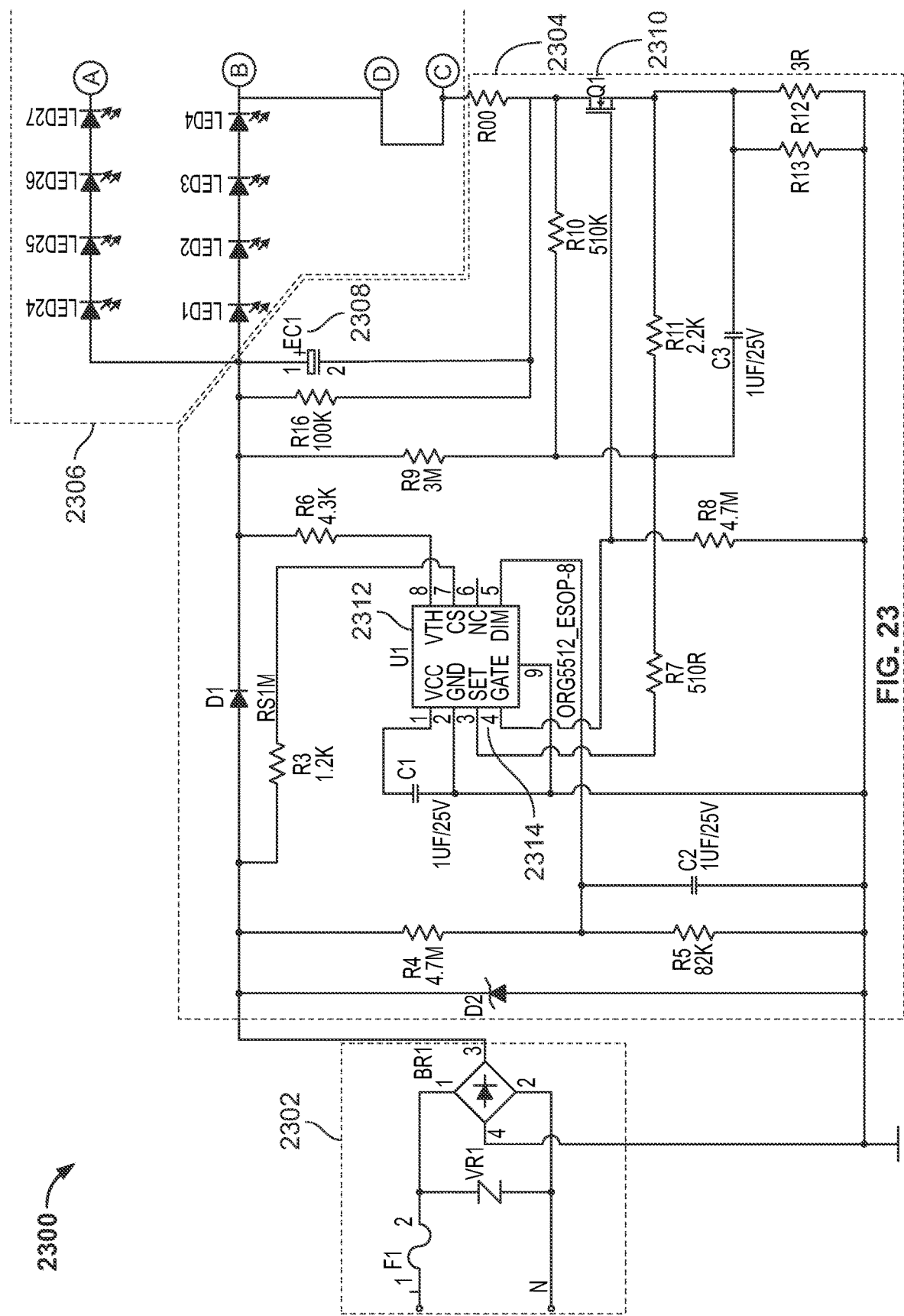
FIG. 23 shows schematically illustrative apparatus in accordance with principles of the invention.
Figure 23:
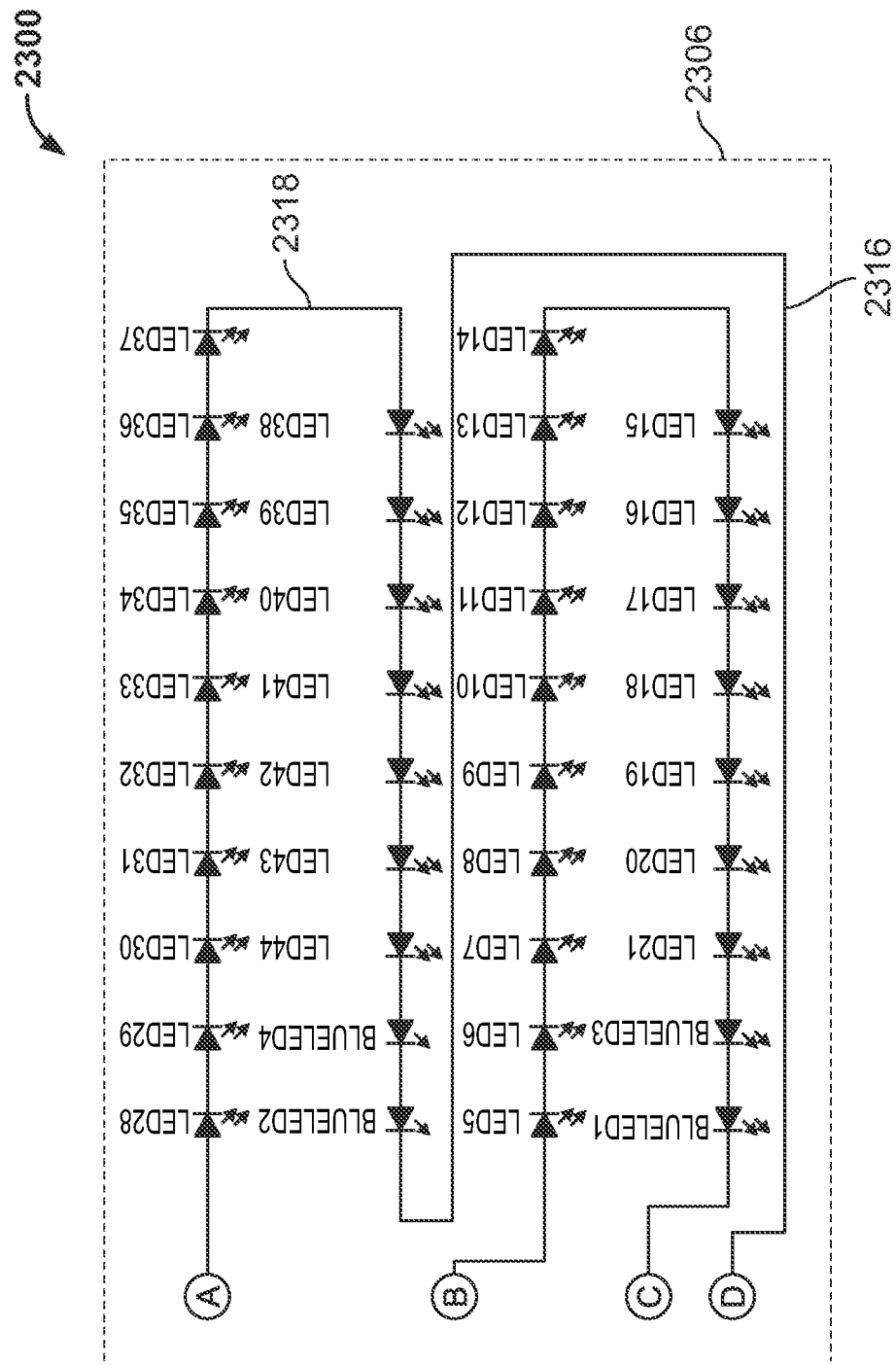

FIG. 23 shows illustrative circuit 2300 for an array such as 210. Circuit 2300 may be an AC LED circuit. Circuit 2300 may include rectifier 2302. Circuit 2300 may include AC power supply 2304. Circuit 2300 may include LED circuit 2306.

Rectifier 2302 may receive a 120 VAC line input. Rectifier 2302 may output to power supply 2304 a full-wave rectified voltage having a voltage such as 170 V. Power supply 2304 may receive the voltage, and may provide it to LED circuit 2306 as incremental DC voltages. Capacitor EC1 2008 may maintain any ripple current voltage at no more than 20% of the voltage output from power supply 2304. Switch Q1 2310 may open and close to allow increments of current to flow through LED circuit 2304. Microcontroller U1 2312, via gate pin 4 2314 may trigger switch Q1 2310 to provide the incremental current to flow through LED circuit 2304. LED circuit 2304 may include LED string 2316. LED string 2316 may include UV-C LEDs LED1-LED21. LED string 2316 may include visible light (e.g., one or more of red, green, blue and any other suitable color) LEDs Blue LED3 and Blue LED1.

LED circuit 2304 may include LED string 2318. LED string 2318 may include UV-C LEDs LED24-LED44. LED string 2318 may include visible light (e.g., one or more of red, green, blue and any other suitable color) LEDs Blue LED4 and Blue LED2.

Strings 2316 and 2318 may be wired in parallel. Strings 2316 and 2318 may be wired in series.

The visible light LEDs may be in line with strings 2316 and 2318. The visible LEDs may be controlled by microcontroller U1 2312 separately from the control of the UV-C LEDs.

Figure 24:
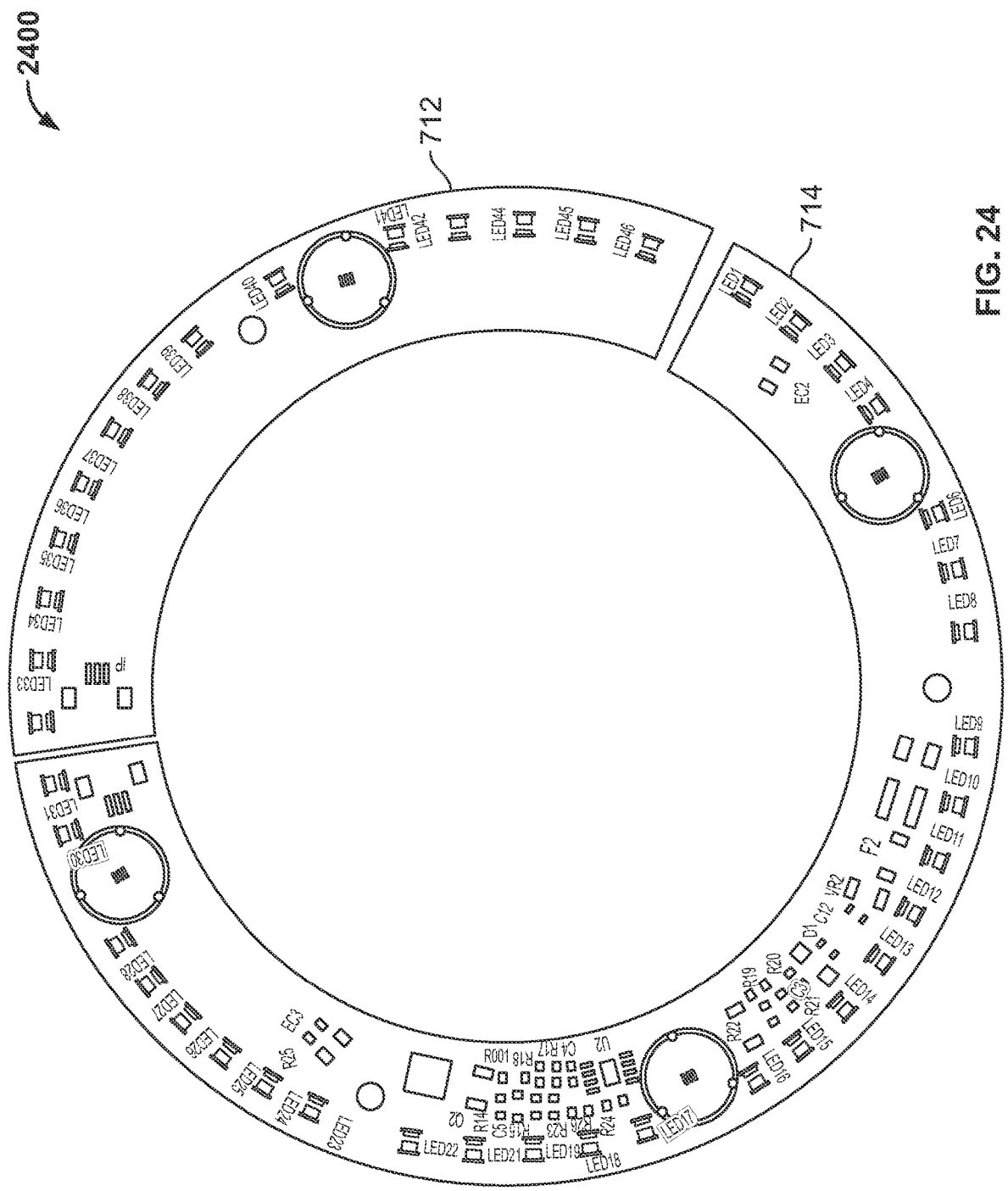
FIG. 24 shows illustrative apparatus in accordance with principles of the invention.

FIG. 24 shows an illustrative printed circuit board ("PCB") layout 2400 that may be implemented for a circuit such as 2300. Layout 2400 may include segment 712. Layout 2400 may include segment 714.

Figure 25:
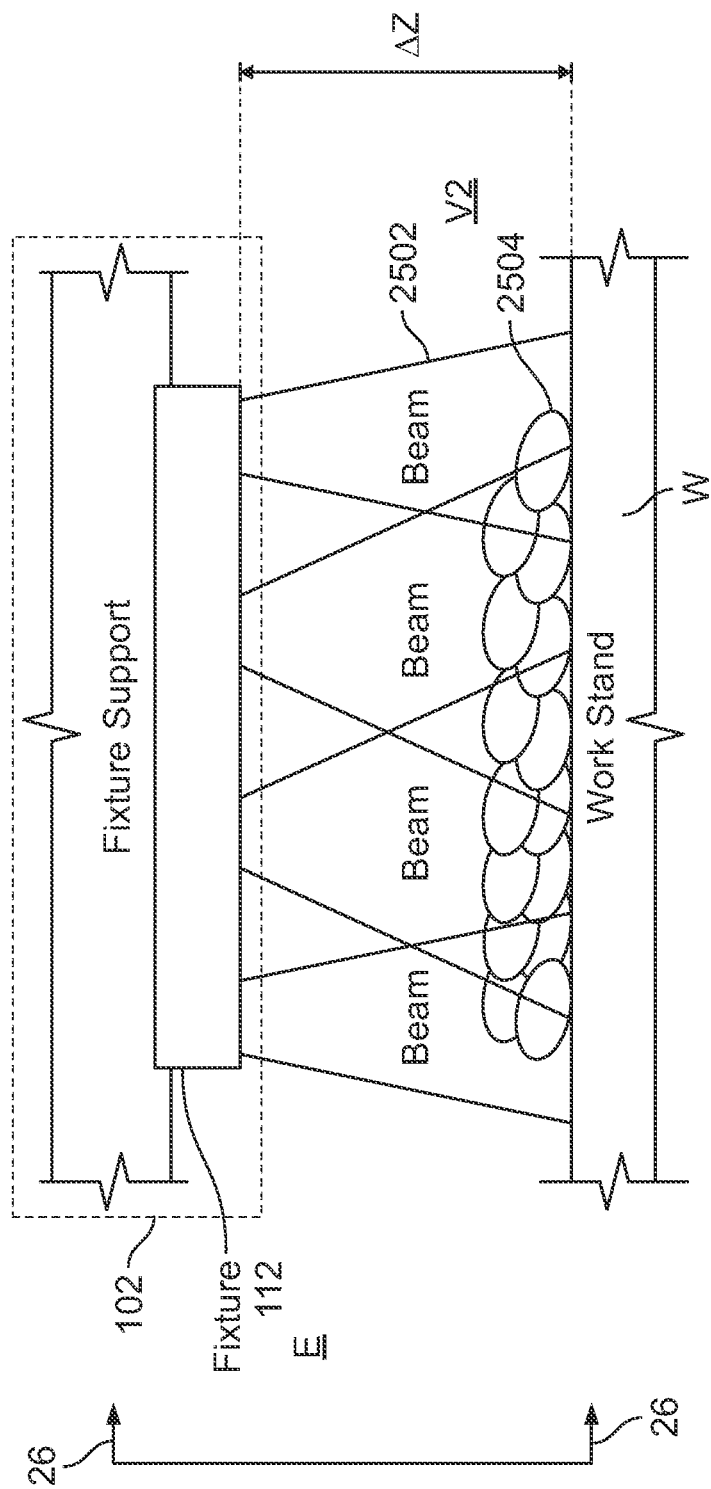
FIG. 25 shows schematically illustrative apparatus in accordance with principles of the invention.

FIG. 25 shows part of illustrative architecture 100 along with light 2502 emitted, in the aggregate, from emitters of fixture 112 and items 2504. Light 2502 is incident on items 2504.

FIG. 26 shows two views of a schematic arrangement that corresponds to apparatus shown in FIG. 25. View 2602 corresponds to a view taken along lines 26-26 (shown in FIG. 25). View 2604 corresponds to the view shown in FIG. 25.

Structure $S_{26}$ may correspond to structure S. Work stand $W_{26}$ may correspond to work stand W. One or both of structure $S_{26}$ work stand $W_{26}$ may include all some of partition P.

Table 16 lists illustrative ranges that may include values of height $\Delta z$, of fixture 2606, above work stand $W_{26}$, d, the horizontal depth of work stand $W_{26}$, and c, a horizontal length along partition $P_{26}$ that is to be illuminated by a single fixture such as 2606, of work stand $W_{26}$.

TABLE 16

Illustrative ranges that may include values of $\Delta z$, d and c

| $\Delta z$ (in.) Range | | d (in.) Range | | c (in.) Range | |
| --- | --- | --- | --- | --- | --- |
| Lower | Upper | Lower | Upper | Lower | Upper |
| <6 | 6 | <6 | 6 | <6 | 6 |
| 6 | 12 | 6 | 12 | 6 | 12 |
| 12 | 18 | 12 | 18 | 12 | 18 |
| 18 | 24 | 18 | 24 | 18 | 24 |
| 24 | 30 | 24 | 30 | 24 | 30 |
| 30 | 36 | 30 | 36 | 30 | 36 |
| 36 | 42 | 36 | 42 | 36 | 42 |
| 42 | 48 | 42 | 48 | 42 | 48 |
| 48 | 54 | 48 | 54 | 48 | 54 |
| 54 | 60 | 54 | 60 | 54 | 60 |
| 60 | 66 | 60 | 66 | 60 | 66 |
| 66 | 72 | 66 | 72 | 66 | 72 |
| 72 | 78 | 72 | 78 | 72 | 78 |
| 78 | 84 | 78 | 84 | 78 | 84 |
| 84 | 90 | 84 | 90 | 84 | 90 |
| 90 | 96 | 90 | 96 | 90 | 96 |
| 96 | >96 | 96 | >96 | 96 | >96 |

Other suitable ranges that may include illumination intensity of array 210

Fixture 2606 may have one or more features in common with fixture 102. Fixture 2606 may propagate light 2502 onto work stand $W_{26}$. Partition P may block light 2502. Fixture 2606 may limit light 2502 to be propagated within an angle α of partition P. Light 2502 may define a beam. The beam may have edge 2608. Edge 2608 may be defined as having half the light intensity of the maximum intensity of the beam. Edge 2608 may be detected by optical goniometry. Edge 2608 may lie at angle α. Table 17 lists illustrative ranges that may include α.

TABLE 17

Illustrative values of α (°) Range

| Lower | Upper |
| --- | --- |
| <15 | 15 |
| 15 | 20 |
| 20 | 25 |
| 25 | 30 |
| 30 | 35 |
| 35 | 40 |
| 40 | 45 |

TABLE 17-continued

Illustrative values of α (°) Range

| Lower | Upper |
| --- | --- |
| 45 | 50 |
| 50 | 55 |
| 55 | 60 |
| 60 | 65 |
| 65 | 70 |
| 70 | 75 |
| 75 | >75 |

Other suitable ranges that may values of α

Fixture 2606 may have width f. Fixture 2606 may limit light 2502 to be propagated within an angle γ with respect to vertical V and spanning along partition P. The beam may have edge 2610. Edge 2610 may be defined as having half the light intensity of the maximum intensity of the beam. Edge 2610 may be detected by optical goniometry. Edge 2610 may lie at angle γ. Table 18 lists illustrative ranges that may include γ.

TABLE 18

Illustrative ranges that may include γ Range

| Lower | Upper |
| --- | --- |
| <15 | 15 |
| 15 | 20 |
| 20 | 25 |
| 25 | 30 |
| 30 | 35 |
| 35 | 40 |
| 40 | 45 |
| 45 | 50 |
| 50 | 55 |
| 55 | 60 |
| 60 | 65 |
| 65 | 70 |
| 70 | 75 |
| 75 | >75 |

Other suitable ranges that may include γ

When $\Delta z$ is in the range 18"-24", and f is 12", light 2502 may cover 36" along work stand $W_{26}$.

Figure 27:
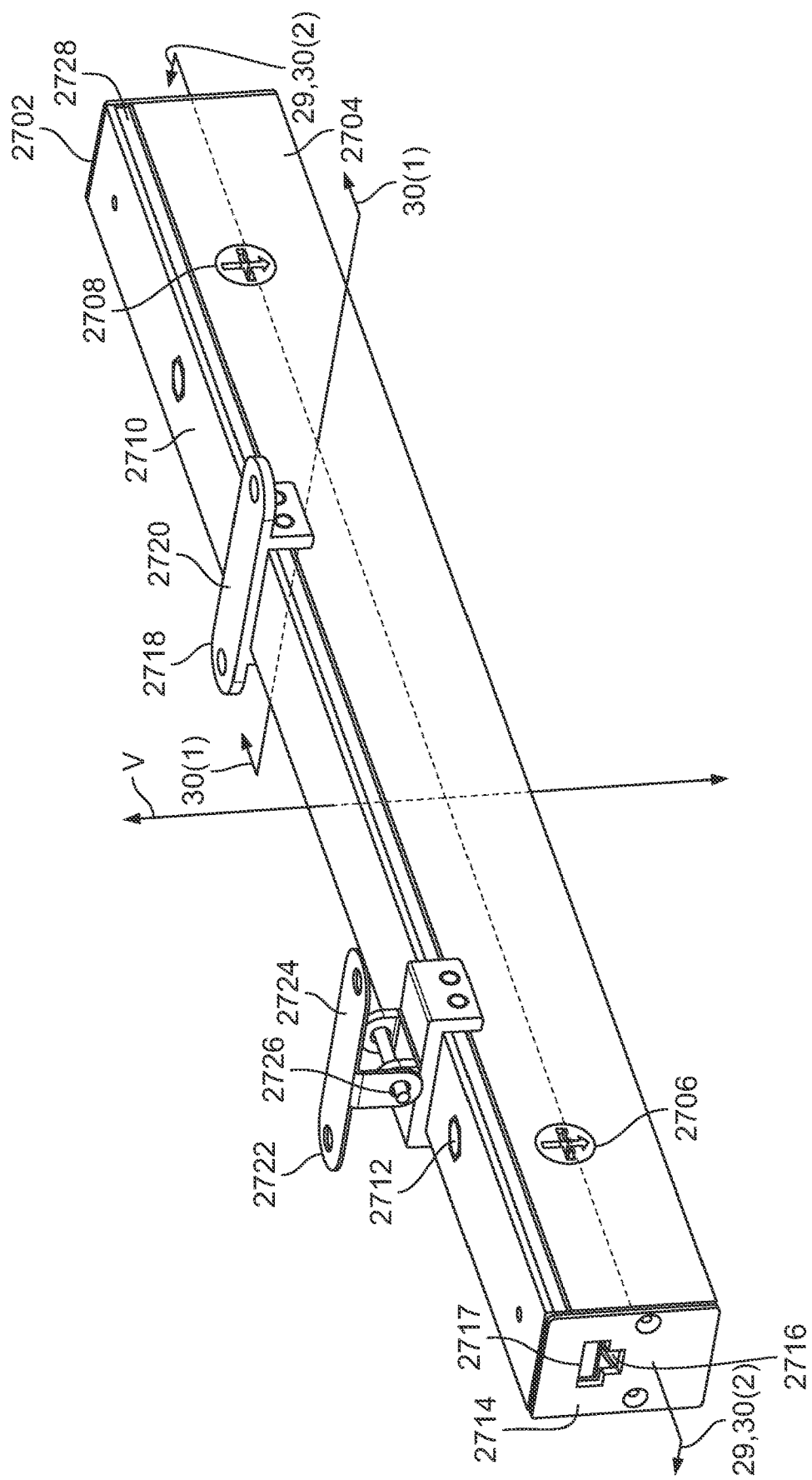
FIG. 27 shows illustrative apparatus in accordance with principles of the invention.

FIG. 27 shows illustrative fixture 2702. Fixture 2702 may have one or more features in common with fixture 102. Fixture 2702 may include housing 2704. Housing 2704 may include aluminum. Housing 2704 may define an internal channel (not shown). The internal channel may house a germicidal emitter array (not shown). The internal channel may house a marker emitter (not shown) that emits light in the visual spectrum. The internal channel may include a light-absorptive coating (not shown). The light-absorptive coating may include black paint. Fixture 2702 may include a lower face (not shown) through which light is propagated.

Fixture 2702 may include delay-time control shaft 2706. A user may rotate control shaft 2706 to set a delay time for fixture 2702. The delay time may be a time after which fixture 2702 will begin to emit light. The delay may provide for a user to exit the area in which the fixture is located, if desired, before the fixture turns on.

Fixture 2702 may include ON-time control shaft 2708. A user may rotate control shaft 2708 to set an ON-time time for fixture 2702. The ON-time may be a duration of time during which fixture 2702 is programmed to emit light.

Housing 2704 may include spine 2710. Fasteners such as 2712 may support one or both of the emitter arrays.

Housing 2704 may include end plates such as 2714.

Fixture 2702 may include connectors such as 2716. Connector 2716 may connect with a cable (not shown). The cable may provide power to fixture 2702. The cable may provide communication between fixture 2702 and a fixture controller (not shown). Fixture 2702 may include ports such as 2717 to receive a connector on a cable end. The connector may be a quick-connect type connector. Using the connectors, fixtures such as 2702 may be daisy-chained together with other such fixtures, with other types of fixtures, with sensors, control modules, communication networks and the like. A motion sensor may thus be used to turn off a run of fixtures. The motion sensor may be located in a strategic location, such as a doorway, hallway, or entranceway to a room or closet in which the fixture or run of fixtures is located. The fixture or fixtures may thus be turned off in advance of the arrival of a person, animal or other object.

Fixture 2702 may be attached to a structure such as S by a bracket such as 2718. Mounting surface 2720 may be oriented at an angle, with respect to spine 2710, that is fixed. Fixture 2702 may be attached to the structure by a bracket such as 2722. Bracket 2722 may include mounting surface 2724. Mounting surface 2724 may be oriented at an angle, with respect to spine 2710, that is adjustable by pivoting mounting surface 2724 about pin 2726. The brackets may be attached to fixture 2702 and to the structure with suitable fasteners. The fasteners may engage fixture 2702 in recess 2728 and another recess (not shown) on the opposite side of fixture 2702.

Figure 28:
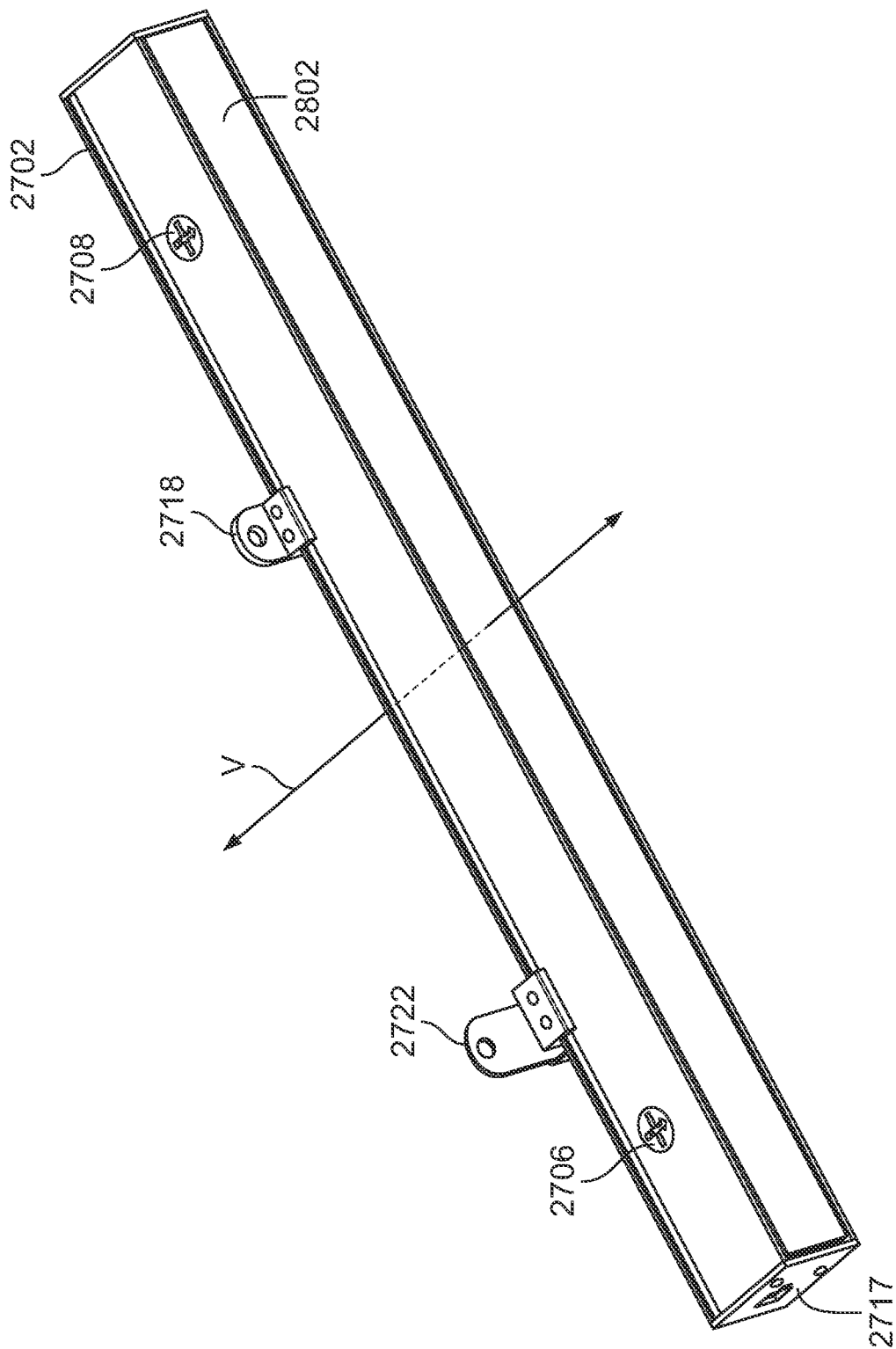
FIG. 28 shows illustrative apparatus in accordance with principles of the invention.

FIG. 28 shows fixture 2702 from a perspective different from that shown in FIG. 27. Fixture 2702 may include diffuser 2802. Diffuser 2802 may be transmissive of UV-C light. Diffuser 2802 may include quartz glass.

Figure 29:
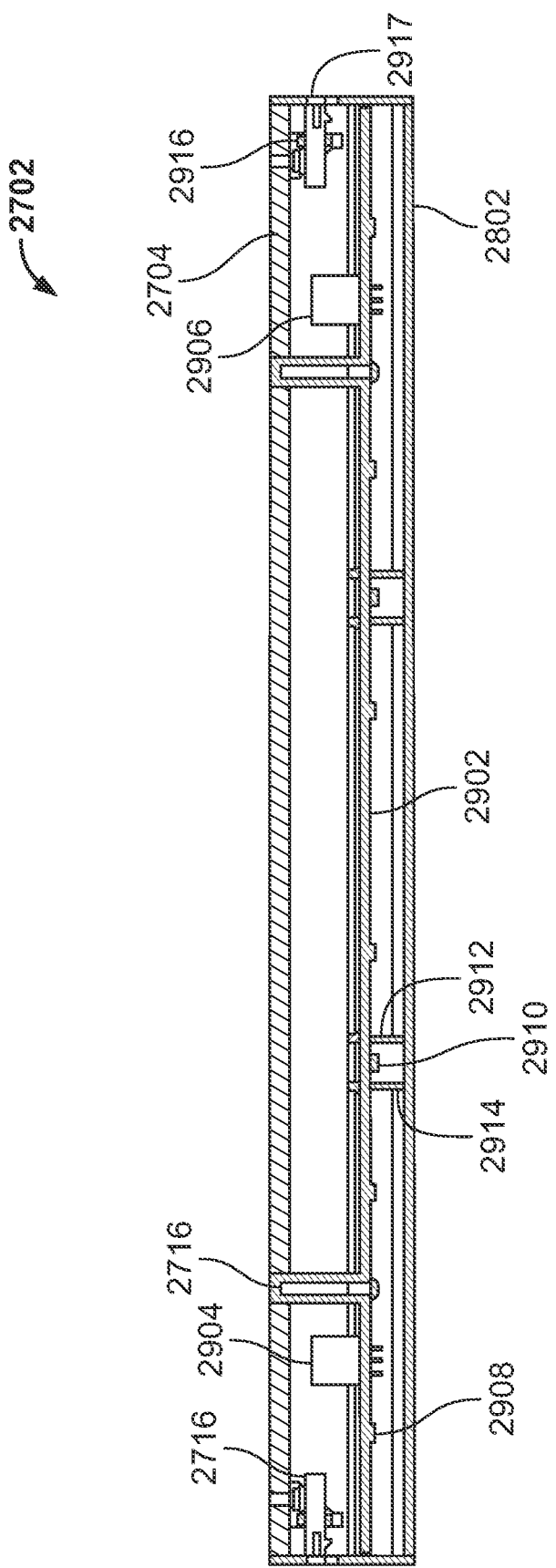
FIG. 29 is a partial cross-section taken along view lines 29-29 of FIG. 27.

FIG. 29 shows a partial view of fixture 2702 taken along lines 29-29 (shown in FIG. 27). Circuit board 2902 may support rotational switch circuit 2904. Circuit board 2902 may support rotational switch circuit 2906. Rotational switch circuit 2904 may be actuated by shaft 2706. Rotational switch circuit 2906 may be actuated by shaft 2708. Circuit board 2902 may support a germicidal light-emitting diode such as 2908. Circuit board 2902 may support a visual spectrum light-emitting diode such as 2910. Germicidal light-emitting diodes may be disposed in cans such as 2912. Hat 2912 may concentrate visual spectrum light in a region of diffuser 2802. Hat 2912 may include lower lip 2914. Lower lip 2914 may be disposed flush against diffuser 2802.

Fixture 2702 may include connector 2916. Connector 2916 may connect with a cable (not shown). The cable may provide power to fixture 2702. The cable may provide communication between fixture 2702 and a fixture controller (not shown). Fixture 2702 may include ports such as 2917 to receive a connector on a cable end.

Figure 30:
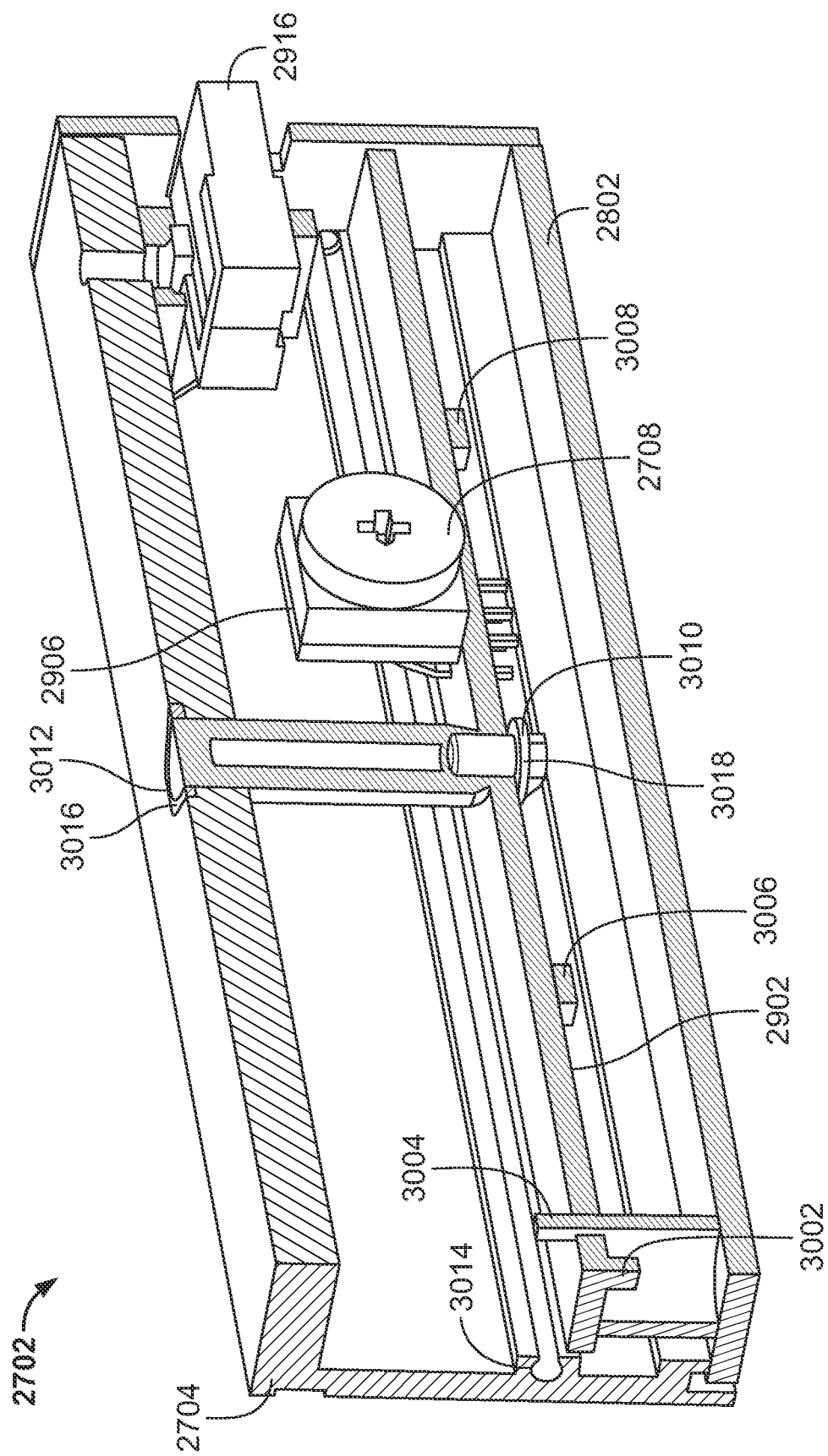
FIG. 30 is a partial cross-section taken along view lines 30(1)-30(1) and 30(2)-30(2) of FIG. 27.

FIG. 30 shows a partial view of fixture 2702 taken along lines 30(1)-30(1) and 30(2)-30(2) (shown in FIG. 27). Fixture 2702 may include visual spectrum emitter 3002. Emitter 3002 may be disposed in hat 3004. Hat 3004 may be mounted on circuit board 2902. Fixture 2702 may include germicidal emitter 3006. Fixture 2702 may include germicidal emitter 3008. Fastener 3010 may be anchored in fastener 3012. Fastener 3012 may be anchored in spine 2710 against movement along vertical V. Channel 3014 in housing 2704 may include an insert (not shown). The insert may counteract upward vertical motion of circuit board 2902. The insert may include polymer. The insert may maintain tension between head 3016 of fastener 3012 and head 3018 of faster 3010. Head 3016 may be countersunk is spine 2710.

Figure 31:
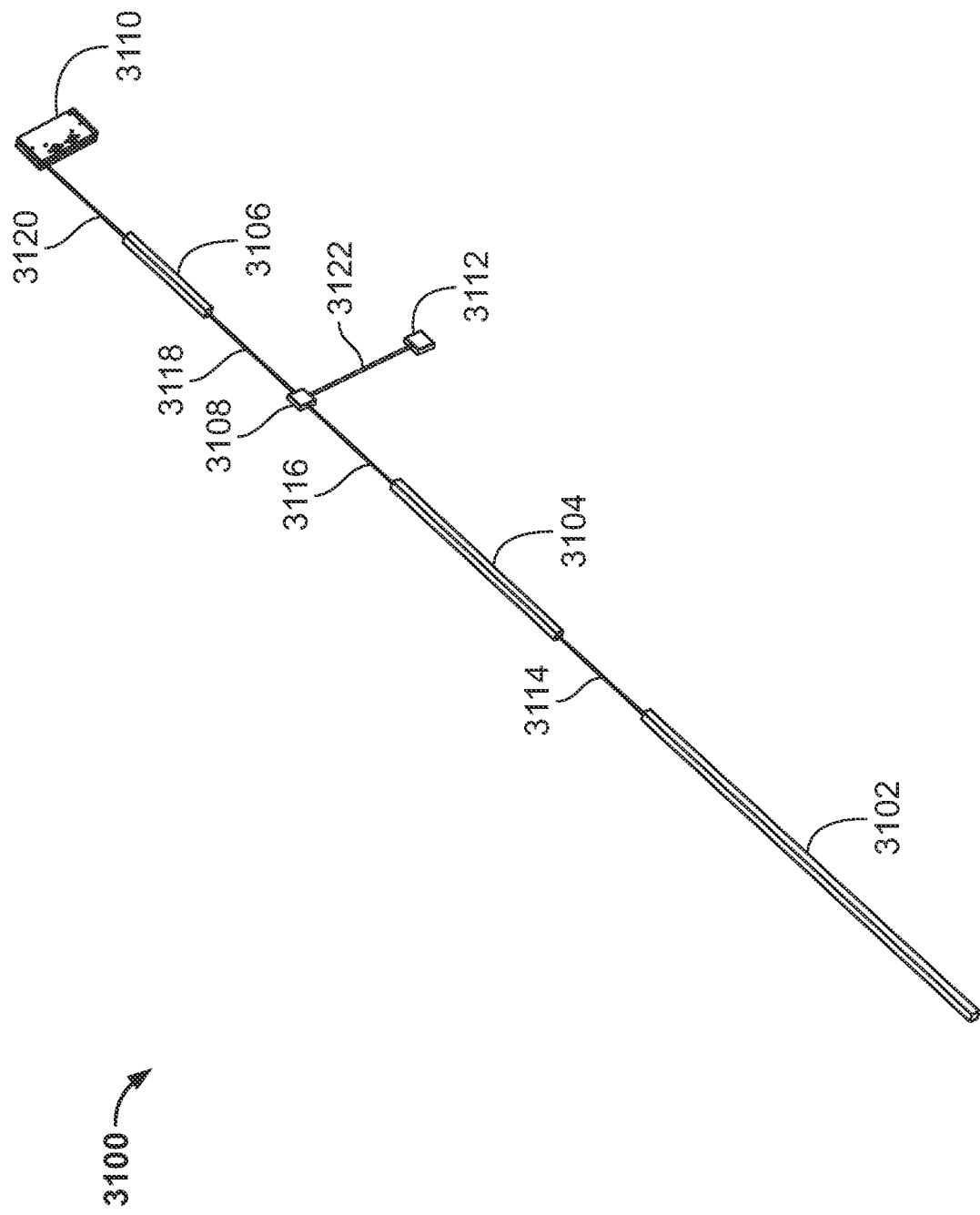
FIG. 31 shows illustrative apparatus in accordance with principles of the invention.

FIG. 31 shows illustrative arrangement 3100. Arrangement 3100 may include fixture 3102. Arrangement 3100 may include fixture 3104. Arrangement 3100 may include fixture 3106. One or more of the fixtures may have one or more features in common with fixture 112. The fixtures may have different lengths. For example, fixtures 3102, 3104 and 3106 may have lengths of 12", 24" and 36", respectively. Arrangement 3100 may include junction box 3108. Arrangement 3100 may include power and communication box 3110. Arrangement 3100 may include motion sensor 3112. Arrangement 3100 may include cables 3114, 3116, 3118, 3120, 3122 and any other suitable cables. The cables may be configured to provide power to the fixtures. The cables may be configured to transmit communication signals. The cables may include connectors that mate with complementary connectors in the fixtures. Arrangement 3100 may include brackets (not shown) for attachment to a structure such as S of fixtures 3102, 3104, 3106, junction box 3108, electrical box 3110 and motion sensor 3112. Electrical box 3110 may be in electrical communication with a power source (not shown) outside arrangement 3100. Electrical box 3110 may be in electrical communication with control circuits (not shown) outside arrangement 3100. Electrical box 3110 may include a power supply for emitters in the fixture.

Figure 32:
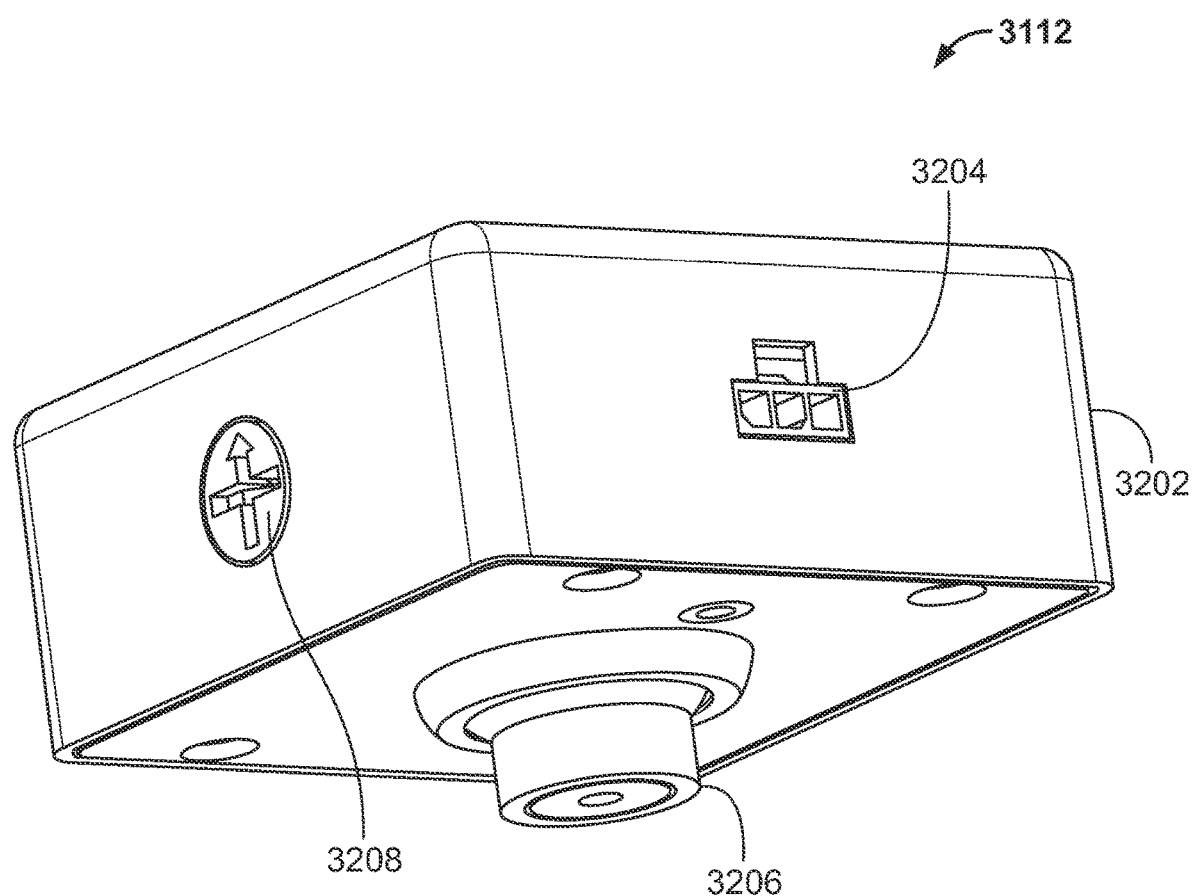
FIG. 32 shows illustrative apparatus in accordance with principles of the invention.

FIG. 32 shows illustrative motion sensor 3112. Motion sensor 3112 may include cover 3202. Motion sensor 3112 may include connector 3204 for connection with a cable such as 3124. Motion sensor 3112 may include sensor 3206. Sensor 3206 may operate by passively sensing IR radiation, emitting, and detecting reflections of, microwave radiation, emitting, and detecting reflections of, ultrasonic energy, or by any other suitable approach. Motion sensor 3112 may include sensitivity-control shaft 3208.

Figure 33:
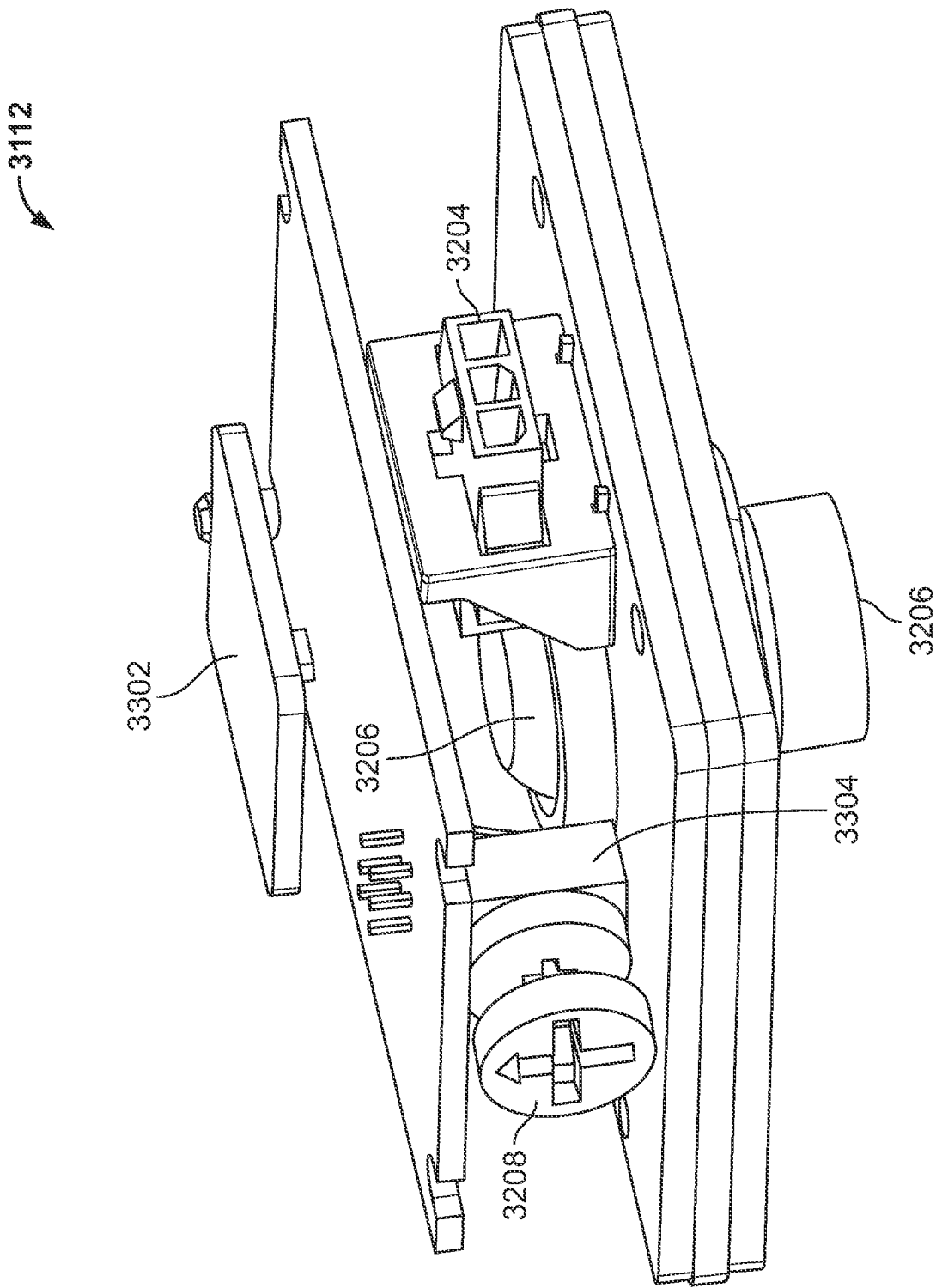
FIG. 33 shows illustrative apparatus in accordance with principles of the invention.

FIG. 33 shows motion sensor 3112 without cover 3202. Motion sensor 3112 may include circuit board 3302. Shaft 3208 may control rotary switch 3304. Circuit board 3302 may be in electrical communication (via conductors, not shown) with connector 3204, sensor 3206 and rotary switch 3304. In operation, motion sensor 3112 may detect motion of a living body in environment E. If the motion exceeds a threshold set by rotary switch 3304, a circuit (not shown) may transmit a communication via connector 3204 to a fixture control circuit (not shown) that is configured to switch OFF one or more of the fixtures.

Figure 34:
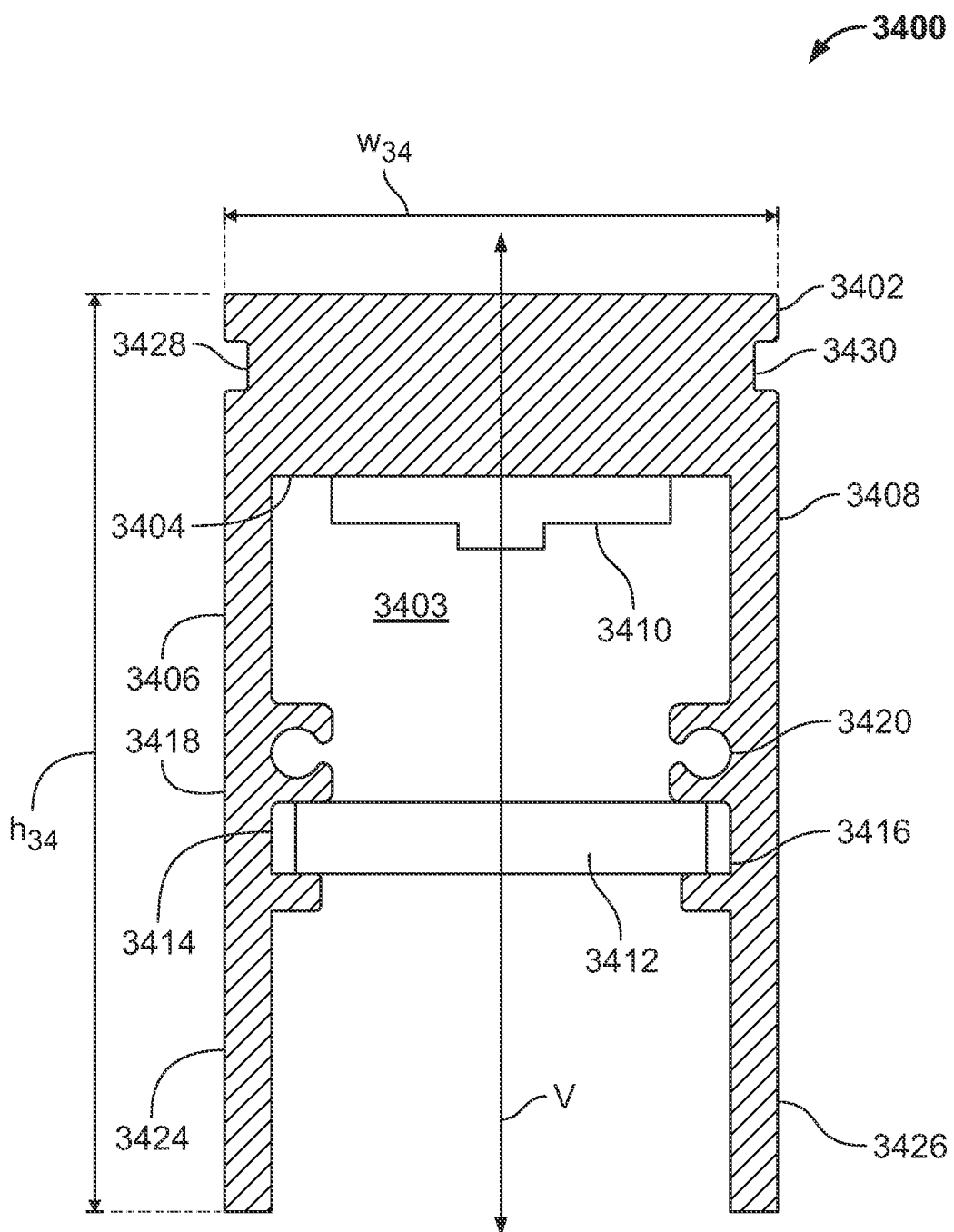
FIG. 34 shows an illustrative apparatus in accordance with principles of the invention in a view analogous to that taken along view lines 30(1)-30(1) of FIG. 27.

FIG. 34 shows schematically a view analogous to that taken along view lines 30-30 (shown in FIG. 27) of fixture 2702 of illustrative fixture 3400. Fixture 3400 may have one or more features in common with fixture 112. Fixture 3400 may include housing 3402. Housing 3402 may include aluminum. Housing 3402 may include interior 3403. Interior 3403 may have a light-absorptive coating (not shown). The coating may be black. The coating may include paint. Housing 3402 may include web 3404. Housing 3402 may include side 3406. Housing 3402 may include side 3408. Fixture 3400 may include emitter array 3410. Emitter array 3410 may include germicidal emitters. Emitter array 3410 may include visible spectrum emitters. Emitter array 3410 array may be mounted on web 3404. Fixture 3400 may include diffuser 3412. Diffuser 3412 may include quartz glass. Sides 3406 and 3408 may include, respectively, channels 3414 and 3416. Channels 3414 and 3416 may secure diffuser 3412. Sides 3406 and 3408 may include, respectively, "C"-slots 3418 and 3420. "C"-slots 3418 and 3420 may secure a seal (not shown). The seal may reduce or prevent infiltration of particles or moisture into interior 3403 of housing 3402.

Sides 3406 and 3408 may include, respectively, extensions 3424 and 3426. The extensions may limit the spread of light propagating from emitter array 3410.

Sides 3406 and 3408 may include, respectively, recesses 3428 and 3430. Recesses 3428 and 3430 may receive protrusions extending from a mounting bracket (not shown) for mounting to a structure such as S.

Width $w_{31}$ may be 0.91" or any other suitable width. Height $h_{31}$ may be 1.5" or any other suitable height.

Figure 35:
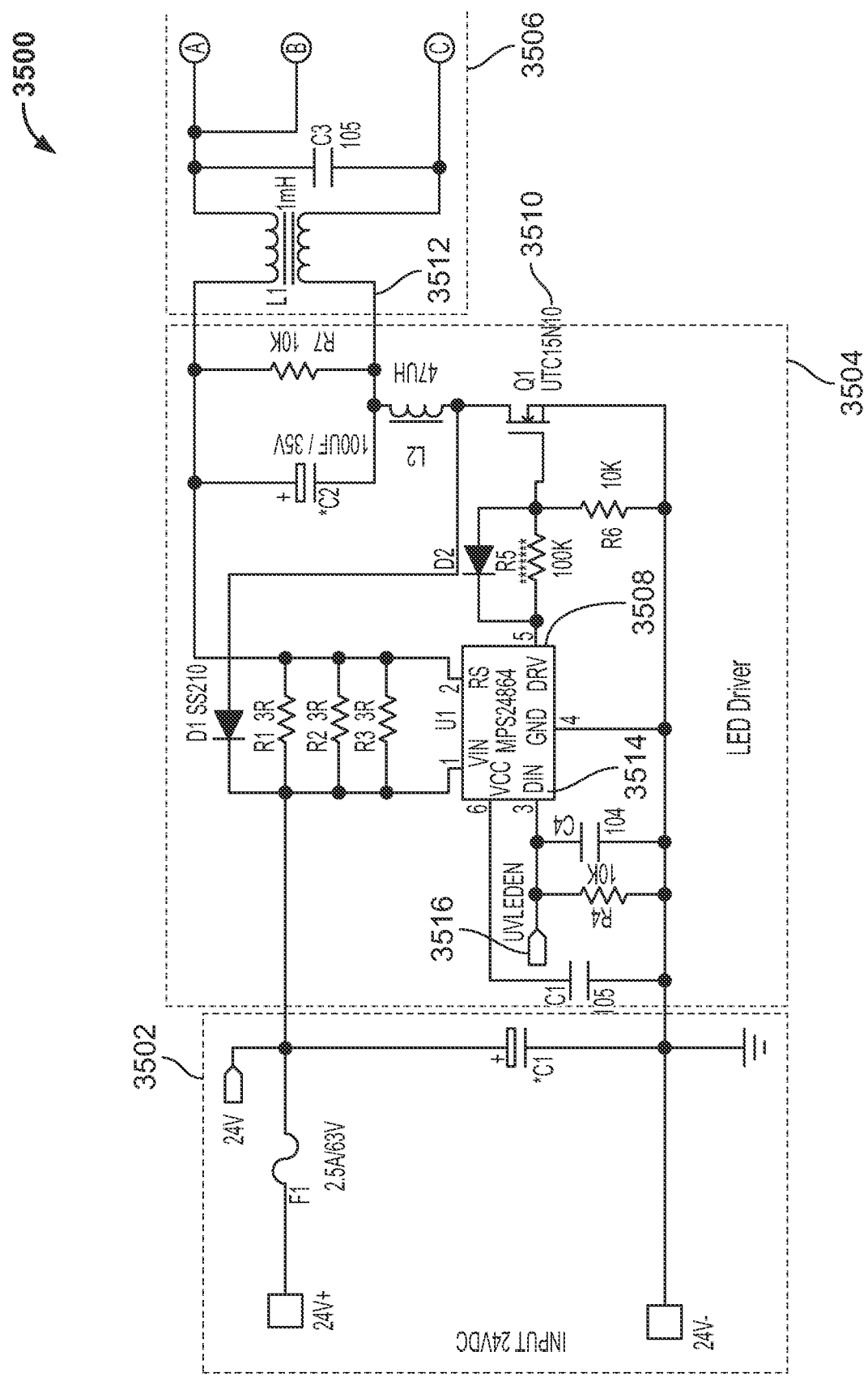
FIG. 35 shows schematically illustrative apparatus in accordance with principles of the invention.

FIG. 35 shows schematically illustrative circuit 3500 for providing germicidal lighting. Circuit 3500 may include power conditioning module 3502. Circuit 3500 may include LED driver module 3504. Circuit 3500 may include germicidal emitter array 3506.

Power conditioning module 3502 may receive 24 VDC current from an external voltage supply (not shown). Power conditioning module 3502 may provide 24 VDC to LED driver module 3504. Power conditioning module 3502 may receive VDC current at any suitable voltage from an external voltage supply (not shown). Power conditioning module 3502 may provide any suitable VDC to LED driver module 3504.

Driver module 3504 may provide conditioned 24 VDC current to LED. Driver module 3504 may include DC-DC converting microcontroller 3508 (U1) for high-speed switching of current to LED driver module 3504 using MOSFET 3510 (Q1) coupled near low voltage end 3512 of germicidal emitter array 3506.

Microcontroller 3508 (U1) may receive at DIN pin 3514 (3) germicidal emitter enable voltage 3516. Enable voltage 3516 may be set by a microcontroller (not shown) based on settings or conditions such as one or more of a delay time, a duration ("ON time"), a sensor condition (such as motion or occupancy), and a user command.

Figures 35, 36:
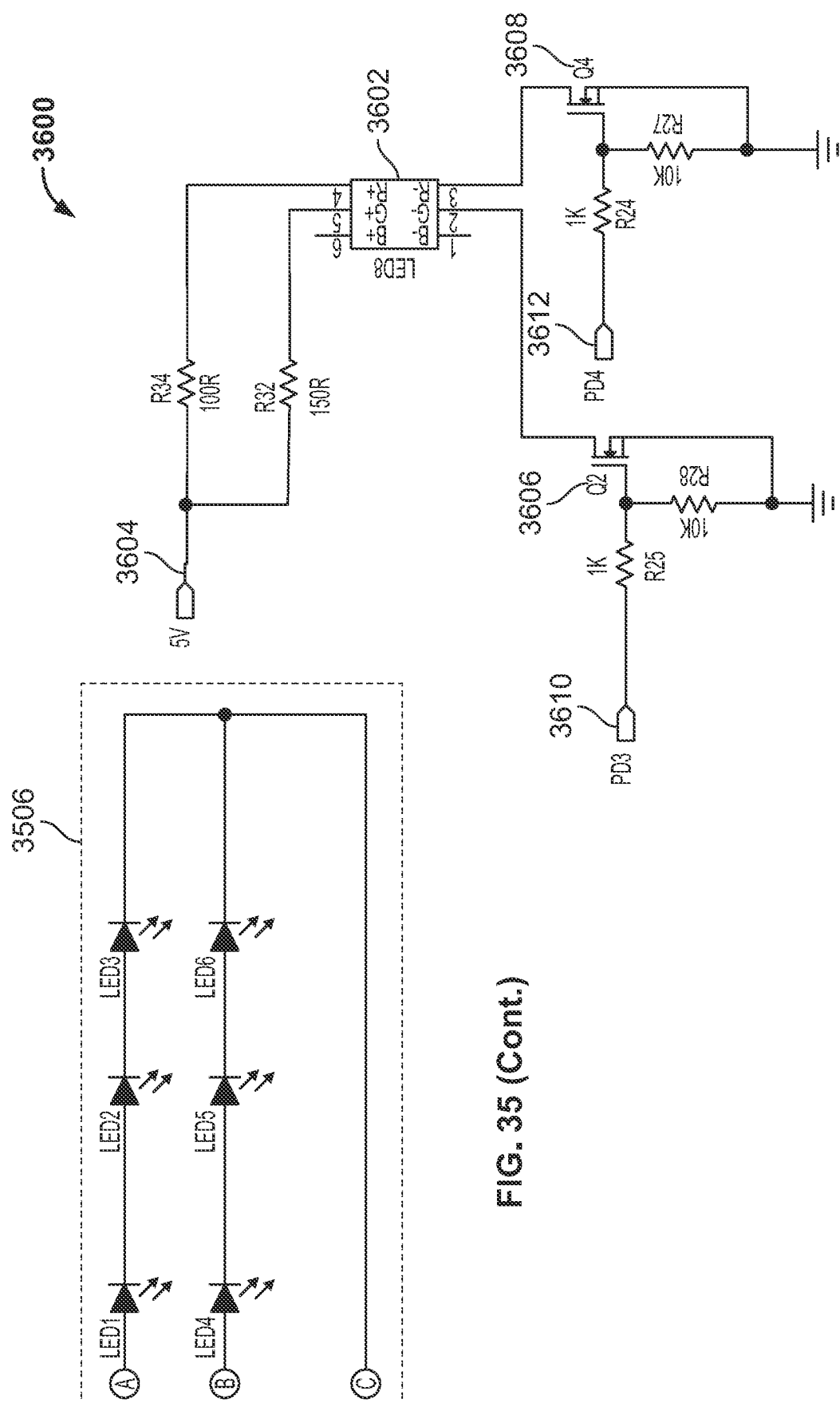
FIG. 36 shows schematically illustrative apparatus in accordance with principles of the invention.

FIG. 36 shows schematically illustrative visual spectrum LED circuit 3600. LED circuit 3600 may include RGB (red, green, blue) module 3602 (LED8).

Module 3602 (LED8) may include a blue emitter. Module 3602 (LED8) may include a green emitter. Module 3602 (LED8) may include a red emitter. Circuit 3600 may include MOSFET switch 3606 (Q2) in line with the green emitter. Circuit 3600 may include MOSFET switch 3608(Q4) in line with the red emitter. Circuit 3600 may include another MOSFET switch (not shown) in line with the blue emitter.

The microcontroller may, using pins such as 3610 (PD3) and 3612 (PD4) to open and close one or more of the emitters to signal to a user an operational state of the germicidal emitter array.

Module 3602 (LED8) may receive 5 VDC current 3604 from a current source (not shown).

Figures 37, 38:
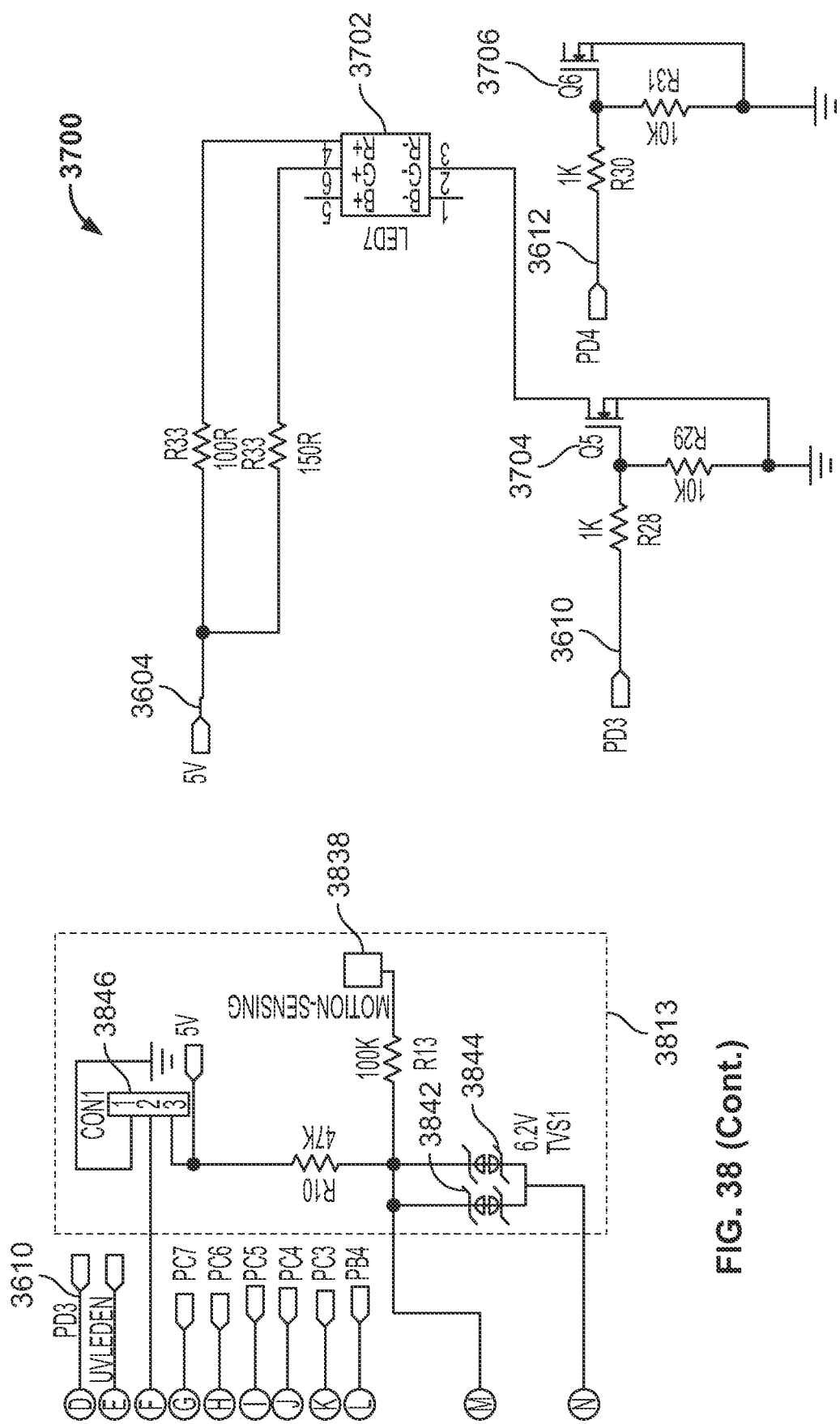
FIG. 37 shows schematically illustrative apparatus in accordance with principles of the invention.
FIG. 38 shows schematically illustrative apparatus in accordance with principles of the invention.
Figure 38:
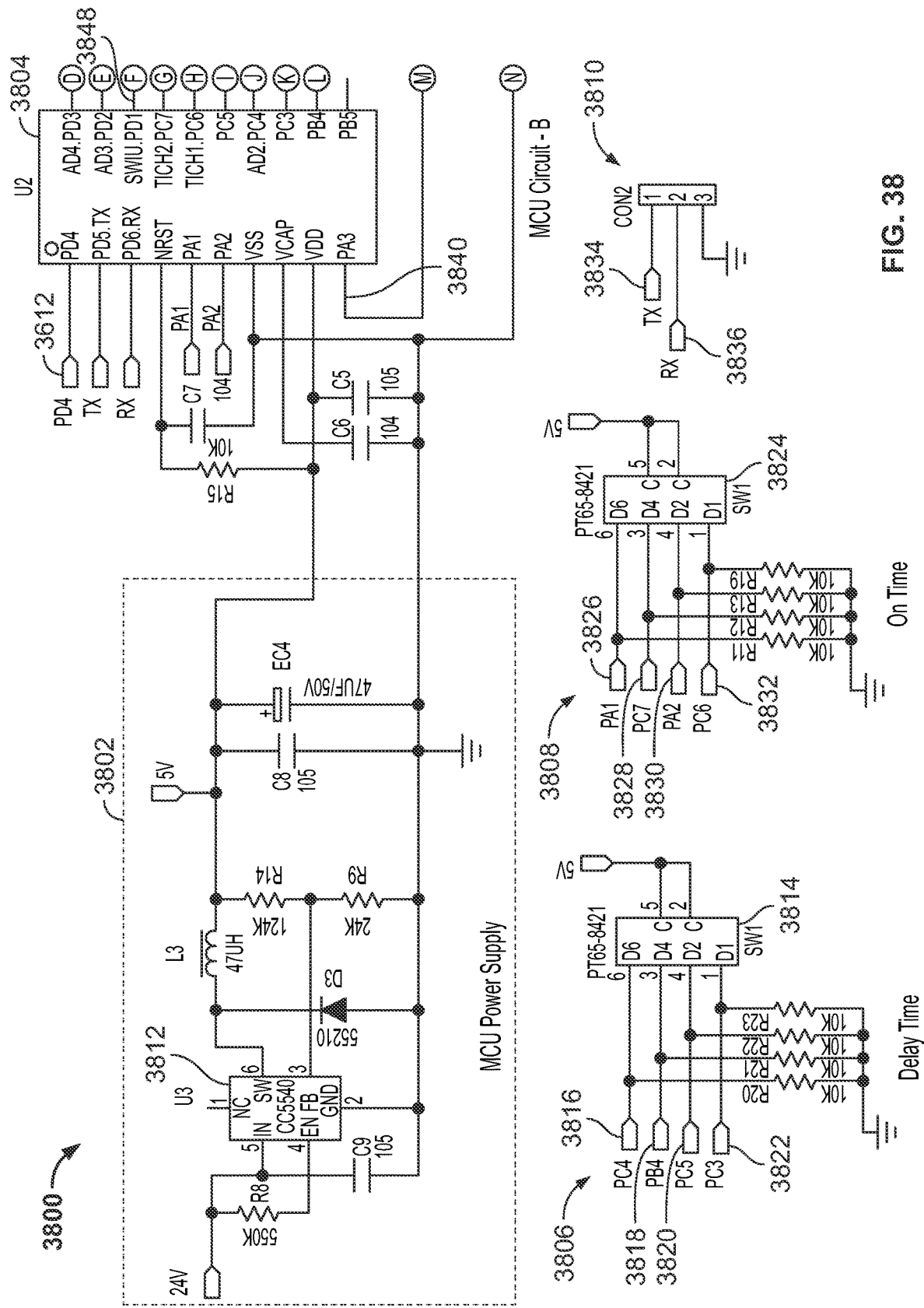

FIG. 37 shows schematically illustrative visual spectrum LED circuit 3700. LED circuit 3700 may include RGB (red, green, blue) module 3702 (LED7).

Module 3702 (LED7) may include a blue emitter. Module 3702 (LED7) may include a green emitter. Module 3702 (LED7) may include a red emitter. Circuit 3700 may include MOSFET switch 3704 (Q5) in line with the green emitter. Circuit 3700 may include MOSFET switch 3706 (Q6) in line with the red emitter. Circuit 3700 may include another MOSFET switch (not shown) in line with the blue emitter.

The microprocessor may, using pins such as 3610 (PD3) and 3612 (PD4) to open and close one or more of the emitters to signal to a user an operational state of the germicidal emitter array.

Module 3702 (LED7) may receive 5 VDC current 3604 from a current source (not shown).

FIG. 38 shows schematically illustrative microcontroller circuit 3800. Circuit 3800 may include power supply 3802. Circuit 3800 may include microcontroller 3804 (U2). Circuit 3800 may include delay-time module 3806. Circuit 3800 may include on-time module 3808. Circuit 3800 may include communication connector 3810 (CON2). Circuit 3800 may include motion sensing module 3813.

Power supply 3802 may be disposed in a housing such as 2710. Power supply 3802 may be disposed in an electrical box such as 3110.

Power supply 3802 may include linear regulator 3812 (U3). Linear regulator may be a low drop-out regulator. Regulator 3812 may convert 24 VDC to 5 VDC. Regulator 3812 may provide the 5 VDC to microcontroller 3804 (U2).

Regulator 3812 may provide the 5 VDC to visual spectrum LED circuit 3600. Regulator 3812 may provide the 5 VDC to visual spectrum LED circuit 3700. Regulator 3812 may provide the 5 VDC to supply to delay-time module 3806. Regulator 3812 may provide the 5 VDC to supply to on-time module 3808. Regulator 3812 may provide the 5 VDC to supply to motion sensing module 3813. Regulator 3812 may provide the 5 VDC to any other suitable components or auxiliary circuits of circuit 3800.

Delay-time module 3806 may include switch 3814 (SW2). Switch 3814 may be a rotary switch. Microcontroller 3804 may receive a voltage at one of pins 3816 (PC4), 3818 (PB4), 3820 (PC5) and 3822 (PC3), each corresponding to a user-selected position of switch 3814. The voltage may correspond to a selected delay-time. Microcontroller 3804 may be programmed to implement the delay time.

On-time module 3808 may include switch 3824 (SW1). Switch 3824 may be a rotary switch. Microcontroller 3804 may receive a voltage at one of pins 3826 (PA1), 3828 (PC7), 3830 (PA2) and 3832 (PC6), each corresponding to a user-selected position of switch 3824. The voltage may correspond to a selected on-time. Microcontroller 3804 may be programmed to implement the on-time.

Connector 3810 may be in electrical communication with a transmitter (not shown). The transmitter may be a wired transmitter. The transmitter may be a wireless transmitter. The receiver may be a wired receiver. The receiver may be a wireless receiver. Connector 3810 may be in electrical communication with a receiver (not shown). The transmitter and the receiver may transmit and receive information such as information 126. Connector 3810 may be connected to transmit terminal 3834 (TX). Connector 3810 may be connected to receive terminal 3836 (RX).

Motion sensing module 3813 may include motion sensor 3838. Motion sensor 3838 may detect motion in environment E. Motion sensor 3838 may detect motion outside environment E. In response to the motion, motion sensor 3838 may provide a voltage to microcontroller 3804 at pin 3840 (PA3). Voltage suppression diodes 3842 and 3844 may protect microcontroller 3804 from a voltage surge from motion sensor 3838. Connector 3846 may connect motion sensor 3838 with pin 3848 (SWIU.PD1). Microcontroller 3804 may power motion sensor 3838 ON and OFF through pin 3848. Microcontroller 3804 may adjust a sensing threshold or sensitivity of motion sensor 3838 through pin 3848. Motion sensor 3838 may include a manual switch that a user can use to power motion sensor 3838 ON and OFF. Motion sensor 3838 may include a manual switch that a user can use to adjust a sensing threshold or sensitivity of motion sensor 3838.

Table 19 lists illustrative features of a fixture such as 112.

TABLE 19

Illustrative features of a fixture such as 112.

| Length (f, in.) | Housing 2704 Material | Emitters per foot Germicidal | Emitters per foot Visible | Input voltage (VDC) | Power consumption (W/foot of fixture) |
|---|---|---|---|---|---|
| 12 | Extruded aluminum | 6 | 2 | 24 | 10 |
| 24 | | | | | |
| 36 | | | | | |
| Other suitable lengths | Other suitable makes and materials | Other suitable numbers | Other suitable numbers | Other suitable voltages | Other suitable power consumption linear densities |

Apparatus may omit features shown and/or described in connection with illustrative apparatus. Embodiments may include features that are neither shown nor described in connection with the illustrative apparatus. Features of illustrative apparatus may be combined. For example, an illustrative embodiment may include features shown in connection with another illustrative embodiment.

For the sake of illustration, the steps of the illustrated processes will be described as being performed by a "system." A "system" may include one or more of the features of the apparatus and schemae that are shown in FIG. 1-FIG. 38 and/or any other suitable device or approach. The "system" may include one or more means for performing one or more of the steps described herein.

The steps of methods may be performed in an order other than the order shown and/or described herein. Embodiments may omit steps shown and/or described in connection with illustrative methods. Embodiments may include steps that are neither shown nor described in connection with illustrative methods.

Illustrative method steps may be combined. For example, an illustrative process may include steps shown in connection with another illustrative process.

Figure 39:
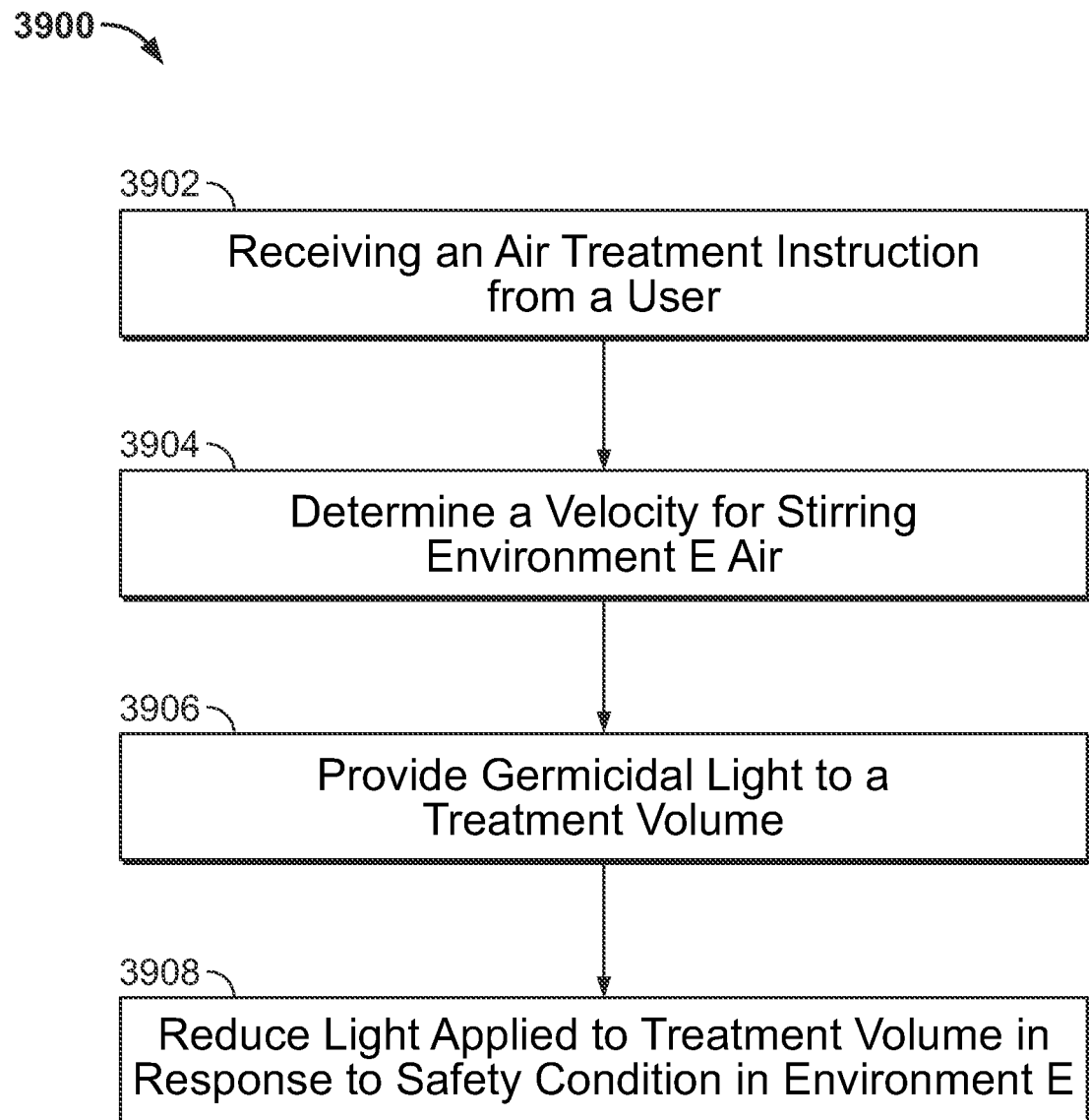
FIG. 39 shows illustrative steps of a process in accordance with principles of the invention.

FIG. 39 shows illustrative steps of process 3900 for providing germicidal light. At step 3902, the system may receive an air treatment instruction from a user. At step 3904, if a fan is present, the system may determine a velocity for stirring air in environment E. At step 3906, the system may provide germicidal light to volume. At step 3908, the system may reduce the beam volume in response to motion in environment E. At step 3908, the system may reduce the beam intensity in response to motion in environment E.

Figure 40:
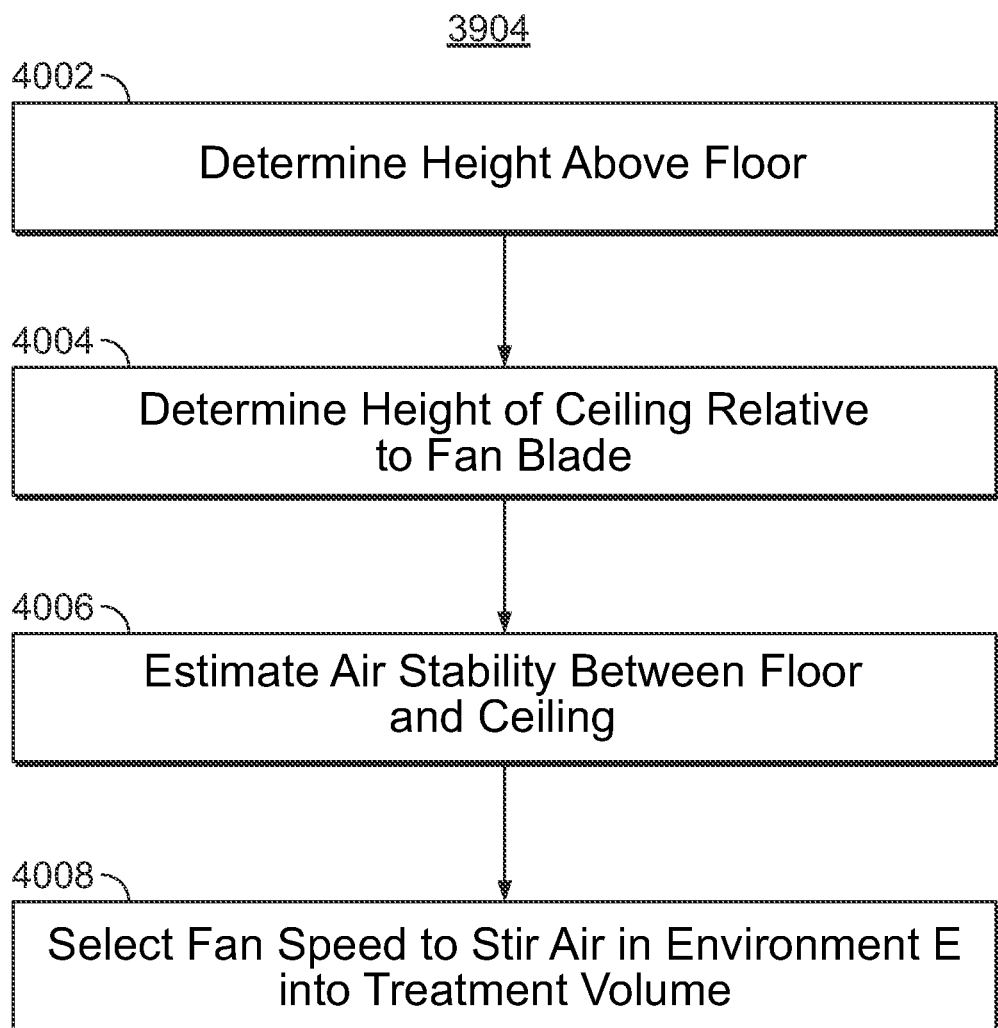
FIG. 40 shows illustrative steps of a process in accordance with principles of the invention.

FIG. 40 shows illustrative steps that may be performed in connection with step 3904 of process 3900. At step 4002, the system may determine a height above a floor. At step 4004, the system may determine a height of a ceiling relative to a fan blade. At step 4006, the system may estimate air stability between the floor and the ceiling based on sensed temperature and temperature differences. At step 4008, the system may select a fan speed to stir air in environment E into captive volume $V_1$.

Figure 41:
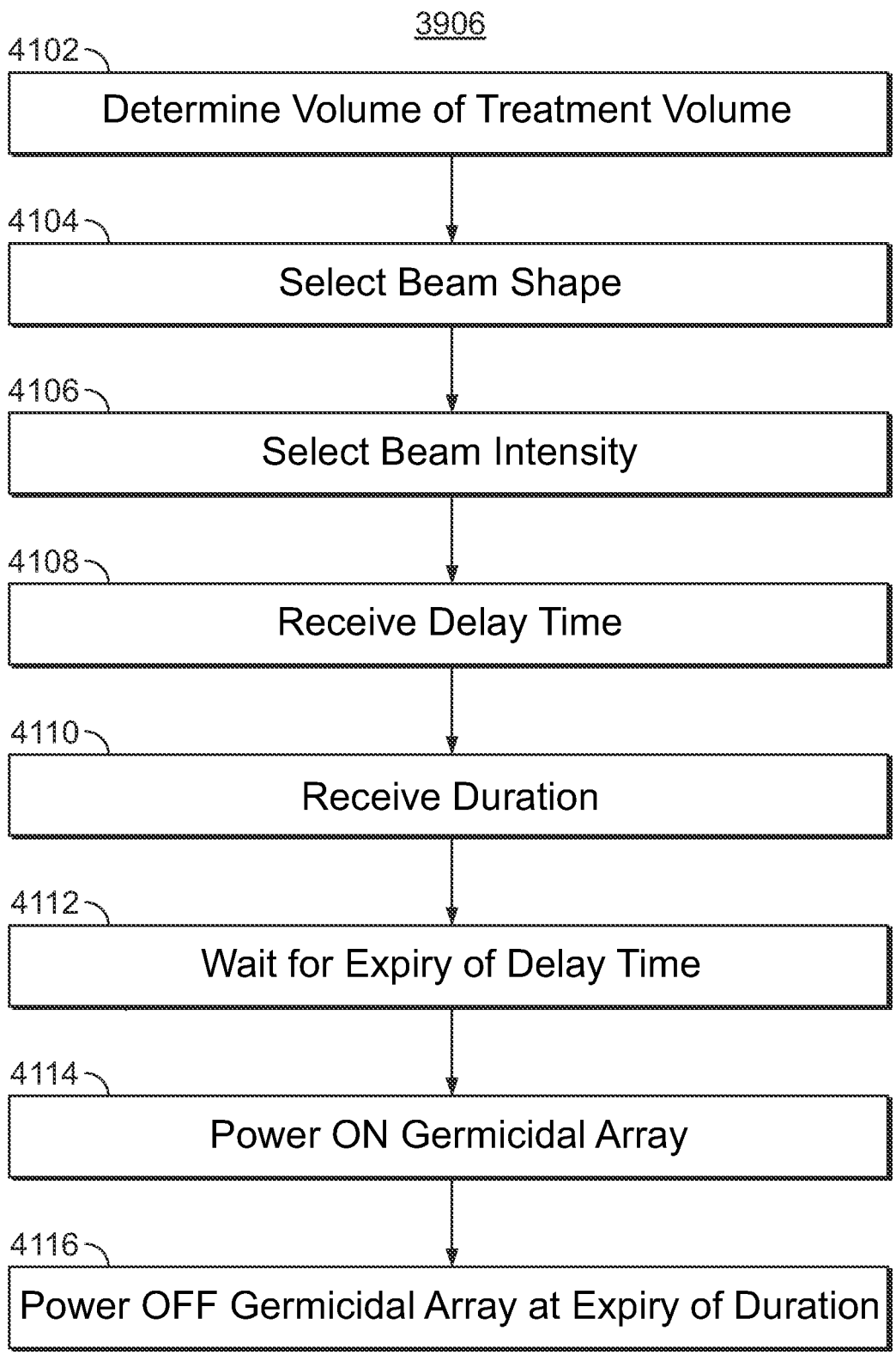
FIG. 41 shows illustrative steps of a process in accordance with principles of the invention.

FIG. 41 shows illustrative steps that may be performed in connection with step 3906 of process 3900. At step 4102, the system may determine the volume of captive volume $V_1$. At step 4104, the system may select a beam shape. At step 4106, the system may select a beam intensity. At step 4108, the system may receive a delay time. At step 4110, the system may receive a duration. At step 4112, the system may wait until expiry of the delay time. At step 4114, the system may power ON a germicidal emitter array. At step 4116, the system may power OFF the germicidal emitter array at the expiry of the duration.

Figure 42:
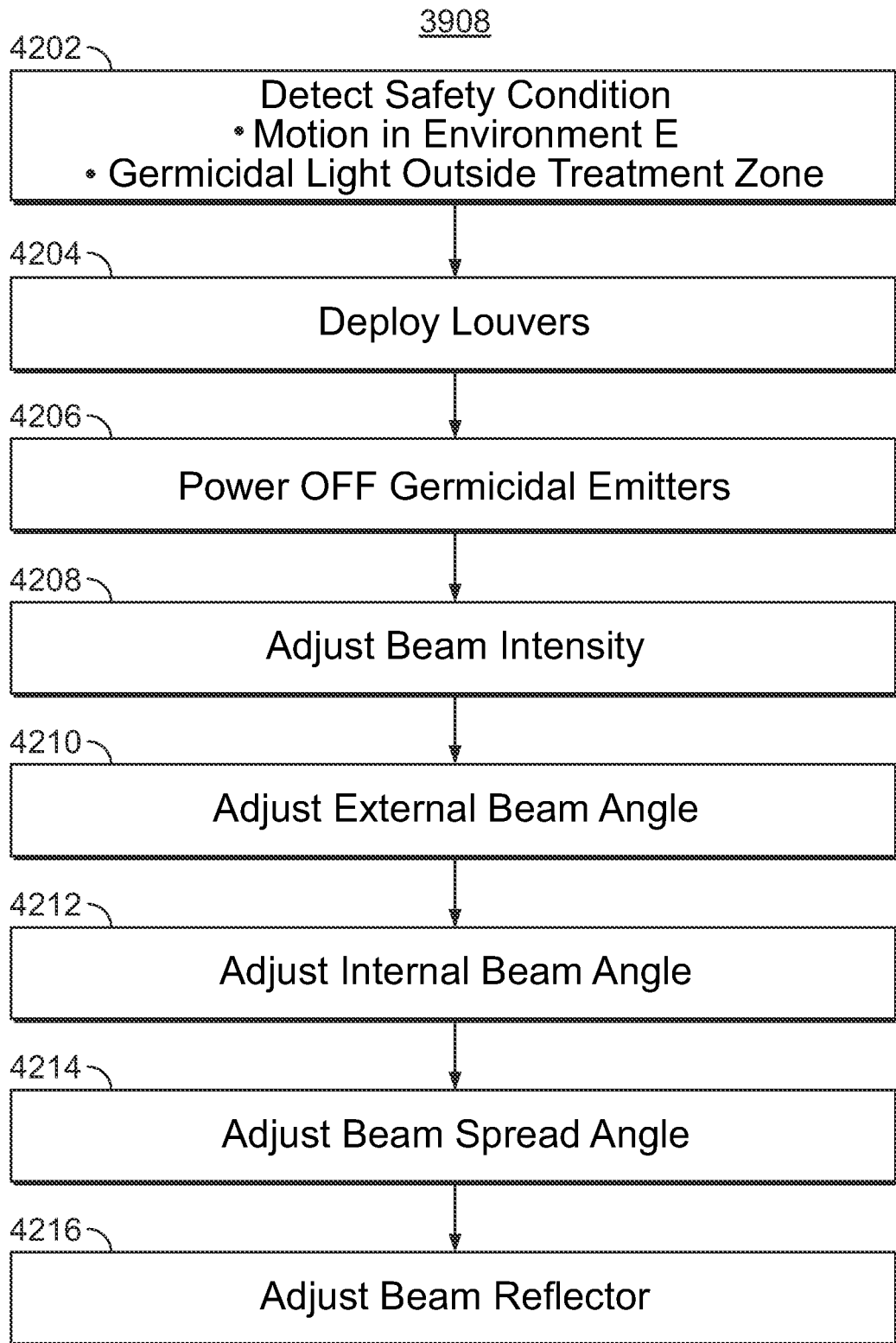
FIG. 42 shows illustrative steps of a process in accordance with principles of the invention.

FIG. 42 shows illustrative steps that may be performed in connection with step 3908 of process 3900. At step 4202, the system may detect a safety condition. The safety condition may include motion in environment E. The safety condition may include presence of germicidal light outside the captive volume. At step 4204, the system may deploy louvers. At step 4206, the system may power OFF germicidal emitters. At step 4208, the system may adjust beam intensity. At step 4210, the system may adjust an external beam angle such as $\theta_1$. At step 4212, the system may adjust an internal beam angle such as $\theta_2$. At step 4214, the system may adjust a beam spread angle such as beta. At step 4216, the system may adjust a beam reflector.

Embodiments may include features that are neither shown nor described in connection with the illustrative apparatus. Features of illustrative apparatus may be combined. For example, an illustrative embodiment may include features shown in connection with another illustrative embodiment. It is to be understood that structural, functional and procedural modifications or omissions may be made without departing from the scope and spirit of the present invention.

As will be appreciated by one of skill in the art, apparatus and methods shown or described herein may be embodied in whole or in part as a method, a data processing system, or a computer program product. Accordingly, such apparatus may take the form of, and such methods may be performed by, an entirely hardware embodiment, an entirely software embodiment or an embodiment combining software, hardware and any other suitable approach or apparatus.

All ranges and parameters disclosed herein shall be understood to encompass any and all subranges subsumed therein, every number between the endpoints, and the endpoints. For example, a stated range of "1 to 10" should be considered to include any and all subranges between (and inclusive of) the minimum value of 1 and the maximum value of 10; that is, all subranges beginning with a minimum value of 1 or more (e.g. 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

Functions of electrical circuits, or parts thereof, disclosed herein may be incorporated into or combined with other electrical circuits, or parts thereof, disclosed herein, or with other suitable electrical circuits.

Thus, apparatus, methods and algorithms for disinfecting air have been provided. Persons skilled in the art will appreciate that the present invention may be practiced by other than the described embodiments, which are presented for purposes of illustration rather than of limitation.

What is claimed is:

1. Apparatus for disinfecting air of a room, the apparatus comprising: a ceiling fan having a rotatable fan blade; a fixture configured to be suspended into the room from a ceiling; a light-emitting diode ("LED") that: is configured to emit germicidal light that is incident on the ceiling; is disposed in the fixture such that the LED does not rotate with the fan blade; and has an upper surface corresponding to a horizontal plane;

and an opaque surface defining a perimeter; wherein:
absent reflection off an environmental object, the apparatus does not emit germicidal light below the plane; if the germicidal light emitted by the LED propagates outward along the plane and is incident on the opaque surface, the opaque surface interferes with such germicidal light; and the LED is disposed inside the perimeter.

2. The apparatus of claim 1 further comprising a controller that is configured to control operation of the LED based on a flow of air above the plane.

3. The apparatus of claim 1 wherein the germicidal light is configured to neutralize a virion.

4. The apparatus of claim 1 wherein the germicidal light is configured to neutralize a bacterium.

5. The apparatus of claim 1 wherein the LED emits light having a wavelength that is no longer than ultraviolet.

6. The apparatus of claim 5 wherein the wavelength is in the UV-C spectrum.

7. The apparatus of claim 1 further wherein the fixture supports a louver that is configured to direct a beam of the germicidal light.

8. The apparatus of claim 1 further comprising an annular array of LEDs.

9. The apparatus of claim 8 wherein the fixture in operation emits germicidal light that propagates radially away from the annular array.

10. The apparatus of claim 9 wherein the fixture supports a louver that:
includes the opaque surface; and
is configured to direct a beam of the germicidal light.

11. The apparatus of claim 8 further comprising lensing disposed over the annular array.

12. The apparatus of claim 1 further comprising a controller that is configured to control the fixture; wherein the fixture is configured to direct a beam of the germicidal light.

13. The apparatus of claim 1 further comprising a controller that is configured to control the LED.

14. The apparatus of claim 13 further comprising a control interface in electronic communication with the controller; wherein the control interface is configured to receive an instruction conforming to a lighting control protocol.

15. The apparatus of claim 13 wherein the controller is configured to cause the LED to deliver to the air an amount of energy.

16. The apparatus of claim 15 wherein the controller is configured to adjust a duration of the energy.

17. The apparatus of claim 15 wherein the controller is configured to adjust an intensity of the energy.

18. The apparatus of claim 1 further comprising a reflection sensor configured to detect a reflection of light emitted by the LED from a structure.

19. The apparatus of claim 18 wherein the structure is the ceiling.

20. The apparatus of claim 1 wherein an energy level of the germicidal light is correlated to a setting of the fan.

21. The apparatus of claim 20 wherein the setting is speed.

22. The apparatus of claim 13 wherein the controller is further configured to cause the LED to deliver to the air a selected amount of energy.

23. The apparatus of claim 22 further comprising a range sensor that is configured to estimate a distance from the fixture to the ceiling; wherein:
in operation, a beam of the germicidal light is incident on the ceiling;
the beam has a beam spread;
the beam spread and the distance define a volume; and
the controller is further configured to select the amount of energy based on a flow of air through the volume.

24. The apparatus of claim 22 wherein the selected amount of energy is based on a volume of the air.

25. The apparatus of claim 13 wherein the controller is configured to change a characteristic of the germicidal light in response to a reflection of light from a structure.

26. The apparatus of claim 25 wherein the characteristic is energy emission.

27. The apparatus of claim 25 wherein the characteristic is energy intensity.

28. The apparatus of claim 1 further comprising a range sensor configured to estimate a distance corresponding to a position of the horizontal plane below the ceiling.

29. The apparatus of claim 28 further comprising a controller; wherein:
a beam of the germicidal light is incident on the ceiling;
the beam has a beam spread;
the beam spread and the distance define a volume; and
the controller is configured to estimate the volume.

30. The apparatus of claim 1 further comprising:
a controller; and
a detector that is configured to detect a presence of a living body;
wherein the controller is configured to change a beam characteristic of the germicidal light in response to detection of the living body by the detector.

* * * * *